US012648726B2

(12) United States Patent
Iwata et al.

(10) Patent No.: US 12,648,726 B2
(45) Date of Patent: Jun. 9, 2026

(54) SIGNAL PROCESSING METHODS AND SYSTEMS FOR BIOMAGNETIC FIELD IMAGING

(71) Applicant: SB Technology, Inc., Wilmington, DE (US)

(72) Inventors: Geoffrey Zerbinatti Iwata, San Francisco, CA (US); Christian Thieu Nguyen, Redwood City, CA (US); Kevin Robert Tharratt, Redwood City, CA (US); Maximilian Thomas Ruf, San Jose, CA (US); Tucker Blake Reinhardt, San Francisco, CA (US); Jordan Edward Crivelli-Decker, El Cerrito, CA (US); Madelaine Susan Zoritza Liddy, Mountain View, CA (US); Alison Emiko Rugar, Mountain View, CA (US); Fuxi Lu, Boston, MA (US); Ethan Jesse Pratt, Santa Clara, CA (US); Kit Yee Au-Yeung, San Diego, CA (US); Stefan Bogdanovic, Mountain View, CA (US)

(73) Assignee: SB Technology, Inc., Wilmington, DE (US)

( * ) Notice: Subject to any disclaimer, the term of this patent is extended or adjusted under 35 U.S.C. 154(b) by 0 days.

(21) Appl. No.: 18/882,672

(22) Filed: Sep. 11, 2024

(65) Prior Publication Data

US 2025/0000416 A1     Jan. 2, 2025

Related U.S. Application Data

(63) Continuation of application No. 18/607,352, filed on Mar. 15, 2024, now Pat. No. 12,303,273.

(Continued)

(51) Int. Cl.
*A61B 5/00* (2006.01)
*A61B 5/05* (2021.01)
(Continued)

(52) U.S. Cl.
CPC ............... *A61B 5/243* (2021.01); *A61B 5/05* (2013.01); *A61B 5/245* (2021.01); *A61B 5/7203* (2013.01);
(Continued)

(58) Field of Classification Search
CPC ........... A61B 5/243; A61B 5/245; A61B 5/05; A61B 5/7203; A61B 5/7246; A61B 5/725;
(Continued)

(56) References Cited

U.S. PATENT DOCUMENTS 6,856,830 B2     2/2005   He
7,130,675 B2     10/2006  Ewing et al.
(Continued)

FOREIGN PATENT DOCUMENTS

CN     112515679 A     3/2021
EP       1642526 A1     4/2006
(Continued)

OTHER PUBLICATIONS

D. Murzin et al., "Ultrasensitive Magnetic Field Sensors for Biomedical Applications," Sensors, vol. 20, No. 6, p. 1569, Mar. 2020, 32 pgs. doi: 10.3390/s20061569.
(Continued)

*Primary Examiner* — Joel F Brutus
(74) *Attorney, Agent, or Firm* — Morgan, Lewis & Bockius LLP

(57)     ABSTRACT

A computer system receives a plurality of signals corresponding to first time-series magnetic data generated from a plurality of unshielded magnetometers proximate to the
(Continued)

human subject. The first time-series magnetic data corresponds to magnetic fields generated from the human subject. The plurality of signals includes contributions from a biomagnetic field from at least a portion of the subject's organ and a background magnetic field. The computer system synchronizes the first time-series magnetic data to a common clock to generate synchronized time-series magnetic data. The computer system applies one or more filters to the synchronized time-series magnetic data to obtain filtered data. The computer system applies one or more noise reduction techniques to the filtered data to generate updated time-series magnetic data.

18 Claims, 28 Drawing Sheets
(13 of 28 Drawing Sheet(s) Filed in Color)

Related U.S. Application Data

(60) Provisional application No. 63/502,388, filed on May 15, 2023, provisional application No. 63/453,038, filed on Mar. 17, 2023, provisional application No. 63/453,041, filed on Mar. 17, 2023.

(51) Int. Cl.

| | |
|---|---|
| *A61B 5/243* | (2021.01) |
| *A61B 5/245* | (2021.01) |
| *G01R 33/02* | (2006.01) |
| *G01R 33/032* | (2006.01) |
| *G01R 33/04* | (2006.01) |
| *G01R 33/26* | (2006.01) |
| *A61B 90/50* | (2016.01) |

(52) U.S. Cl.
CPC ............ *A61B 5/7246* (2013.01); *A61B 5/725* (2013.01); *G01R 33/0206* (2013.01); *G01R 33/032* (2013.01); *G01R 33/04* (2013.01); *G01R 33/26* (2013.01); *A61B 90/50* (2016.02); *A61B 2562/0223* (2013.01); *A61B 2562/04* (2013.01); *A61B 2562/046* (2013.01)

(58) Field of Classification Search
CPC ........ A61B 2562/0223; A61B 2562/04; A61B 2562/046; G01R 33/0206; G01R 33/032; G01R 33/04; G01R 33/26
See application file for complete search history.

(56) References Cited

U.S. PATENT DOCUMENTS

| | | | |
|---|---|---|---|
| 7,197,352 | B2 | 3/2007 | Gott et al. |
| 7,365,534 | B2 | 4/2008 | Tralshawala et al. |
| 7,742,806 | B2 | 6/2010 | Sternickel et al. |
| 8,391,963 | B2 | 3/2013 | Sternickel et al. |
| 8,527,435 | B1 | 9/2013 | Han et al. |
| 8,565,606 | B2 | 10/2013 | Kim et al. |
| 8,744,557 | B2 | 6/2014 | Sternickel et al. |
| 8,941,516 | B2 | 1/2015 | Kim et al. |
| 9,173,614 | B2 | 11/2015 | Sternickel et al. |
| 9,433,363 | B1 | 9/2016 | Erasala et al. |
| 9,560,986 | B2 | 2/2017 | Varcoe |
| 9,655,564 | B2 | 5/2017 | Sternickel et al. |
| D790,065 | S | 6/2017 | O'Connor et al. |
| 9,788,741 | B2 | 10/2017 | Erasala et al. |
| 10,076,256 | B2 | 9/2018 | Erasala et al. |
| D875,951 | S | 2/2020 | Kent et al. |
| 10,602,940 | B1 | 3/2020 | Muchhala et al. |
| 10,925,502 | B2 | 2/2021 | Muchhala et al. |
| 10,952,628 | B2 | 3/2021 | Erasala et al. |
| 11,134,877 | B2 | 10/2021 | Erasala et al. |
| 11,375,935 | B2 | 7/2022 | Muchhala et al. |
| 11,454,679 | B2 | 9/2022 | Okatake et al. |
| 11,497,425 | B2 | 11/2022 | Kataoka et al. |
| 11,540,778 | B2 | 1/2023 | Taulu et al. |
| 11,547,337 | B2 | 1/2023 | Grant et al. |
| 11,585,869 | B2 | 2/2023 | Setegn et al. |
| 11,668,772 | B2 | 6/2023 | Kataoka |
| 11,774,518 | B2 | 10/2023 | Okatake et al. |
| 2002/0077537 | A1 | 6/2002 | Avrin et al. |
| 2003/0149354 | A1 | 8/2003 | Bakharev |
| 2004/0260169 | A1 | 12/2004 | Sternickel |
| 2005/0192502 | A1 | 9/2005 | Ishiyama et al. |
| 2011/0082360 | A1 | 4/2011 | Fuchs et al. |
| 2011/0152703 | A1 | 6/2011 | Zuckerman et al. |
| 2017/0035317 | A1 | 2/2017 | Jung et al. |
| 2017/0281026 | A1 | 10/2017 | Nick et al. |
| 2019/0133478 | A1 | 5/2019 | Varcoe et al. |
| 2019/0192021 | A1 | 6/2019 | Kim et al. |
| 2019/0298202 | A1 | 10/2019 | Nakamura et al. |
| 2019/0350474 | A1 | 11/2019 | Kim et al. |
| 2020/0170528 | A1 | 6/2020 | Erasala et al. |
| 2020/0178827 | A1 | 6/2020 | Al-Shimary et al. |
| 2020/0256929 | A1 | 8/2020 | Ledbetter et al. |
| 2020/0258627 | A1 | 8/2020 | Setegn et al. |
| 2020/0321124 | A1 | 10/2020 | Ford et al. |
| 2020/0341081 | A1 | 10/2020 | Mohseni et al. |
| 2020/0350106 | A1* | 11/2020 | Alford .................... H01F 5/003 |
| 2021/0041953 | A1 | 2/2021 | Poltorak |
| 2021/0161420 | A1 | 6/2021 | Nakamura et al. |
| 2021/0251545 | A1 | 8/2021 | Erasala et al. |
| 2021/0286023 | A1 | 9/2021 | Okatake et al. |
| 2021/0345898 | A1 | 11/2021 | Okatake et al. |
| 2021/0369165 | A1 | 12/2021 | Alford et al. |
| 2021/0373092 | A1 | 12/2021 | Iwata et al. |
| 2022/0015677 | A1 | 1/2022 | Erasala et al. |
| 2022/0054067 | A1* | 2/2022 | Shah .................... A61B 5/7203 |
| 2022/0378352 | A1 | 12/2022 | Muchhala et al. |
| 2023/0074561 | A1 | 3/2023 | Park et al. |
| 2023/0181077 | A1 | 6/2023 | Muchhala et al. |
| 2023/0181078 | A1 | 6/2023 | Erasala et al. |
| 2023/0204688 | A1 | 6/2023 | Setegn et al. |
| 2023/0329944 | A1 | 10/2023 | Erasala et al. |
| 2023/0400534 | A1 | 12/2023 | Morley et al. |
| 2024/0306969 | A1 | 9/2024 | Iwata et al. |

FOREIGN PATENT DOCUMENTS

| | | |
|---|---|---|
| WO | WO2008/127720 A2 | 10/2008 |
| WO | WO2019/034841 A1 | 2/2019 |
| WO | WO2020/120924 A1 | 6/2020 |

OTHER PUBLICATIONS

Y. Li et al., "Diagnostic outcomes of magnetocardiography in patients with coronary artery disease," Int. J. Clin. Exp. Med., vol. 8, No. 2, pp. 2441-2446, 2015, 6 pgs.

M. A. Khan, J. Sun, B. Li, A. Przybysz, and J. Kosel, "Magnetic sensors—A review and recent technologies," Eng. Res. Express, vol. 3, No. 2, p. 022005, Jun. 2021, 23 pgs. doi: 10.1088/2631-8695/ac0838.

R. Agarwal, A. Saini, T. Alyousef, and C. A. Umscheid, "Magnetocardiography for the diagnosis of coronary artery disease: a systematic review and meta-analysis," Ann. Noninvasive Electrocardiol. Off. J. Int. Soc. vol. 17, No. 4, pp. 291-298, Oct. 2012, 8 pgs. doi: 10.1111/j.1542-474X.2012.00538.x.

H. Kwon et al., "Non-Invasive Magnetocardiography for the Early Diagnosis of Coronary Artery Disease in Patients Presenting With Acute Chest Pain," Circ. J., vol. 74, No. 7, pp. 1424-1430, 2010, 7 pgs. doi: 10.1253/circj.CJ-09-0975.

V. R. Bhat, B. Pal, H. Anitha, and A. Thalengala, "Localization of magnetocardiographic sources for myocardial infarction cases using deterministic and Bayesian approaches," Sci. Rep., vol. 12, No. 1, p. 22079, Dec. 2022, 16 pgs. doi: 10.1038/s41598-022-25919-3.

A. J. Camm et al., "Clinical utility of magnetocardiography in cardiology for the detection of myocardial ischemia," J. Electrocardiol., vol. 57, pp. 10-17, Nov. 2019, 8 pgs. doi: 10.1016/j.jelectrocard.2019.07.009.

(56)          References Cited

OTHER PUBLICATIONS

V. Mäntynen, T. Konttila, and M. Stenroos, "Investigations of sensitivity and resolution of ECG and MCG in a realistically shaped thorax model," Phys. Med. Biol., vol. 59, No. 23, p. 7141, Nov. 2014, 19 pgs. doi: 10.1088/0031-9155/59/23/7141.

E. A. P. Alday, H. Ni, C. Zhang, M. A. Colman, Z. Gan, and H. Zhang, "Comparison of Electric- and Magnetic-Cardiograms Produced by Myocardial Ischemia in Models of the Human Ventricle and Torso," PLOS ONE, vol. 11, No. 8, p. e0160999, Aug. 2016, 17 pgs. doi: 10.1371/journal.pone.0160999.

I. Chaikovsky et al., "Value of magnetocardiography in chronic coronary disease detection: results of multicenter trial," Eur. Heart J., vol. 42, No. Supplement_1, p. ehab724.1171, Oct. 2021, 1 pg. doi: 10.1093/eurheartj/ehab724.1171.

T. Lachlan et al., "Magnetocardiography parameters to predict future Sudden Cardiac Death (MAGNETO-SCD) or ventricular events from implantable cardioverter defibrillators: study protocol, design and rationale," BMJ Open, vol. 10, No. 10, p. e038804, Oct. 2020, 7 pgs. doi: 10.1136/bmjopen-2020-038804.

J. Park, B. Leithäuser, P. Hill, and F. Jung, "Resting Magnetocardiography Predicts 3-Year Mortality in Patients Presenting with Acute Chest Pain without ST Segment Elevation," Ann. Noninvasive Electrocardiol. Off. J. Int. Soc. Holter Noninvasive Electrocardiol. Inc, vol. 13, No. 2, pp. 171-179, Apr. 2008, 9 pgs. doi: 10.1111/j.1542-474X.2008.00217.x.

B. A. Steinberg, A. Roguin, S. P. Watkins, P. Hill, D. Fernando, and J. R. Resar, "Magnetocardiogram Recordings in a Nonshielded Environment-Reproducibility and Ischemia Detection," Ann. Noninvasive Electrocardiol., vol. 10, No. 2, pp. 152-160, Apr. 2005, 9 pgs. doi: 10.1111/j.1542-474X.2005.05611.x.

M. E. Pena et al., "A 90-second magnetocardiogram using a novel analysis system to assess for coronary artery stenosis in Emergency department observation unit chest pain patients," IJC Heart Vasc., vol. 26, p. 100466, Feb. 2020, 7 pgs. doi: 0.1016/j.ijcha.2019.100466.

M. Goernig et al., "Magnetocardiography based spatiotemporal correlation analysis is superior to conventional ECG analysis for identifying myocardial injury," Ann. Biomed. Eng., vol. 37, No. 1, pp. 107-111, Jan. 2009, 5 pgs. doi: 10.1007/s10439-008-9598-5.

H. Ikefuji et al., "Visualization of cardiac dipole using a current density map: detection of cardiac current undetectable by electrocardiogramg magnetocardiography," J. Med. Invest., vol. 54, No. 1-2, pp. 116-123, 2007, 8 pgs. doi: 10.2152/jmi.54.116.

H. Kyoon Lim, K. Kim, Y.-H. Lee, and N. Chung, "Detection of non-ST-elevation myocardial infarction using magnetocardiogram: New information from spatiotemporal electrical activation map," Ann. Med., vol. 41, No. 7, pp. 533-546, Jan. 2009, 15 pgs. doi: 10.1080/07853890903107883.

Y.-C. Chang et al., "Early Myocardial Repolarization Heterogeneity Is Detected by Magnetocardiography in Diabetic Patients with Cardiovascular Risk Factors," PLOS ONE, vol. 10, No. 7, p. e0133192, Jul. 2015, 12 pgs. doi: 10.1371/journal.pone.0133192.

C. D. Fokoua-Maxime, E. Lontchi-Yimagou, T. E. Cheuffa-Karel, T. L. Tchato-Yann, and S. Pierre-Choukem, "Prevalence of asymptomatic or 'silent' myocardial ischemia in diabetic patients: Protocol for a systematic review and meta-analysis," PLOS ONE, vol. 16, No. 6, p. e0252511, Jun. 2021, 7 pgs. doi: 10.1371/journal.pone.0252511.

J. F. Strasburger, B. Cheulkar, and R. T. Wakai, "Magnetocardiography for fetal arrhythmias," Heart Rhythm, vol. 5, No. 7, pp. 1073-1076, Jul. 2008, 6 pgs. doi: 10.1016/j.hrthm.2008.02.035.

M. Batie, S. Bitant, J. F. Strasburger, V. Shah, O. Alem, and R. T. Wakai, "Detection of Fetal Arrhythmia by Using Optically Pumped Magnetometers," JACC Clin. Electrophysiol., vol. 4, No. 2, pp. 284-287, Feb. 2018, 8 pgs. doi: 10.1016/j.jacep.2017.08.009.

Y. Yang et al., "A new wearable multichannel magnetocardiogram system with a SERF atomic magnetometer array," Sci. Rep., vol. 11, No. 1, p. 5564, Mar. 2021, 11 pgs. doi: 10.1038/s41598-021-84971-7.

Y. Zhai, Z. Yue, L. Li, and Y. Liu, "Progress and applications of quantum precision measurement based on SERF effect," Front. Phys., vol. 10, p. 969129, Oct. 2022, 18 pgs. doi: 10.3389/fphy.2022.969129.

T. M. Tierney et al., "Optically pumped magnetometers: From quantum origins to multi-channel magnetoencephalography," NeuroImage, vol. 199, pp. 598-608, Oct. 2019, 11 pgs. doi: 10.1016/j.neuroimage.2019.05.063.

M. Pena et al., "Magnetocardiography Using a Novel Analysis System (Cardioflux) in the Evaluation of Emergency Department Observation Unit Chest Pain Patients," Ann. Emerg. Med., vol. 72, No. 4, p. S2, Oct. 2018, 1 pg. doi: 10.1016/j.annemergmed.2018.08.008.

J. W. Mooney, S. Ghasemi-Roudsari, E. R. Banham, C. Symonds, N. Pawlowski, and B. T. H. Varcoe, "A portable diagnostic device for cardiac magnetic field mapping," Biomed. Phys. Eng. Express, vol. 3, No. 1, p. 015008, Jan. 2017, 11 pgs. doi: 10.1088/2057-1976/3/1/015008.

S. Sengottuvel et al., "Feasibility study on measurement of magnetocardiography (MCG) using fluxgate magnetometer," presented at the DAE Solid State Physics Symposium 2017, Mumbai, India, 2018, 5 pgs. doi: 10.1063/1.5028788.

K. Kurashima et al., "Development of Magnetocardiograph without Magnetically Shielded Room Using High-Detectivity TMR Sensors," Sensors, vol. 23, No. 2, p. 646, Jan. 2023, 18 pgs. doi: 10.3390/s23020646.

R. J. Clancy, V. Gerginov, O. Alem, S. Becker, and S. Knappe, "A study of scalar optically-pumped magnetometers for use in magnetoencephalography without shielding," Phys. Med. Biol., vol. 66, No. 17, p. 175030, Sep. 2021, 14 pgs. doi: 10.1088/1361-6560/ac18fb.

R. Fenici, R. Mashkar, and D. Brisinda, "Performance of miniature scalar atomic magnetometers for magnetocardiography in an unshielded hospital laboratory for clinical electrophysiology," Eur. Heart J., vol. 41, No. Supplement_2, p. ehaa946.0386, Nov. 2020, 1 pg. doi: 10.1093/ehjci/ehaa946.0386.

A. Fabricant, I. Novikova, and G. Bison, "How to build a magnetometer with thermal atomic vapor: a tutorial," New J. Phys., vol. 25, No. 2, p. 025001, Feb. 2023, 29 pgs. doi: 10.1088/1367-2630/acb840.

R. Zhang, K. Smith, and R. Mhaskar, "Highly sensitive miniature scalar optical gradiometer," in 2016 IEEE Sensors, Oct. 2016, 3 pgs. doi: 10.1109/ICSENS.2016.7808768.

M. A. Uusitalo and R. J. Ilmoniemi, "Signal-space projection method for separating MEG or EEG into components," Med. Biol. Eng. Comput., vol. 35, No. 2, pp. 135-140, Mar. 1997, 6 pgs. doi: 10.1007/BF02534144.

A. Gapelyuk et al., "Detection of patients with coronary artery disease using cardiac magnetic field mapping at rest," J. Electrocardiol., vol. 40, No. 5, pp. 401-407, 2007, 7 pgs. doi: 10.1016/j.jelectrocard.2007.03.013.

R. Ramesh et al., "Magnetocardiography for identification of coronary ischemia in patients with chest pain and normal resting 12-lead electrocardiogram," Ann. Noninvasive Electrocardiol., vol. 25, No. 3, May 2020, 8 pgs. doi: 10.1111/anec.12715.

M. Janosek et al., "1-pT noise fluxgate magnetometer for geomagnetic measurements and unshielded magnetocardiography," IEEE Transactions on Instrumentation and Measurement (vol. 69, Issue: 5, May 2020), 8 pgs.

D. Brisinda, A. M. Meloni, and R. Fenici, "First 36-Channel Magnetocardiographic Study of CAD Patients in an Unshielded Laboratory for Interventional and Intensive Cardiac Care," Functional Imaging and Modeling of the Heart, 2003, vol. 2674, pp. 122-131, 11 pgs.

Iwata et al., Non-Final Office Action, U.S. Appl. No. 18/607,317, dated Jun. 14, 2024, 14 pgs.

Iwata et al., Non-Final Office Action, U.S. Appl. No. 18/607,352, dated Jul. 5, 2024, 13 pgs.

SB Technology, Inc., PCT/US2024/020455, International Search Report and Written Opinion dated Jun. 15, 2024, 18 pgs.

Iwata et al., Final Office Action, U.S. Appl. No. 18/607,317, dated Sep. 18, 2024, 13 pgs.

(56)  References Cited

OTHER PUBLICATIONS

Iwata et al., Final Office Action, U.S. Appl. No. 18/607,352, dated
Nov. 5, 2024, 5 pgs.

* cited by examiner

Computer System 120

Figure 4D inset

Magnetometer spacing E1 < E2 < E3 < E4
Magnetometer spacing F1 < F2

(ii) Signals after
synchronization, filtering
and linear regression
gradiometry (i) Signals after
synchronization
and filtering

Figure 14A:
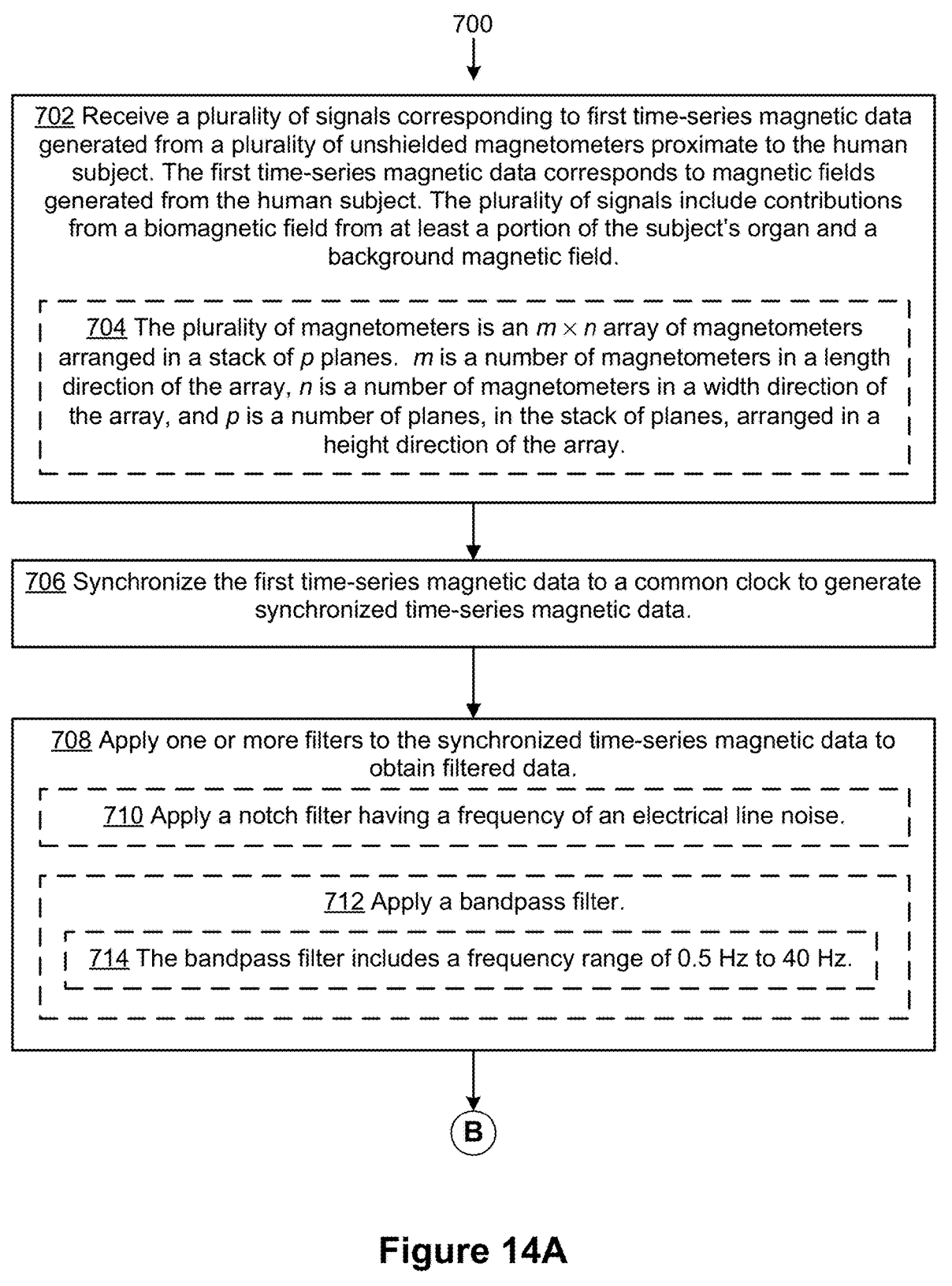

700

702 Receive a plurality of signals corresponding to first time-series magnetic data generated from a plurality of unshielded magnetometers proximate to the human subject. The first time-series magnetic data corresponds to magnetic fields generated from the human subject. The plurality of signals include contributions from a biomagnetic field from at least a portion of the subject's organ and a background magnetic field.

> 704 The plurality of magnetometers is an $m \times n$ array of magnetometers arranged in a stack of $p$ planes. $m$ is a number of magnetometers in a length direction of the array, $n$ is a number of magnetometers in a width direction of the array, and $p$ is a number of planes, in the stack of planes, arranged in a height direction of the array.

706 Synchronize the first time-series magnetic data to a common clock to generate synchronized time-series magnetic data.

708 Apply one or more filters to the synchronized time-series magnetic data to obtain filtered data.

> 710 Apply a notch filter having a frequency of an electrical line noise.

> 712 Apply a bandpass filter.
>
> > 714 The bandpass filter includes a frequency range of 0.5 Hz to 40 Hz.

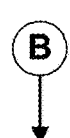

716 Apply one or more noise reduction techniques to the filtered data to generate updated time-series magnetic data.

718 Obtain positional information corresponding to each magnetometer in the plurality of magnetometers.

720 For a respective pair of magnetometers, in the plurality of magnetometers, consisting of a respective first magnetometer positioned in the first plane and a respective second magnetometer positioned in the second plane, wherein the respective first magnetometer and the second respective magnetometer are aligned with respect to each other in the length direction and the width direction, calculate a difference between a first filtered signal corresponding to the respective first magnetometer and a second filtered signal corresponding to the second respective magnetometer.

722 Determine a correlation between the first filtered signal and the filtered second signal using linear regression.

724 Calculate the difference according to the determined correlation.

726 Apply principal component analysis (PCA) to extract, from the filtered data, a subset of variables from all variables of the filtered data.

727 Determine a plurality of principal components (PCs) corresponding to the filtered data. Assign a value of zero to a subset of the plurality of PCs, thereby removing one or more noise contributions from the filtered data.

728 Apply signal source separation (SSS) to the filtered data.

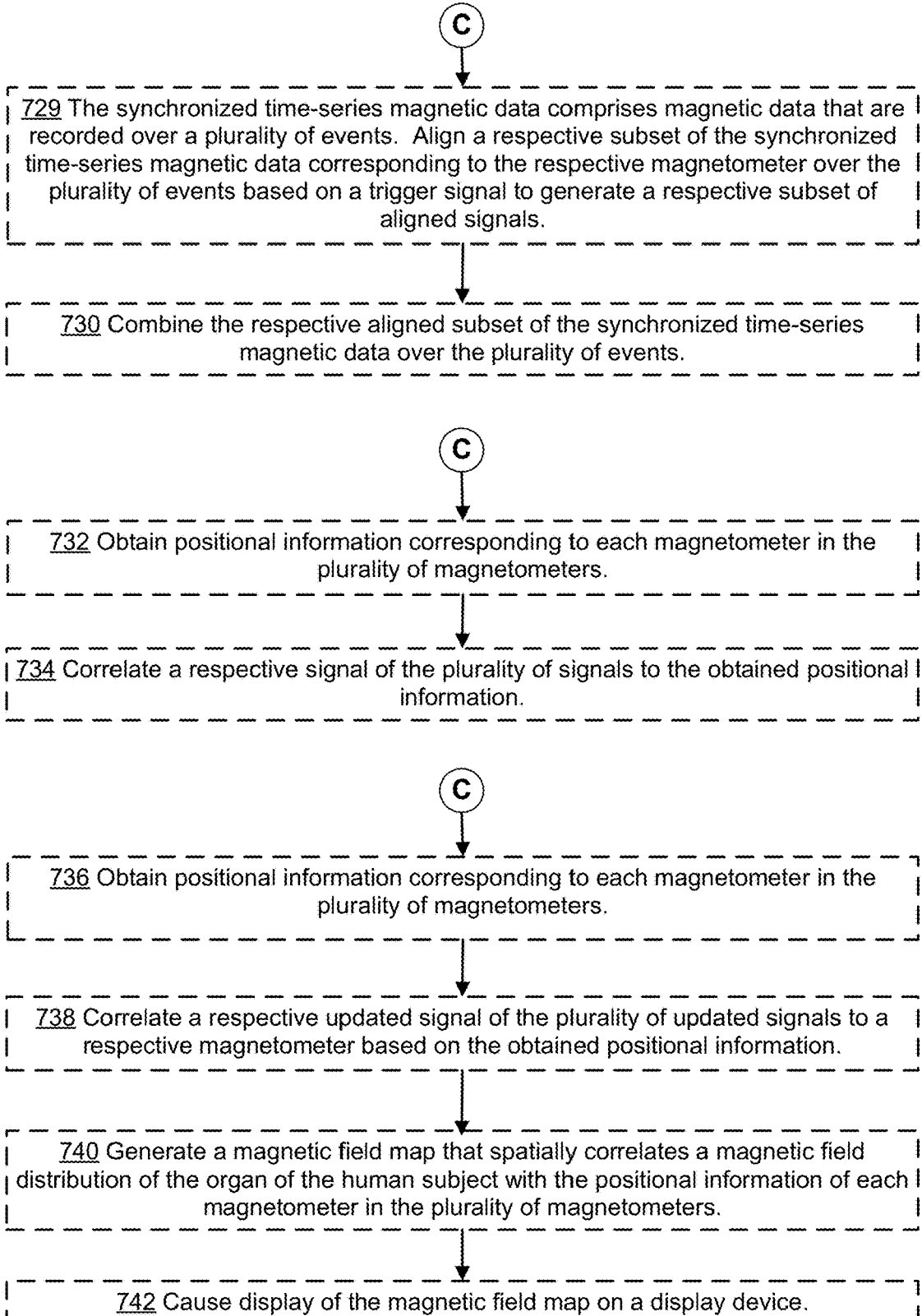

C

729 The synchronized time-series magnetic data comprises magnetic data that are recorded over a plurality of events. Align a respective subset of the synchronized time-series magnetic data corresponding to the respective magnetometer over the plurality of events based on a trigger signal to generate a respective subset of aligned signals.

730 Combine the respective aligned subset of the synchronized time-series magnetic data over the plurality of events.

C

732 Obtain positional information corresponding to each magnetometer in the plurality of magnetometers.

734 Correlate a respective signal of the plurality of signals to the obtained positional information.

C

736 Obtain positional information corresponding to each magnetometer in the plurality of magnetometers.

738 Correlate a respective updated signal of the plurality of updated signals to a respective magnetometer based on the obtained positional information.

740 Generate a magnetic field map that spatially correlates a magnetic field distribution of the organ of the human subject with the positional information of each magnetometer in the plurality of magnetometers.

742 Cause display of the magnetic field map on a display device.

| 744 The plurality of magnetometers comprises a plurality of vector magnetometers. After receiving the plurality of signals, corresponding to vector field signals from the plurality of vector magnetometers, compute a dot product of the vector field signals to obtain the first time-series magnetic data.

SIGNAL PROCESSING METHODS AND SYSTEMS FOR BIOMAGNETIC FIELD IMAGING

RELATED APPLICATIONS

This application is a continuation of U.S. patent application Ser. No. 18/607,352, filed Mar. 15, 2024, titled "Signal Processing Methods and Systems for Biomagnetic Field Imaging," now issued as U.S. Pat. No. 12,303,273 on May 20, 2025, which claims priority to (i) U.S. Provisional Patent Application No. 63/453,038, filed Mar. 17, 2023, titled "Systems and Methods for Biomagnetic Field Imaging," (ii) U.S. Provisional Patent Application No. 63/453,041, filed Mar. 17, 2023, titled "Signal Processing Methods and Systems for Biomagnetic Field Imaging," and (iii) U.S. Provisional Patent Application No. 63/502,388, filed May 15, 2023, titled "Bedside Magnetocardiography With A Scalar Sensor Array" All of the aforementioned applications are incorporated by reference herein in their entireties.

This application is related to U.S. patent application Ser. No. 18/607,317, filed Mar. 15, 2024, titled "Systems and Methods for Biomagnetic Field Imaging," which is incorporated by reference herein in its entirety.

TECHNICAL FIELD

The disclosed embodiments relate generally to systems and methods for detecting electrical activity in a human anatomy via magnetic field sensing.

BACKGROUND

Measurements of biomagnetic fields in a human subject can be used to understand potential disease states. For example, magnetoencephalography (MEG) is a non-invasive technique for investigating human brain activity. Magnetocardiography (MCG) is a non-invasive technique for measuring magnetic fields produced by electric currents in the heart. Similar to an electrocardiogram, a magnetocardiogram has morphological features such as a QRS complex, P-waves, and T-waves.

Decades of research have shown that magnetocardiography (MCG) has the potential to improve cardiac care decisions. However, sensor and system limitations have prevented its widespread adoption in clinical practice.

SUMMARY

Magnetocardiography (MCG) is a non-invasive imaging technology that has shown promise for improving clinical diagnostics. MCG records the magnetic fields outside the body that result from electrical activity in myocardial fibers. Magnetic field maps (MFMs) obtained from MCG can provide detailed information about the propagation of electrical activity in the heart with minimal distortion, since magnetic fields propagate unimpeded through tissue.

MCG has already been utilized for diagnosis of coronary artery diseases such as ischemic heart conditions, where blood vessels may narrow due to plaque buildup, resulting in an inadequate and non-uniform distribution of blood and oxygen in the heart. MCG can not only detect subtle changes in magnetic fields due to ischemia, but also provide source localization of ischemic regions, aiding with treatment planning.

Numerous studies have demonstrated that MCG can provide complementary information to electrocardiography (ECG) more confident identification of ischemic disease using MFMs, which can be parameterized by various features of the magnetic field morphology. In certain cases, MCG has been shown to provide high sensitivity in detecting coronary ischemia even when the corresponding ECG results are inconclusive, reinforcing its promise for clinical use.

MCG has several advantages over electrocardiography (ECG). First, MCG is less impacted by alterations in thoracic conductivity distributions than ECG. Unlike ECGs, in which electric signals can be distorted as they pass through body tissue, magnetic fields are unimpeded by the human body. By measuring more pristine electrical conduction activities in every heartbeat, doctors can better detect abnormal patterns or uncover other indicators about potential disease states. Since MCG is less affected by body conductivity, a sensitive MCG device could reveal subtle functional changes or hypoperfusion that might not appear in an ECG. Second, an MCG device that uses an array of sensors can produce magnetic maps of cardiac activity whereas it is not possible to produce such maps using a standard 12-lead ECG. Furthermore, MCG provides non-contact measurements, which would be valuable in applications where the use of ECG electrodes is not possible, such as in the evaluation of fetuses with life-threatening arrhythmia.

Current MCG devices have several drawbacks, including high operating costs and bulkiness in size (e.g., an MCG device can occupy the size of an entire room). To-date, most MCG devices are based on superconducting quantum interference device (SQUID) technology. Although SQUID magnetometers are considered as one of the most sensitive types of quantitative magnetometers, they must be operated at cryogenic temperatures. Furthermore, MEG or MCG measurements (using most modalities) are typically performed in magnetically shielded rooms to enhance the signal-to-noise ratios of the small biomagnetic signals.

One of the major challenges in detecting biomagnetic signals, such as cardiac signals, using unshielded magnetometers is that the biomagnetic signals tend to have small/weak amplitudes that are masked by magnetic interference from sources external to the target organ. Using a human heart as an example, the strength of the Earth's magnetic field is approximately 50 micro Teslas, which is about a million times larger in amplitude than the expected signal of the heart's magnetic field when the MCG device is positioned just outside the chest of a human subject (e.g., a patient). Furthermore, when the MCG device is deployed in a hospital or a clinical setting, other objects in the vicinity of the MCG device, such as other medical devices, computers, cellphones, TVs, or elevators in the building where the MCG device is deployed, also generate spurious magnetic noise and interference, thus making it even more difficult to pick out magnetic signals that are actually coming from the heart. The typical solution to this is to acquire MCG data in a magnetically-shielded environment so that the dominant signal measured by the magnetic sensor will actually originate from the heart. However, this solution is costly and impractical, and a primary reason why MCG has not been widely adopted in a clinical setting.

Accordingly, there is a need for improved systems, methods, and devices that enable measurement of magnetic fields produced by a target organ (e.g., heart or brain), while rejecting non-target related interference. The present disclosure describes an improved system, device and method for magnetometry imaging, by combining hardware components and signal processing techniques to resolve magnetic fields from a target organ (e.g., heart or brain) of a human subject.

As disclosed herein, in some embodiments, the system and/or device comprises a fixed (e.g., rigid), three-dimensional arrangement of magnetometers that are configured to operate in a large uniform field such as provided by the Earth (i.e., in a magnetically unshielded environment). In some embodiments, the magnetometers are mounted on (or within) a panel. During device operation, the plurality of magnetometers detects biomagnetic fields from a subject's organ in the presence of background magnetic field from the earth.

As disclosed herein, in some embodiments, the device is a magnetocardiography (MCG) device for measuring magnetic signals from a subject's heart. In some embodiments, the device is a magnetoencephalography (MEG) device for measuring magnetic signals from a subject's brain.

As disclosed herein, in some embodiments, the device includes a plurality of magnetometers having an average spacing that satisfies a constraint in Fourier space. In some embodiments, the magnetometers are spatially distributed such that in Fourier space, the magnetometers have a wavevector coverage to recover information from both the biomagnetic field from the subject's organ and the background magnetic field, to allow discrimination between those fields and inference about the health characteristics of the human subject based on the organ field.

As disclosed herein, in some embodiments, the plurality of magnetometers comprises an array of magnetic field sensors (e.g., magnetometers), in which the sensors are arranged in multiple layers. The combination of the array dimensions, sensor arrangement, sensor spacing, and alignment of sensors between layers enhances both the detection of magnetic field signals from the target organ and allows for the application of signal processing techniques to reduce/remove signals from interference sources. Accordingly, the combination of features enables the disclosed device and system to be operable without magnetic shielding. Additionally, the disclosed device and system are operable without cryogenic cooling (e.g., at room temperature or ambient operating temperature). This combination of features differentiates the disclosed device and system from, and improves over, existing MCG systems.

The disclosed MCG device (and system) has several advantages compared to other commercially available devices. First, the disclosed device and system is operable at room temperature (e.g., ambient temperature), in a magnetically unshielded environment, thus reducing operating costs and improving usability. Second, the disclosed device utilizes magnetometers that allow further opportunities for device miniaturization and/or portability.

The systems, methods, and devices of this disclosure each have several innovative aspects, no single one of which is solely responsible for the desirable attributes disclosed herein.

In accordance with some embodiments, an apparatus for measuring magnetic fields from a subject's organ comprises a plurality of magnetometers in a three-dimensional arrangement. A respective pair of magnetometers, in the plurality of magnetometers, has a respective known distance. Each magnetometer, in the plurality of magnetometers, is configured to simultaneously detect a biomagnetic field from at least a portion of the subject's organ and a background magnetic field and output a signal indicative of the detected biomagnetic field and the background magnetic field. The apparatus is configured to operate without magnetic shielding. In some embodiments, the background magnetic field includes the earth's magnetic field. In some embodiments, the background magnetic field includes magnetic fields that are generated by one or more devices distinct from the apparatus and in proximity to the apparatus (e.g., within 0.5 m, 1 m, or 2 m of the apparatus).

In some embodiments, each magnetometer in the plurality of magnetometers is responsive to a total magnetic field in proximity to the respective magnetometer.

In some embodiments, the respective known separation has a respective fixed length.

In some embodiments, the plurality of magnetometers includes a first magnetometer having a variable position. A respective pair of magnetometers, in the plurality of magnetometers, has a respective known separation that varies during device operation and determined by tracking a position of the first magnetometer.

In some embodiments, the background magnetic field includes a uniform magnetic field. In some instances, the uniform magnetic field is from the earth.

In some embodiments, the plurality of magnetometers has an average spacing that satisfies a constraint in Fourier space. In some embodiments, the average spacing provides a wavevector coverage to recover information from both the biomagnetic field from the subject's organ and the background magnetic field.

In some embodiments, the plurality of magnetometers are spatially distributed such that in Fourier space, the plurality of magnetometers have a wavevector coverage to recover information from both the biomagnetic field from the subject's organ and the background magnetic field.

In some embodiments, the plurality of magnetometers comprises an array of magnetometers arranged in a stack of planes. Adjacent magnetometers in a respective plane of the stack of planes are separated by a first predefined spacing along a length of the array and separated by a second predefined spacing along a width of the array. Magnetometers in adjacent planes of the stack of planes are separated by a third predefined spacing along a thickness direction of the array.

In some embodiments, a first magnetometer in a first plane of the stack of planes is aligned with a second magnetometer in a second plane of the stack of planes along the length and the width of the array.

In some embodiments, the array of magnetometers includes a first subset of magnetometers positioned in a first plane of the stack of planes and a second subset of magnetometers positioned in a second plane of the stack of planes. The first subset of magnetometers is aligned with the second subset of magnetometers along the length and the width of the array.

In some embodiments, each of the magnetometers in the array comprises an optically pumped magnetometer (OPM).

In some embodiments, each of the magnetometers in the array comprises a diamond nitrogen-vacancy (NV) center sensor.

In some embodiments, each of the magnetometers in the array comprises a fluxgate sensor.

In some embodiments, a first subset of magnetometers in the array comprises optically pumped magnetometers. A second subset of magnetometers in the array comprises diamond NV center sensors.

In some embodiments, a first subset of magnetometers in the array comprises optically pumped magnetometers. A second subset of magnetometers in the array comprises fluxgate sensors.

In some embodiments, a first subset of magnetometers in the array comprises diamond NV center sensors. A second subset of magnetometers in the array comprises fluxgate sensors.

In some embodiments, a first subset of magnetometers in the array comprises optically pumped magnetometers, a second subset of magnetometers in the array comprises diamond NV center sensors, and a second subset of magnetometers in the array comprises fluxgate sensors.

In some embodiments, during operation of the apparatus, a distance between the apparatus and the subject is 0.1-5 cm.

In some embodiments, the apparatus is operable at room temperature.

In some embodiments, the apparatus is operable without magnetic shielding.

In some embodiments, each magnetometer in the array of magnetometers has a sensitivity better than 100 pT/$\sqrt{\text{Hz}}$. In some embodiments, each magnetometer in the array of magnetometers has a sensitivity better than 10 pT/$\sqrt{\text{Hz}}$, or more specifically from 0.1-10 pT/$\sqrt{\text{Hz}}$.

In some embodiments, each magnetometer in the array of magnetometers has a sufficient dynamic range (e.g., 50 μT, 100 μT, 150 μT, or 200 μT) to capture both the MCG signals from the heart as well as signals from the earth's magnetic field.

In some embodiments, the first predefined spacing has a range from 0.5 cm to 2 cm.

In some embodiments, the second predefined spacing has a range from 0.5 cm to 2 cm.

In some embodiments, the third predefined spacing has a range from 0.5 cm to 2 cm.

In some embodiments, adjacent magnetometers in a respective plane of the stack of planes have a pitch of 1.5 cm to 3.5 cm along the length of the array.

In some embodiments, adjacent magnetometers in a respective plane of the stack of planes have a pitch of 1.5 cm to 3.5 cm along the width of the array.

In some embodiments, each magnetometer of the plurality of unshielded magnetometers has a dynamic range of around 50 microTeslas.

In some embodiments, each magnetometer of the plurality of unshielded magnetometers has a dynamic range of around 100 microTeslas.

In accordance with some embodiments, an unshielded magnetometer system for measuring magnetic fields from a subject's organ includes a plurality of magnetometers in a three-dimensional arrangement. A respective pair of magnetometers, in the plurality of magnetometers, has a respective known separation. Each magnetometer in the plurality of magnetometers is configured to simultaneously detect a biomagnetic field from at least a portion of the subject's organ and a background magnetic field and output a signal indicative of the detected biomagnetic field and the background magnetic field. The unshielded magnetometer system includes one or more processors and memory. The memory stores instructions for execution by the one or more processors. The stored instructions include instructions for causing each magnetometer in the plurality of magnetometers to: (i) simultaneously measure a biomagnetic field from at least a portion of the subject's organ and a background magnetic field; and (ii) output a signal indicative of the detected biomagnetic field and the background magnetic signal. The magnetometer system is configured to operate without magnetic shielding.

In some embodiments, the stored instructions include signal processing instructions to separate the background field from the biomagnetic signals.

In some embodiments, the plurality of magnetometers are positioned within a housing.

In some embodiments, the magnetometer system includes a positioning arm for supporting the plurality of unshielded magnetometers. In some instances, the positioning arm is mounted on a base that includes one or more wheels. In some instances, the positioning arm is mounted on a patient support platform.

In some embodiments, the magnetometer system includes a panel for mounting the plurality of unshielded magnetometers. The panel is supported by the positioning arm.

In some instances, the positioning arm is configured to maintain a gap of 0.5 cm to 5 cm between the panel and a chest of the subject during an entire patient scan.

In some instances, the positioning arm includes one or more lockable moving degrees of freedom.

In some instances, the positioning arm includes three coupled degrees of freedom (DOF).

In accordance with some embodiments, a method for determining magnetic fields from an organ of a human subject is performed at a computer system. The computer system includes one or more processors and memory. The method includes receiving a plurality of signals corresponding to first time-series magnetic data generated from a plurality of unshielded magnetometers proximate to the human subject. The first time-series magnetic data corresponds to magnetic fields generated from the human subject. The first time-series magnetic data additionally contains environmental magnetic interference. The plurality of signals includes contributions from a biomagnetic field from at least a portion of the subject's organ and a background magnetic field. The method includes synchronizing the first time-series magnetic data to a common clock to generate synchronized time-series magnetic data. The method includes applying one or more filters to the synchronized time-series magnetic data to obtain filtered data. The method includes applying one or more noise reduction techniques to the filtered data to generate updated time-series magnetic data.

In some embodiments, applying one or more filters to the synchronized time-series magnetic data comprises applying a notch filter having a frequency of an electrical line noise (e.g., a frequency of a power source) (e.g., 60 Hz in the United States, 50 Hz in Europe or Asia).

In some embodiments, applying one or more filters to the synchronized time-series magnetic data comprises applying a bandpass filter.

In some embodiments, the bandpass filter includes a frequency range of 0.5 Hz to 40 Hz.

In some embodiments, the plurality of magnetometers is an m×n array of magnetometers arranged in a stack of p planes. m is a number of magnetometers in a length direction of the array, n is a number of magnetometers in a width direction of the array, and p is a number of planes, in the stack of planes, arranged in a height direction of the array.

In some embodiments, the stack of p planes includes a first plane and a second plane that is adjacent to the first plane. Applying one or more noise reduction techniques to the filtered data includes obtaining positional information corresponding to each magnetometer in the array of magnetometers. The method includes, for a respective pair of magnetometers, in the array of magnetometers, consisting of a respective first magnetometer positioned in the first plane and a respective second magnetometer positioned in the second plane, calculating a difference between a first filtered signal corresponding to the respective first magnetometer and a second filtered signal corresponding to the second respective magnetometer. The respective first magnetometer and the second respective magnetometer are aligned with respect to each other in the length direction and the width direction.

In some embodiments, calculating the difference between the first filtered signal corresponding to the respective first magnetometer and the second filtered signal corresponding to the second respective magnetometer further includes determining a correlation between the first filtered signal and the second filtered signal using linear regression; and calculating the difference according to the determined correlation.

In some embodiments, applying one or more noise reduction techniques to the filtered data includes applying principal component analysis (PCA) to extract, from the filtered data, a subset of variables from all variables of the filtered data.

In some embodiments, applying PCA includes determining a plurality of principal components (PCs) corresponding to the filtered data; and assigning a value of zero to a subset of the plurality of PCs, thereby removing one or more noise contributions from the filtered data.

In some embodiments, applying one or more noise reduction techniques to the filtered data includes applying signal source separation (SSS) to the filtered data.

In some embodiments, the synchronized time-series magnetic data comprises magnetic data that are recorded over a plurality of events. The method further includes, for a respective magnetometer of the array of magnetometers, aligning a respective subset of the synchronized time-series magnetic data corresponding to the respective magnetometer over the plurality of events based on a trigger signal to generate a respective subset of aligned signals; and combining the respective aligned subset of the synchronized time-series magnetic data over the plurality of events.

In some embodiments, the method further includes obtaining positional information corresponding to each magnetometer in the plurality of magnetometers; and correlating a respective signal of the plurality of signals to the obtained positional information.

In some embodiments, the updated time-series magnetic data includes a plurality of updated signals corresponding to respective magnetometers in the array of magnetometers. The method includes obtaining positional information corresponding to each magnetometer in the array of magnetometers; correlating a respective updated signal of the plurality of updated signals to a respective magnetometer based on the obtained positional information; generating a magnetic field map that spatially correlates a magnetic field distribution of the organ of the human subject with the positional information of each magnetometer in the array of magnetometers; and causing display of the magnetic field map on a display device.

In some embodiments, the plurality of magnetometers comprises a plurality of vector magnetometers. The method further includes, after receiving the plurality of signals, corresponding to vector field signals from the plurality of vector magnetometers, calibrating and processing the plurality of signals according to physical sensor orientation to obtain the first time-series magnetic data.

In accordance with some embodiments, a computer system includes one or more processors and memory. The memory stores one or more programs configured for execution by the computer system. The one or more programs include instructions for performing any of the methods described herein.

In accordance with some embodiments, a non-transitory computer-readable storage medium stores one or more programs configured for execution by a computer system having one or more processors and memory. The one or more programs include instructions for performing any of the methods described herein.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 14A to 14D provide a flowchart of a method for determining magnetic fields from an organ of a human subject, in accordance with some embodiments.

Reference will now be made to embodiments, examples of which are illustrated in the accompanying drawings. In the following description, numerous specific details are set forth in order to provide a thorough understanding of the present invention. However, it will be apparent to one of ordinary skill in the art that the present invention may be practiced without requiring these specific details.

DETAILED DESCRIPTION

Some methods, devices, and systems disclosed in the present specification advantageously improve upon existing devices for bio-imaging, by providing a device and/or system that combines hardware components and signal processing techniques for resolving magnetic fields from a target organ of a human subject. In this disclosure, the terms "human subject" and "patient" are used interchangeably.

In accordance with some embodiments disclosed herein, a novel MCG system is built around an array of unshielded, scalar, optically pumped magnetometers (OPMs) that effectively rejects ambient magnetic interference without environmental magnetic shielding.

Figure 1A:
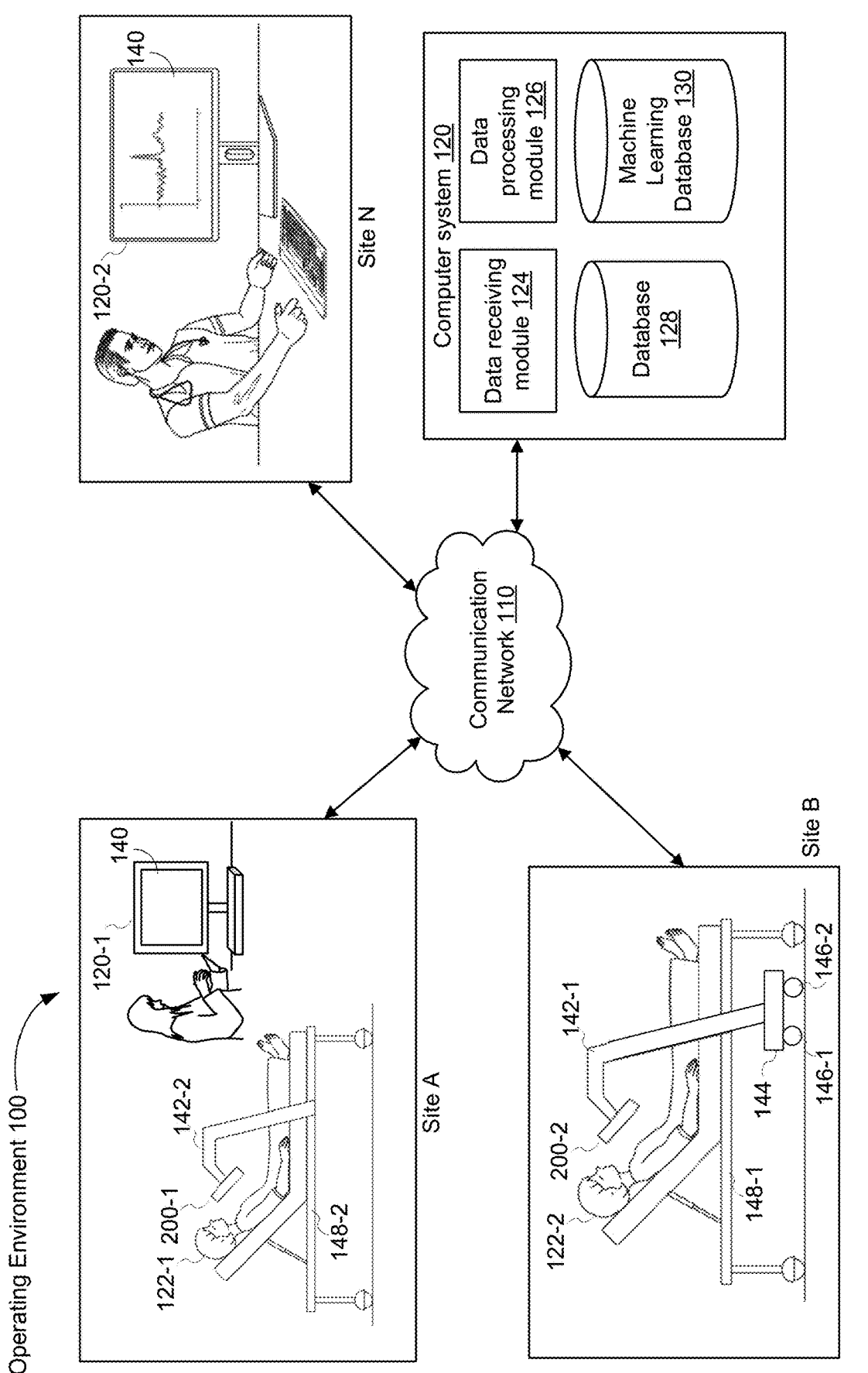
FIG. 1A illustrates an operating environment in accordance with some embodiments.

FIG. 1A illustrates an exemplary operating environment 100 in accordance with some embodiments. In some embodiments, the operating environment 100 includes one or more devices 200. In some embodiments, the device 200 is an MCG device for measuring magnetic signals from the heart of a human subject. In some embodiments, the device 200 is a MEG device for measuring magnetic signals from the brain of a human subject. In the example of FIG. 1A, each of the devices 200 (e.g., device 200-1 and device 200-2) is located at a respective (e.g., distinct) site (e.g., Site A and Site B), corresponding to a respective (e.g., distinct) city, state, or country. In some embodiments, a site corresponds to a hospital, a clinic, or a medical facility.

In some embodiments, the device 200 (e.g., an apparatus) is communicatively coupled through communication network(s) 110 to a computer system 120. In some embodiments, the computer system 120 and the device 200 are co-located at the same location (e.g., in the same room where the device 200 is employed). For example, FIG. 1A shows that the device 200-1 and the computer system 120-1 are located in Site A (e.g., different rooms of the same hospital, or within the same room in a hospital). In some embodiments, the device 200 and the computer system 120 are located at different locations. For example, FIG. 1A shows that the device 200-2 is located at site B whereas the computer device 120-2 is located at site N. In some embodiments, the computer system is a system that is located on the cloud.

As disclosed herein, the device 200 includes one or more magnetometers 201 that are configured to measure (e.g., sense, acquire, collect, obtain, etc.) magnetic field signals from a target organ of a human subject 122 while the device 200 is operating in a magnetically unshielded environment. In some embodiments, the magnetic field signal is a magnetic flux density. In some embodiments, the measured signals are transmitted to the computing system 120 for post-processing. In some embodiments, the data (e.g., actual data or post-processed data) is caused to be displayed on the computer system 120, or on a display device 140 that is communicatively connected to the computer system 120.

In some embodiments, the device 200 is a part of a self-contained device/system that also includes sensors (e.g., magnetometers 201, and optionally, sensors of different sensor types, such as light sensors, motion sensors, etc.), one or more positioning arms (e.g., mechanical positioning arm) (e.g., positioning arm 142-1 or positioning arm 142-2, FIG. 1A), a computer (e.g., computer system 120, display device 140, etc.), and power supply with backup. In some embodiments, the magnetometers 201 are positioned (e.g., stored) in a housing 143. The housing 143 can be easily sterilized to allow for repeated use in different environments. In some embodiments, the device 200 is constructed of non-magnetic materials, and is robust to vibrations.

In some embodiments, the self-contained device/system 200 is a portable, mobile device/system that is configured to be movable within the operating environment 100. For example, FIG. 1A illustrates that, in some embodiments, the device/system 200 includes a standalone positioning arm 142-1 mounted on a base 144 that includes one or more wheels 146 (e.g., wheel 146-1 and 146-2), for moving the device/system 200 between different examination rooms within the operating environment 100. The device/system 200 can be positioned next to a patient lying on a patient support platform 148-1 or next to a patient sitting on a chair. FIG. 1A also illustrates that, in some embodiments, the device/system 200 includes a positioning arm 142-2 that can be directly mounted on a patient support platform 148-2. The device/system 200 is designed such that it can acquire data (e.g., imaging data, scan data, etc.) from the patient without requiring the patient to relocate from their present position, thereby minimizing disruptions to the critical care workflow.

As disclosed, the device/system 200 is easier to maneuver compared to existing MCG or MEG systems that require shielding and/or operate under cryogenic conditions. The portable nature of device/system 200, coupled with its ability to operate without environmental magnetic shielding, makes it a suitable candidate for use in external environments including in military settings, unconventional settings, outside a medical/hospital setting, and in impoverished areas with limited infrastructure.

In some embodiments, the apparatus 200 includes a panel (e.g., rigid panel) on (or within) which the magnetometers 201 are mounted. The magnetometers 201 are modular in nature and can be replaced and/or swapped out in case one or more fail. During device operation, the panel maintains a fixed position relative to the patient. For example, when the apparatus 200 is a MCG device, the apparatus 200 (e.g., the panel including the magnetometers 201) can maintain a position with a 0.5 cm to 5 cm parallel gap to the patient's chest during an entire patient scan, with minimal vibration (e.g., no vibration) and/or minimal slippage (e.g., no slippage, slippage/movement no greater than 1 mm, etc.) during the scan. In some embodiments, the device stability is assisted by locking out unnecessary mechanical degrees of freedom (DOF) (e.g., no rotation around the y-axis and/or z-axis).

Further elaborating on the implementation in which the apparatus 200 is a MCG device, in some embodiments, with the base of the apparatus 200 stabilized with respect to the floor and parallel to a patient's sagittal plane, an operator can easily and conveniently (e.g., within seconds of manual or automatic actuation) maneuver the positioning arm 142 (e.g., positioning arm 142-1) to bring the sensor panel substantially close to, and parallel with, the patient's chest. In some embodiments, the apparatus 200 enables easy and accurate positioning of the panel such that it is positioned substantially centered over a heart of the patient. For example, in some embodiments, the apparatus 200 enables fiducial registration to standard anatomical landmarks to enable data consistency between patients.

In some embodiments, the positioning arm 142 (e.g., positioning arm 142-1 or 142-2) includes lockable moving degrees of freedom (DOF) (e.g., three coupled DOF, namely: sliding along the y-axis, and a double-jointed pivot allowing coarse rotation around the x-axis followed by fine rotation around the x-axis).

In some embodiments, the device/system 200 is configured to acquire a biomagnetic field scan of a patient and provide information about potential disease states, such as coronary artery diseases, ischemia, and arrhythmias in patients (including adults, children, and fetuses). In some embodiments, the patient scan and diagnosis are provided during the same patient visit. For example, in some embodiments, the device/system 200 is configured to acquire a biomagnetic field scan of a patient within one to two minutes of scan initiation. In some embodiments, the device/system 200 is configured to process the scan data locally (e.g., in real time), or transmit the scan data to the cloud for processing (e.g., in real time). In some embodiments, care-informing results are returned (e.g., by the computer system 120) to the operator within two to five minutes after that.

In the example of FIG. 1A, the computer system 120 includes a data receiving module 124 that is configured to receive data from one or more devices 200. In some embodiments, the data corresponds to magnetic field data that is generated (e.g., measured, collected, acquired) from respective magnetometers 201 of a device 200. The computer system 120 includes a data processing module 126 that is configured to process the received data. Further details of the data processing process are described with respect to FIGS. 5 to 11.

In some embodiments, the computer system 120 includes a database 128. Details of the database 128 are described with respect to FIG. 3.

In some embodiments, the computer system 120 includes a machine learning database 130 that stores machine learning information. In some embodiments, the machine learning database 130 is a distributed database. In some embodiments, the machine learning database 130 includes a deep neural network database. In some embodiments, the machine learning database 130 includes supervised training and/or reinforcement training databases.

Figure 1B:
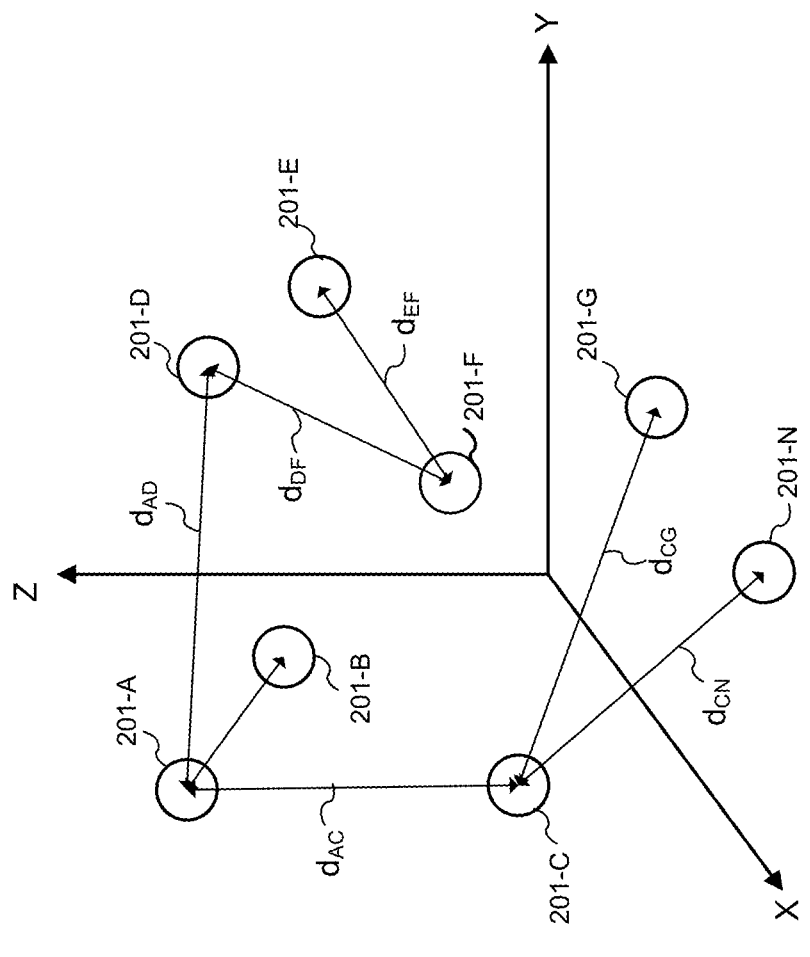
FIG. 1B illustrates an apparatus for measuring magnetic fields from a subject's organ in accordance with some embodiments.

FIG. 1B illustrates an apparatus 200 for measuring magnetic fields from a subject's organ in accordance with some embodiments. In this example, the apparatus 200 occupies a three-dimensional space that is defined by three orthogonal axes (x-, y-, and z-axes). The apparatus 200 includes a plurality of magnetometers 201 (e.g., magnetometer 201-A to magnetometer 201-N). Each of the magnetometers 201 occupies a respective position in the three-dimensional space of the apparatus 200, with respective x-, y-, and z-coordinates. A respective pair of magnetometers 201-$i$ and 201-$j$, in the plurality of magnetometers 201, is separated by a respective distance dij. For example, FIG. 1B shows that the pair of magnetometers 201-E and 201-F is separated by a distance der, and the pair of magnetometers 201-C and 201-N is separated by a distance $d_{CN}$. Each magnetometer in the plurality of magnetometers 201 is configured to simultaneously detect a biomagnetic field from at least a portion of the subject's organ and a background magnetic field.

In some embodiments, each of the magnetometers has a fixed (e.g., rigid) position in the apparatus 200. A respective pair of magnetometers 201-$i$ and 201-$j$, in the plurality of magnetometers 201, is separated by a respective fixed distance dij.

In some embodiments, the apparatus 200 can include at least one magnetometer 201 whose position is variable (e.g., continuously variable). The positions of the magnetometers can be tracked during device operation.

In some embodiments, each of the magnetometers 201 in the apparatus 200 is responsive to a total magnetic field in proximity to the magnetometer 201. During device operation, the magnetometers 201 detect biomagnetic fields from a subject's organ as well as background magnetic field (e.g., from the earth and/or other interference sources). In some embodiments, the magnetometer 201 is a scalar magnetometer that measures the total strength of the magnetic field to which it is subjected (e.g., including the Earth's magnetic field), but not the direction.

In some embodiments, each magnetometer in the array of magnetometers has a sufficient dynamic range (e.g., 50 μT, 100 μT, 150 μT, 200 μT, or over 200 μT) to capture both the MCG signals from the heart as well as signals from the earth's magnetic field.

In some embodiments, the magnetometer 201 is a vector magnetometer that is capable of measuring the components of the magnetic field in a particular direction, relative to the spatial orientation of the magnetometer.

In some embodiments, the magnetometers 201 in the apparatus have an average spacing that satisfies a constraint in Fourier space. For example, in some embodiments, the average magnetometer spacing is determined by the Nyquist sampling rate in Fourier space of the wavevectors of the target organ's magnetic field. In some embodiments, the magnetometers 201 are spatially distributed in (e.g., within) the apparatus 200 such that in Fourier space, the magnetometers 201 have a wavevector coverage to recover information from both the biomagnetic field from the subject's organ and the background magnetic field.

There are formidable technical challenges for developing a non-magnetically shielded (i.e., magnetically unshielded), movable, MCG device that can reject ambient/environmental noise, and provide clinically actionable magnetic field images of disease-state effects. Transient human cardiac signals are $10^5$-$10^6$ times smaller than background interference, so to detect heartbeat signals in an unshielded environment, magnetometers must have both large dynamic range and excellent sensitivity. Acquiring clear magnetic field images across the torso further requires the sensors to also exhibit high accuracy exceeding one part in $10^7$, so that tiny differences in magnetic field readings across the chest are properly ascribed to cardiac activity rather than sensor inaccuracy.

Table 1 compares candidate sensor types with which MCG recordings have been demonstrated. Point-of-care infrastructure cost is defined as the monetary and practical cost to install and maintain infrastructure associated with a sensing technology. For example, cryogenics or magnetically shielded enclosures incur high capital costs to a hospital or clinic, as well as high space and logistical costs within a patient's care pathway if they must transfer outside the emergency department for care. Practical demonstration of clinical utility refers to literature-supported demonstrations of disease classification at or exceeding sensitivity and specificity of the standard of care.

TABLE 1

| Comparison of MCG sensor technologies and readiness for clinical adoption. | | |
|---|---|---|
| MCG Sensor Technology | Point-of-Care Infrastructure Cost (Primary Cost Driver) | Practical Demonstration of Clinical Utility |
| SQUIDs | High (inherent cost + cryogenics) | Yes |

TABLE 1-continued

Comparison of MCG sensor technologies
and readiness for clinical adoption.

| MCG Sensor Technology | Point-of-Care Infrastructure Cost (Primary Cost Driver) | Practical Demonstration of Clinical Utility |
|---|---|---|
| SERF OPM | High (multi-layer magnetic shielding) | Yes |
| Inductive coils | Low (system integration) | More Studies Needed |
| Fluxgate | Low (system integration) | No |
| TMR | Low (system integration) | No |
| Scalar OPM | Low (sensor) | No |

Table 1 shows that clinically actionable magnetic field images of cardiac disease-state effects have only been demonstrated with sensor technologies that incur high monetary and practical costs associated with cryogenics and/or magnetically shielded environments. These challenges have limited the widespread adoption of MCG in bedside settings.

The majority of clinical MCG research is performed using SQUID-based MCG systems, due to their extreme magnetic sensitivity and small voxel size. SQUID arrays were used in early demonstrations of MCG imaging for detecting cardiac pathologies. Unfortunately, these high-performance systems incur high costs due to the need for cryogenic cooling and large hospital footprints. Compact, spin-exchange relaxation-free (SERF) optically pumped magnetometers (OPMs) have shown clinical utility for collecting MCG data and can operate without cryogenics. However, SERF OPMs also incur high costs because they must be operated in large, room-scale magnetic shields to eliminate environmental background fields, including Earth's magnetic field and ambient power line noise. Inductive coil sensors, which are sensitive to the time derivative of magnetic fields, have been employed for recordings of MCG, however more studies are required to determine clinical utility. Other types of commercially available magnetometers, including fluxgate and tunneling magnetoresistance (TMR) sensors, are low-cost and can operate without shielding and cryogenics. However, demonstrations of sensitivity required for MCG have been limited to proof-of-concept experiments.

Figure 2:
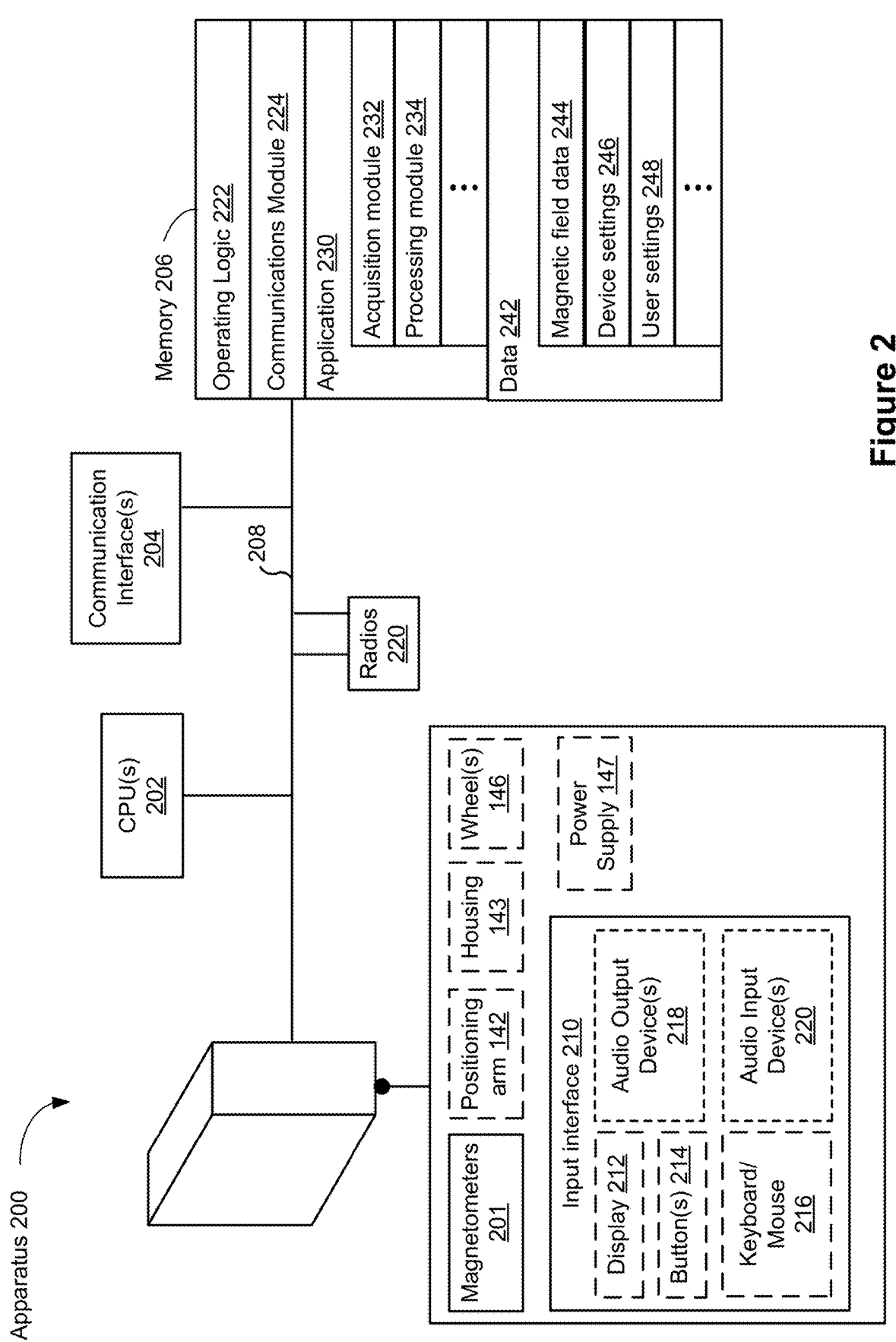
FIG. 2 illustrates a block diagram of a device for measuring magnetic fields of a target organ of a human subject according to some embodiments.

FIG. 2 shows a block diagram of a device 200 (e.g., an apparatus) for measuring magnetic fields of a target organ of a human subject according to some embodiments.

The device 200 includes one or more magnetometers 201 (e.g., a magnetic field sensor).

In some embodiments, the magnetometer 201 comprises an electron spin defect based magnetometer, such as a diamond nitrogen vacancy (NV) center magnetometer (e.g., a solid state sensor). A diamond NV center magnetometer is a quantum sensor that leverages the occurrence of an electronic spin defect in a solid state lattice, where the spin can be both initialized and read out optically or electronically. In some instances, the defect may arise as an atomic-level vacancy in a lattice structure, such as a vacancy occurring near a nitrogen atom that is substituted in place of a carbon atom within diamond.

In some embodiments, the magnetometer 201 comprises an optically pumped magnetometer (OPM) (e.g., a vapor cell sensor). An OPM is a quantum sensor that includes a heated alkali vapor (including, and not limited to, a caesium vapor or a potassium vapor), through which a laser beam passes through. Due to the quantum properties of the atoms, the amount of light passing through the atomic vapor is modulated at a frequency that is proportional to the environmental magnetic field.

In some embodiments, the magnetometer 201 comprises a scalar OPM. Scalar OPMs are highly sensitive to weak magnetic fields, have a large dynamic range (e.g., 50 $\mu$T or more), and do not require magnetic shielding or cryogenics for operation. Further, commercially available scalar OPMs are compact, lightweight, and have low power consumption, making them ideal for integration into a bedside medical device. Given the orders of magnitude separating the strength of geomagnetic fields (~$10^{-6}$ T) and cardiac fields (max ~100 pT), scalar OPMs are sensitive only to those components of the cardiac magnetic field aligned to the total magnetic field vector, which in an unshielded environment is comprised primarily of the Earth's geomagnetic field.

In accordance with some embodiments disclosed herein, the combination of excellent sensitivity, large dynamic range, high accuracy, and technical maturity make scalar OPMs especially promising for integration into a multi-channel, high-resolution MCG device. In some embodiments, the scalar OPM comprises a total-field OPM that can operate in the Earth's field.

In some embodiments, the magnetometer 201 comprises a fluxgate sensor.

In some embodiments, the magnetometer 201 is responsive to a total magnetic field proximate to the magnetometer 201. During device operation, the magnetometer detects a total magnetic field, including biomagnetic fields from a subject's organ as well as background magnetic field (e.g., from the earth, other equipment in the vicinity of the total magnetometer etc.). In some embodiments, the magnetometer 201 is a scalar magnetometer that measures the total strength of the magnetic field to which it is subjected, but not the direction.

In some embodiments, the magnetometer 201 is a vector magnetometer that is capable of measuring both the magnitude of the magnetic field as well as the respective field direction(s). In this case, the total strength of the magnetic field can be obtained by calibrating and processing the plurality of signals according to physical sensor orientation (e.g., computing a dot product of the vector components).

In some embodiments, the use of vector magnetometers as magnetometer 201 can enable new capabilities of the device 200. Cardiac magnetic signals are directional by nature. Using vector magnetometers enables the axial components (e.g., x-, y-, and z-components) to be fully resolved, thereby leading to higher information density and boosting source reconstruction methods. Decomposing the noise according to vector sensor axes can also improve the noise rejection algorithms. In some embodiments, sensor calibration methods are provided with the vector magnetometers. For example, the vector magnetometers can be calibrated periodically, or before the use of the device 200, to ensure that orthogonality between sensors is maintained high performance gradiometry noise subtraction can be achieved.

In some embodiments, the one or more magnetometers 201 comprise at least two magnetometers that are arranged in an array. In some embodiments, the array of magnetometers is arranged in a stack of planes. Further details of the magnetometer array are described in FIGS. 4A to 4D.

In some embodiments, the device 200 includes a positioning arm 142, as described with respect to FIG. 1A. In some embodiments, the device 200 includes a housing 143 (see, e.g., housing 251, FIG. 4F). In some embodiments, the device 200 includes one or more wheels 146 for supporting the device 200 (and the positioning arm 142), as described with respect to FIG. 1A.

In some embodiments, the device 200 is coupled to a power supply 147. In some embodiments, the power supply 147 is an external power supply. In some embodiments, the powers supply 147 is a battery pack that ensures backup power for safeguarding data and/or protecting device 200 in case of a power outage. In some embodiments, the battery pack facilitates movement of the device 200 between rooms without having to power down the device 200.

In some embodiments, the device 200 includes an input interface 210 for facilitating user input, such as a display 212, button(s) 214, a keyboard and/or mouse 216.

In some embodiments, input interface 210 includes a display device 212. In some embodiments, the device 200 includes input devices such as button(s) 214, and/or a keyboard/mouse 216. Alternatively or in addition, in some embodiments, the display device 212 includes a touch-sensitive surface, in which case the display device 212 is a touch-sensitive display. In some embodiments, the touch-sensitive surface is configured to detect various swipe gestures (e.g., continuous gestures in vertical and/or horizontal directions) and/or other gestures (e.g., single/double tap). In computing devices that have a touch-sensitive display, a physical keyboard is optional (e.g., a soft keyboard may be displayed when keyboard entry is needed). The input interface 210 also includes an audio output device 218, such as speakers or an audio output connection connected to speakers, earphones, or headphones. In some embodiments, the apparatus 200 includes an audio input device 220 (e.g., a microphone) to capture audio (e.g., speech from a user). In some embodiments, the device 200 uses a microphone and voice recognition to supplement or replace the keyboard.

The device 200 also includes one or more processors (e.g., CPU(s)) 202, one or more communication interface(s) 204 (e.g., network interface(s)), memory 206, and one or more communication buses 208 for interconnecting these components (sometimes called a chipset).

In some embodiments, the device 200 includes radios 220. The radios 220 enable one or more communication networks, and allow the device 200 to communicate with other devices, such as a computer system (e.g., the computing system 120 in FIGS. 1 and 3) or a server. In some embodiments, the radios 220 are capable of data communication using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, Ultrawide Band (UWB), and/or software defined radio (SDR)) custom or standard wired protocols (e.g., Ethernet or HomePlug), and/or any other suitable communication protocol, including communication protocols not yet developed as of the filing date of this patent application.

The memory 206 includes high-speed random access memory, such as DRAM, SRAM, DDR RAM, or other random access solid state memory devices. In some embodiments, the memory includes non-volatile memory, such as one or more magnetic disk storage devices, one or more optical disk storage devices, one or more flash memory devices, or one or more other non-volatile solid state storage devices. In some embodiments, the memory 206 includes one or more storage devices remotely located from one or more processor(s) 202. The memory 206, or alternatively the non-volatile memory within the memory 206, includes a non-transitory computer-readable storage medium. In some embodiments, the memory 206, or the non-transitory computer-readable storage medium of the memory 206, stores the following programs, modules, and data structures, or a subset or superset thereof:

operating logic 222, including procedures for handling various basic system services and for performing hardware dependent tasks;

a communication module 224 (e.g., a radio communication module), which connects to and communicates with other network devices (e.g., a local network, such as a router that provides Internet connectivity, networked storage devices, network routing devices, server systems, computer system 120, and/or other connected devices) coupled to one or more communication networks via the communication interface(s) 204 (e.g., wired or wireless);

an application 230, which acquires magnetic field data (e.g., via the magnetometers 201) and/or processes the acquired data. In some embodiments, the application 230 controls one or more components of the device 200 and/or other connected devices (e.g., in accordance with the acquired data). In some embodiments, the application 230 includes:

an acquisition module 232, which acquires magnetic data (e.g., magnetic field data) from magnetometers 201. In some embodiments, the magnetic data comprise time-series magnetic data; and a processing module 234, which processes the magnetic field data data 242 for the apparatus 200, including but not limited to:

magnetic field data 244;

device settings 246 for the device 200, such as default options, acquisition settings, and preferred user settings; and user settings 248.

In some embodiments, data collected during the data acquisition process is added as data 242.

Although FIG. 2 shows a device (e.g., an apparatus) 200, FIG. 2 is intended more as a functional description of the various features that may be present rather than as a structural schematic of the embodiments described herein. In practice, and as recognized by those of ordinary skill in the art, items shown separately could be combined and some items could be separated.

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various embodiments. In some embodiments, the memory 206 stores a subset of the modules and data structures identified above. Furthermore, the memory 206 may store additional modules or data structures not described above. In some embodiments, a subset of the programs, modules, and/or data stored in the memory 206 are stored on and/or executed by a server system, and/or by an external device (e.g., computer system 120).

Figure 3:
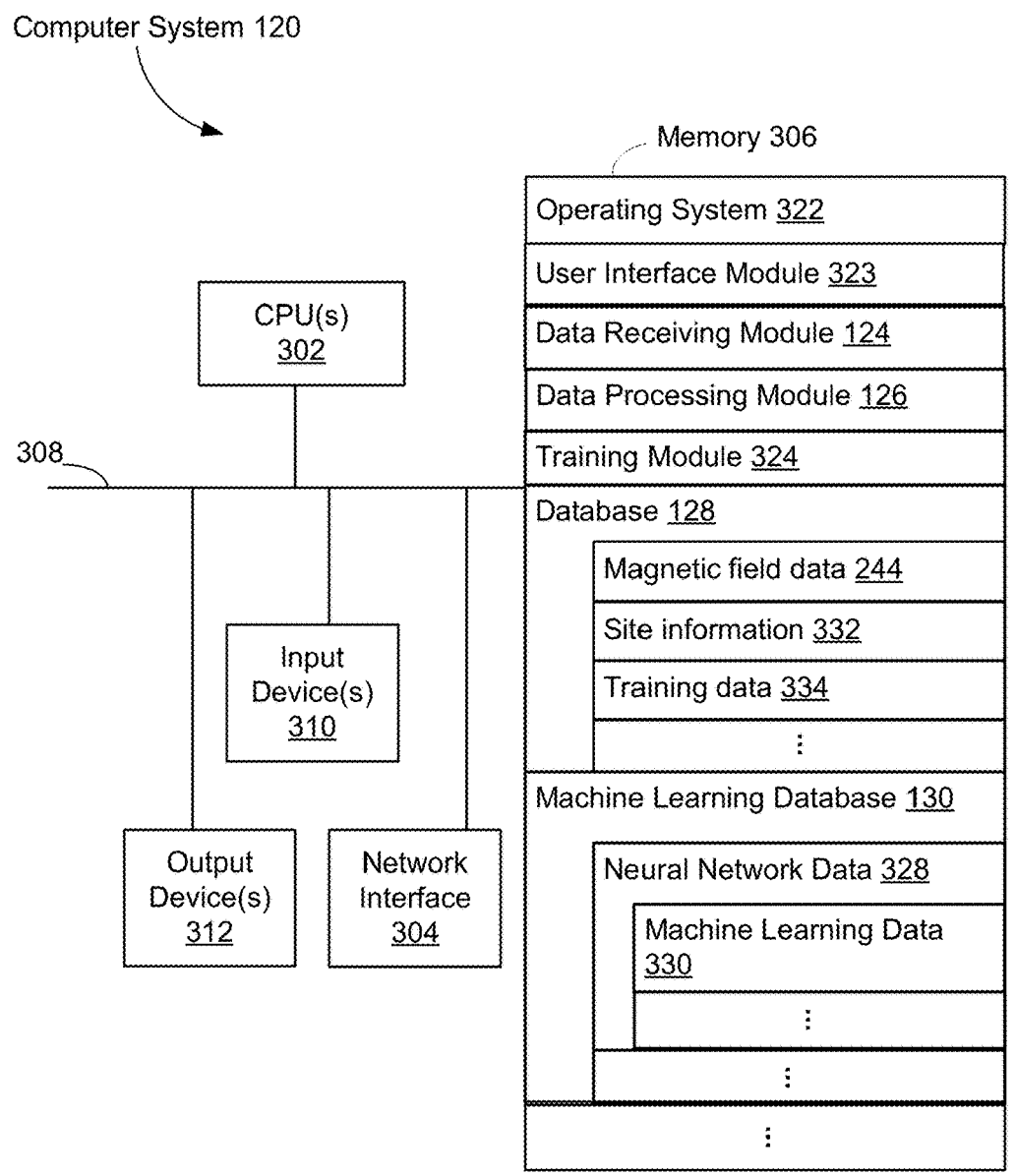
FIG. 3 is a block diagram illustrating a computer system, in accordance with some embodiments.

FIG. 3 is a block diagram illustrating a computer system 120, in accordance with some embodiments.

The computer system 120 includes one or more processors 302 (e.g., processing units of CPU(s)), one or more network interfaces 304, memory 306, and one or more communication buses 308 for interconnecting these components (sometimes called a chipset), in accordance with some embodiments.

The computer system 120 optionally includes one or more input devices 310 that facilitate user input, such as a keyboard, a mouse, a voice-command input unit or microphone, a touch screen display, a touch-sensitive input pad, a gesture capturing camera, or other input buttons or controls. In some embodiments, the computer system 120 optionally uses a microphone and voice recognition or a camera and gesture recognition to supplement or replace the keyboard. The computer system 120 optionally includes one or more output devices 312 that enable presentation of user interfaces and display content, such as one or more speakers and/or one or more visual displays.

The memory 306 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 306, optionally, includes one or more storage devices remotely located from the one or more processors 302. The memory 306, or alternatively the non-volatile memory within the memory 306, includes a non-transitory computer-readable storage medium. In some embodiments, the memory 306, or the non-transitory computer-readable storage medium of the memory 306, stores the following programs, modules, and data structures, or a subset or superset thereof:

an operating system 322 including procedures for handling various basic system services and for performing hardware dependent tasks;

a user interface module 323 for enabling presentation of information (e.g., a graphical user interface for presenting application(s), widgets, websites and web pages thereof, games, audio and/or video content, text, etc.) either at the computer system or at a device, e.g., device 200;

a data receiving module 124 for receiving data (e.g., from device 200);

a data processing module 126 for processing data received by the computer system 120. Further details of data processing are described in FIGS. 5 to 11;

a training module 324 for generating and/or training models, which can be used for identifying and filtering out interference sources to improve the signal-to-noise ratio of magnetic field data, and/or for identifying disease states of the target organ from the magnetic field measurements. In some embodiments, the training module 324 uses training data 334 to generate and/or train the models. In some embodiments, the training data 334 (e.g., training data sets) are generated from measurements from devices 200 (e.g., magnetometers 201). For example, in some embodiments, supervised machine learning is used to aid in denoising and signal and/or feature extraction. In some embodiments, deep learning networks, such as convolutional neural networks (CNNs) or autoencoder networks, are trained on signal components that can be classified as noise or heart-beat signals, and these models can be used to classify signal components in data. Further transformations on training data, which may encompass components derived from PCA or ICA, as well as data augmented with simulated signals or noise, can be used to further refine the models;

a database 128, which store data used, received, and/or created by the computer system 120;

In some embodiments, the memory 306 includes a machine learning database 130 for storing machine learning information. In some embodiments, the machine learning database 130 includes the following datasets or a subset or superset thereof:

neural network data 328 including information corresponding to the operation of one or more neural network(s). In some embodiments, the neural network data 328 includes one or more models that are trained on a combination of realistic physics simulation of magnetic interference sources and real-world data sets. In some embodiments, the models can identify sources of noise and remove them from the magnetic signals. In some embodiments, the models are trained on a combination of time-series and magnetic field map data to classify different cardiac disease states. In some embodiments, the neural network data 328 includes:

training data 330, such as training datasets for training the one or more models to identify differences between disease states (e.g., as labeled by trained professionals). In some embodiments, the training data 330 includes signal data (e.g., from target organs) and noise data.

In some embodiments, the computer system 120 includes a device registration module for registering devices (e.g., computer devices, devices 200, etc.) for use with the computer system 120.

Each of the above identified elements may be stored in one or more of the memory devices described herein, and corresponds to a set of instructions for performing the functions described above. The above identified modules or programs need not be implemented as separate software programs, procedures, modules or data structures, and thus various subsets of these modules may be combined or otherwise re-arranged in various embodiments. In some embodiments, the memory 306, optionally, stores a subset of the modules and data structures identified above. Furthermore, the memory 306 optionally stores additional modules and data structures not described above. In some embodiments, a subset of the programs, modules, and/or data stored in the memory 306 are stored on and/or executed by the device 200.

Device for Measuring Biomagnetic Signals

Design Considerations

For magnetometry applications in unshielded environments, it is desirable to separate out signals originating from the source of interest (signal) from those originating from sources in the environment (noise). Application design can enforce that noise sources will be farther away from the magnetometer array than signal sources, an important distinction that utilizes the fact that magnetic fields decrease in amplitude as distance from the source increases, according to a power law.

Given the above, there are three parameters that can be considered when designing a sensor array—extent, density, and regularity.

Extent refers to the overall scale of the sensor array, that is, the longest distance between two magnetometers. A larger extent enables longer baseline measurements, which allow for discrimination of source of varying distances, e.g., far (e.g., noise) versus near (e.g., signal) sources. In particular, spatial gradient fields across a sensor array with insufficient extent can corrupt signal detection, so larger extent allows for a cleaner separation of signals and noise. For applications in unshielded environments, a minimum array size (e.g., a minimum extent) is necessary so that magnetometer(s) can sample magnetic fields (e.g., magnetic flux densities) from far sources. By contrast, there is no constraint in array size/extent for a sensor array that operates in a magnetically shielded (i.e., noise-free) environment.

Density (or packing density) refers to the number of sensing locations per unit volume, which is determined by the sensor-to-sensor spacing. The minimum density of the array is determined by factors such as size, weight, and power (SWaP) of the respective sensor types, the size and resolution of spatial signal features desired to be captured, and potential cross-talk between sensors. For example, for a cardiac-like current dipole source placed 10 cm below an array, the sensor-to-sensor spacing must be smaller than 10 cm to capture broad features corresponding to the dipole pattern, and must be smaller than 4 cm to resolve source locations with an uncertainty bubble that is smaller than the heart.

Regularity refers to how uniform the sensor arrangement is. Regularity can be determined both by the placement and orientation of the sensors. Regular placement is a matter of convenience, more than anything else. Identical, or regularly varying sensor orientation is easiest for magnetometers that measure vector components of the magnetic field, since field components must be combined later to correctly analyze the field, and irregularities or uncertainties introduced by this variation can affect calibration and spatial field information density. These challenges may be overcome, but solutions may be complicated. For total-field sensors, placement and orientation regularity is inconsequential to signal analysis, which can, in certain cases, allow sensors to be packed more closely together, or in a varying density, if needed. In the case of varying density, one can consider a higher density nearby to the expected source signals, with decreasing density near the outer edges of the array.

Reference sensors (e.g., reference magnetometers) are commonly employed in unshielded applications, to provide Table 2 illustrates the types of sensors that may be included in a bedside MCG system that is operable at room temperature, in a magnetically unshielded environment, with sensitivity of 1 $pT/\sqrt{Hz}$ or better, and potential for scalability (e.g., to include more sensors (e.g., at least 36 sensors) in an array, as more sensors mean better coverage and better noise rejection). This table shows with a "+" advantages/suitability and a "−" disadvantages/insuitability for bedside MCG use with respect to particular sensor attributes.

As shown in Table 2, each sensor type has particular advantages and disadvantages. In some instances, zero-field OPMs are not suitable for use in a non-magnetically shielded environment (i.e., shielding) is required because they have a low dynamic range (e.g., ~10 nT) compared to the other sensor types whose dynamic range are generally about 10,000 times higher. Zero field OPMs require magnetic shielding (active or passive), which precludes their use in a portable/bedside device. SQUIDs require cryogenic cooling, which, considering infrastructure to deliver and maintain, precludes their use in a portable/bedside device. NV diamond sensors have not been demonstrated to achieve the requisite sensitivity below 1 $pT/\sqrt{Hz}$ while also meeting SWAP requirements. The need for high power lasers, microwave electronics, and complex optics have limited the SWaP of high performance NV based magnetometers. Additionally, microwave emission and the common use of flux concentrators (which include permalloy components) induce large crosstalk for proximal sensors in an array. MTJ/TMR sensors also employ flux concentrators, which may affect the crosstalk requirement.

As shown in Table 2, total-field OPM sensors and fluxgate sensors are good candidates for a bedside MCG system as they satisfy all listed attributes (i.e., "+") in all columns.

TABLE 2

| Comparison of Sensor Types for Bedside Magnetocardiography. | | | | | | |
|---|---|---|---|---|---|---|
| Sensor (Magnetometer)Type | SWaP | Sensitivity | Does not require magnetic shielding | Room temperature (no cryogenics) | Low crosstalk | Portable/ Bedside compatible |
| Zero-field OPM | + | + | − | + | + | − |
| Total-field OPM | + | + | + | + | + | + |
| SQUID | + | + | + | − | + | − |
| NV Diamond | − | − | + | + | − | + |
| Fluxgate | + | + | + | + | + | + |
| Magnetic Tunneling Junction (MTJ)/ Tunneling Magnetoresistance (TMR) | + | + | + | + | − | + | a measurement of background/noise fields without signal fields. To do this, a magnetometer is placed at some distance away from the array such that any magnetic fields from the signal source are expected to be smaller than the noise floor of the sensor. For example, cardiac source fields should be well below 1 pT at a distance of around 30 cm from the source. However, noise sources that are 1 m away may be visible on both the array and reference sensors. Therefore, the reference sensors' signals may be used as regressors to the array sensor data. In order to capture highest dimensionality of noise sources, one must place reference sensors along three orthogonal axes at some minimum distance from the array. In a sensor array with large extent, sensors along the edge of the array may be considered as reference sensors.

FIGS. 4A to 4E illustrate an exemplary implementation of the device 200, in which the magnetometers 201 are arranged in an array, in accordance with some embodiments.

Figure 4A:
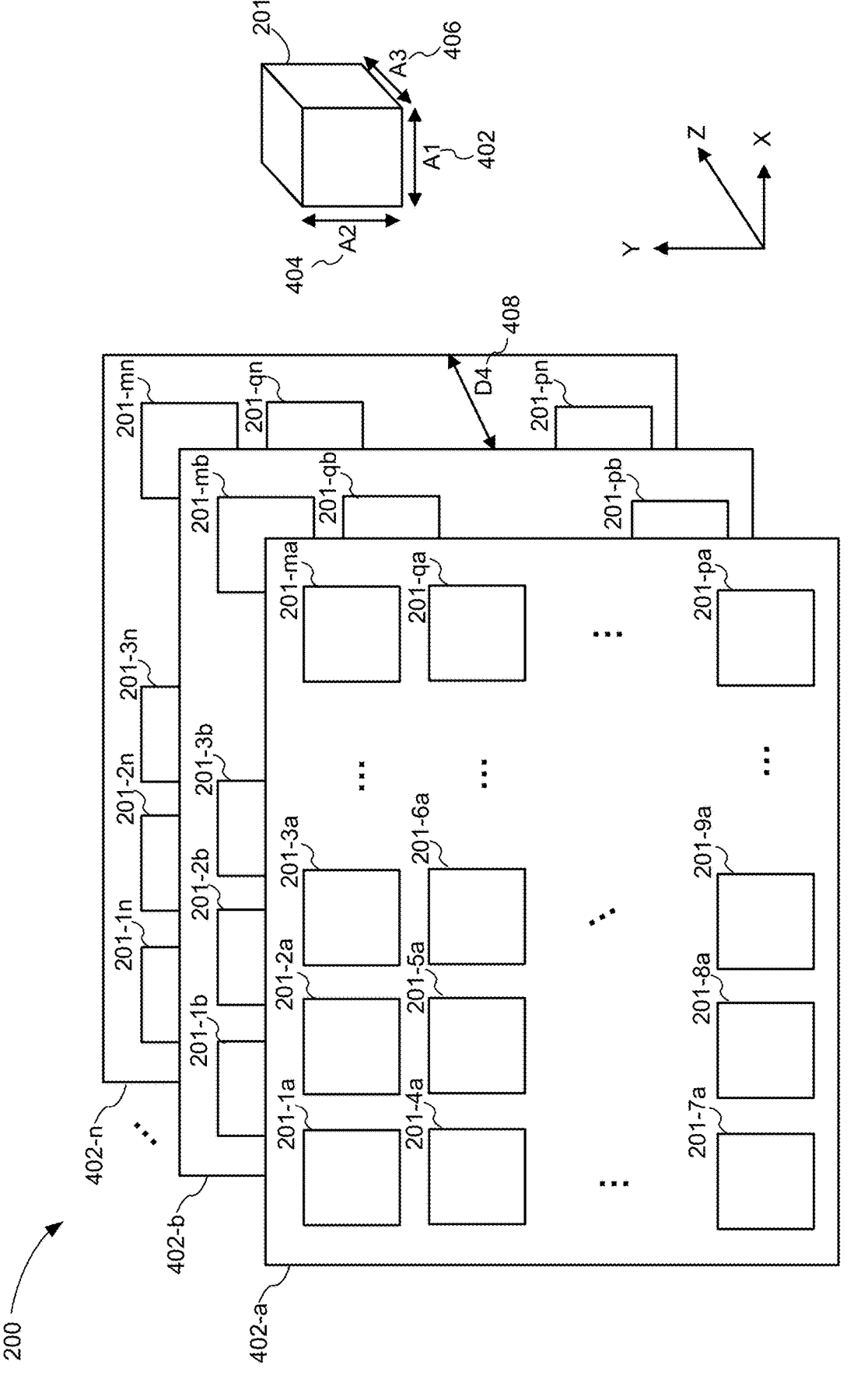
FIGS. 4A to 4G illustrate exemplary embodiments of a device for measuring magnetic fields of a target organ of a human subject in accordance with some embodiments.

FIG. 4A illustrates that the device 200 includes one or more planes 402 (e.g., layers). In some embodiments, the device 200 includes multiple planes (e.g., a plane 402-a, a plane 402-b, and/or a plane 402-n, etc.) (e.g., multiple layers) that are arranged in a stack.

In some embodiments, each plane 402 in the stack of planes has identical dimensions (e.g., the same length, width, and/or thickness).

In some embodiments, the stack of planes includes a first plane and a second plane. The first plane has a different dimension (e.g., a different length, width, and/or thickness) from the second plane.

In some embodiments, a respective plane 402 (e.g., plane 402-*a*) is aligned with other planes 402 (e.g., plane 402-*b* and plane 402-*n*) in the stack in a length direction (e.g., in the x-axis). In some embodiments, a respective plane 402 (e.g., plane 402-*a*) is aligned with other planes 402 (e.g., plane 402-*b* and plane 402-*n*) in the stack in a width direction (e.g., in the y-axis). In some embodiments, each of the planes 402 in the stack has the same x- and y-coordinates but a different z-coordinate.

Referring again to FIG. 4A, in some embodiments, adjacent planes (e.g., the plane 402-*a* and the plane 402-*b*) in the stack of planes are separated by a spacing D4 (408). In some embodiments, the spacing D4 (408) ranges from 0.5 cm to 2 cm inclusive.

FIG. 4A illustrates that, in some embodiments, one or more magnetometers 201 are disposed (e.g., positioned) on (e.g., in or within) a respective plane 402. The magnetometers 201 are arranged in an array (e.g., have an ordered arrangement). For example, FIG. 4A shows that the magnetometers are arranged in a rectangular array. In some embodiments, the magnetometers are arranged in a circular array, an ellipsoidal array, a hexagonal array, or any polygonal array. In some embodiments, the magnetometer array has an area that covers the whole cardiac activity area of a patient.

In some embodiments, a respective magnetometer 201 comprises a diamond NV center magnetometer (e.g., sensor). In some embodiments, a respective magnetometer 201 comprises an OPM (e.g., an OPM sensor). In some embodiments, a respective magnetometer 201 comprises a fluxgate sensor.

In some embodiments, a respective magnetometer 201 has a sensitivity better than 100 pT/$\sqrt{Hz}$. In some embodiments, a respective magnetometer 201 has a sensitivity better than 10 pT/$\sqrt{Hz}$. In some embodiments, a respective magnetometer 201 has a sensitivity that ranges from 0.1 pT/$\sqrt{Hz}$ to 10 PT/$\sqrt{Hz}$ inclusive. In some embodiments, a respective magnetometer 201 has a sensitivity that ranges from 0.1 fT/$\sqrt{Hz}$ to 10 PT/$\sqrt{Hz}$ inclusive.

In some embodiments, a respective magnetometer 201 in the device 200 has a cuboid shape with a dimension A1 (402) in a length direction (e.g., x-direction or x-axis), a dimension A2 (404) in a width direction (e.g., y-direction, y-axis or height direction), and a dimension A3 (406) in a thickness direction (e.g., z-direction, z-axis, plane normal direction). In some embodiments, the dimension A1 ranges from 1 cm to 3 cm inclusive. In some embodiments, the dimension A2 ranges from 1 cm to 3 cm inclusive. In some embodiments, the dimension A3 ranges from 1 cm to 3 cm inclusive.

In some embodiments, the device 200 is also referred to as having a multiplanar (e.g., multilayer) array of magnetometers or a three-dimensional array of magnetometers. For example, in some embodiments, the device 200 comprises an array of m×n×p magnetometers, wherein m corresponds to the number of magnetometers in a length direction (e.g., x-axis) of the device 200, n corresponds to the number of magnetometers in a width direction (e.g., y-axis) of the device 200, and p corresponds to the number of layers or planes (e.g., plane 402) of the device 200. In some embodiments, m is a positive integer that is at least 3. In some embodiments, n is a positive integer that is at least 3. In some embodiments, p is a positive integer that is at least 2.

In some embodiments, the number of magnetometers 201 in the device 200 is determined (e.g., optimized) according to the expected spatial characteristics of the signal sources, which include signals from a target organ as well as signals from other external sources (e.g., the Earth's magnetic field, external objects in the vicinity of the device, etc.). For example, in some embodiments, the number of magnetometers 201 in the device 200 is selected (e.g., optimized) based on the signal amplitude (e.g., magnetic field strength) from the target organ as well as signal amplitudes from external sources that may interfere with the target organ's signals. For example, for MCG applications, two sensors are sufficient for signal acquisition in an unshielded, relatively quiet environment. For disease biomarker extraction in a noisy, unshielded environment, 26 magnetometers are used. For accurate source localization in an unshielded environment, 36 or more magnetometers is desirable.

As a general rule, MEG requires more sensors than MCG, and the actual number of sensors is application dependent. For example, around 5 magnetometers are needed to observe alpha wave activity via MEG. To observe motor cortex activity or audio cortex activity, around 5 magnetometers each (i.e., about 10 sensors in total to observe both activities). To detect epilepsy source, more than 256 magnetometers will be required.

In some embodiments, the device 200 includes a first magnetometer in a first plane of the stack of planes and a second magnetometer 201 in a second plane in the stack of planes. The first magnetometer is aligned with the second magnetometer along the length and the width of the magnetometer array. For example, referring to FIG. 4A, the device 200 includes a magnetometer 201-1*a* positioned in the plane 402-*a*. The device 200 includes a magnetometer 201-1*b* positioned in the plane 402-*b*. In some embodiments, the magnetometer 201-1*a* is aligned with the magnetometer 201-1*b* in the x-direction and the y-direction. Stated another way, the magnetometer 201-1*a* and the magnetometer 201-1*b* have the same x- and y-coordinates but have a different z-coordinate.

In some embodiments, the array of magnetometers includes a first subset (e.g., one or more) of magnetometers positioned in a first plane of the stack of planes and a second subset of magnetometers positioned in a second plane of the stack of planes. The first subset of magnetometers is aligned with the second subset of magnetometers along the length and the width of the array (e.g., the first subset of magnetometers and the second subset of magnetometers have the same x- and y-coordinates).

In some embodiments, the device 200 includes a first plane and a second plane that is adjacent to the first plane in the thickness direction (e.g., z-axis). An array of magnetometers is positioned on (e.g., in) the first plane. An array of magnetometers is positioned on (e.g., in) the second plane. Each magnetometer in the first plane is exactly registered with (i.e., has the same x- and y-coordinates but a different z-coordinate) a corresponding magnetometer in the second plane. For example, referring to FIG. 4A, the device 200 includes a plane 402-*a* and a plane 402-*b* that is adjacent to the plane 402-*a* along the z-axis. Magnetometers, such as the magnetometers 201-1*a*, 201-3*a*, 201-*qa*, and 201-*pa* are positioned in the plane 402-*a*. The second plane 402-*b* includes magnetometers such as the magnetometers 201-1*b*, 201-3*b*, 201-*qb*, and 201-*pb*. The magnetometer 201-1*a* has the same x- and y-coordinates (and a different z-coordinate) as the magnetometer 201-1*b*. The magnetometer 201-3*a* has the same x- and y-coordinates (and a different z-coordinate) as the magnetometer 201-3*b*. The magnetometer 201-*qa* has the same x- and y-coordinates (and a different z-coordinate) as the magnetometer 201-*qb*. The magnetometer 201-*pa* has the same x- and y-coordinates (and a different z-coordinate) as the magnetometer 201-*pb*.

Figure 4B:
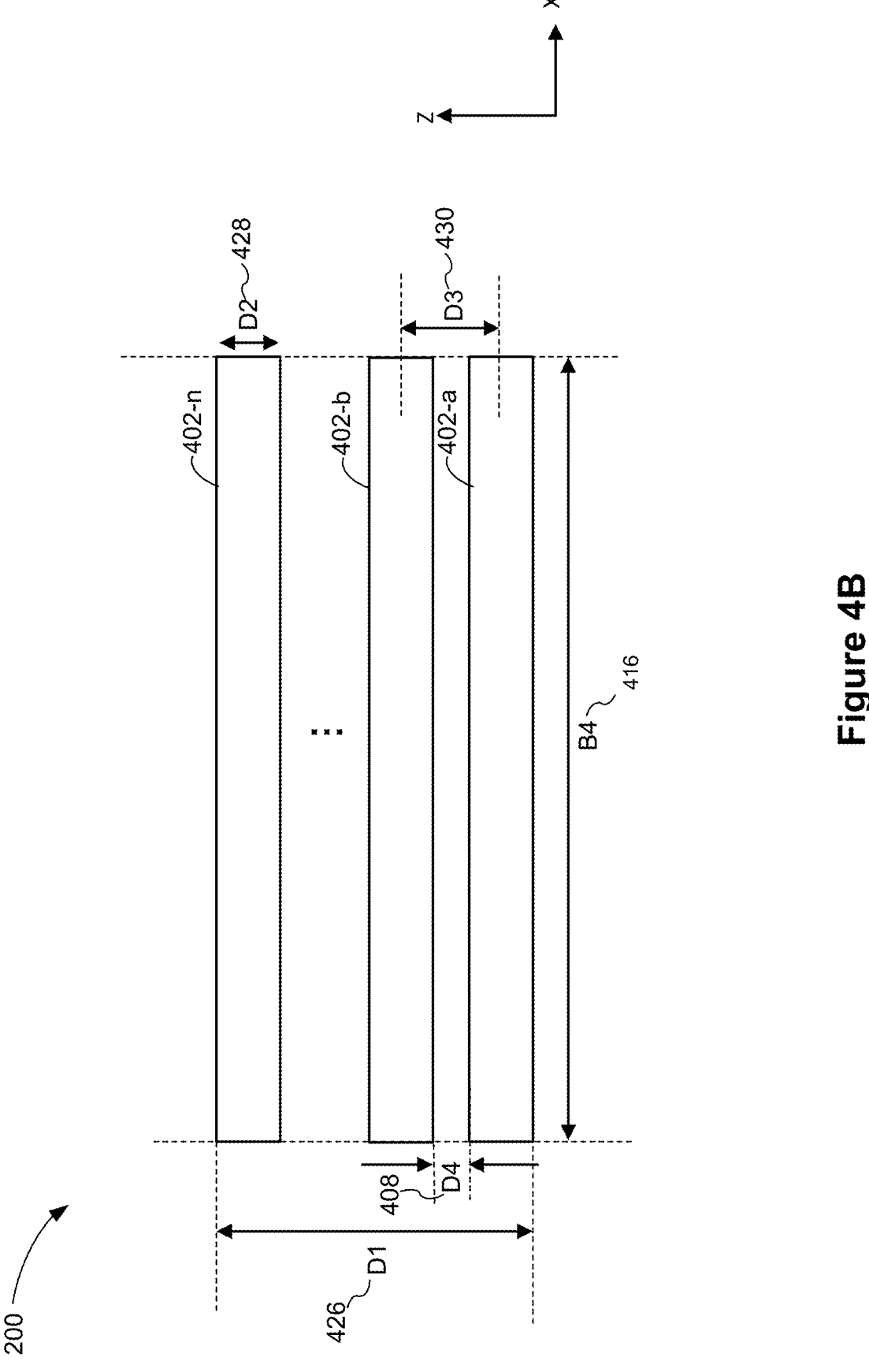
Figure 4C:
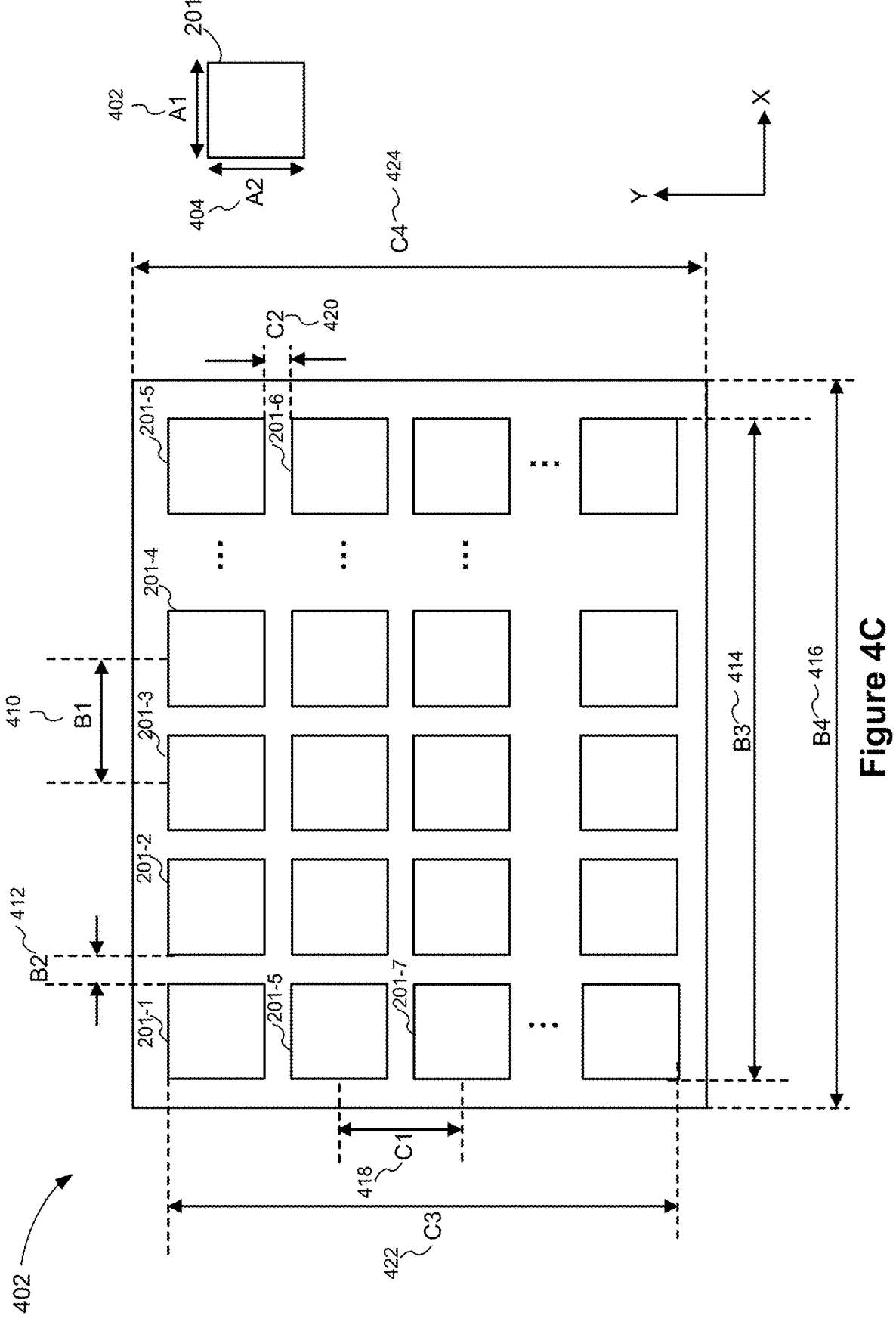
Figure 4D:
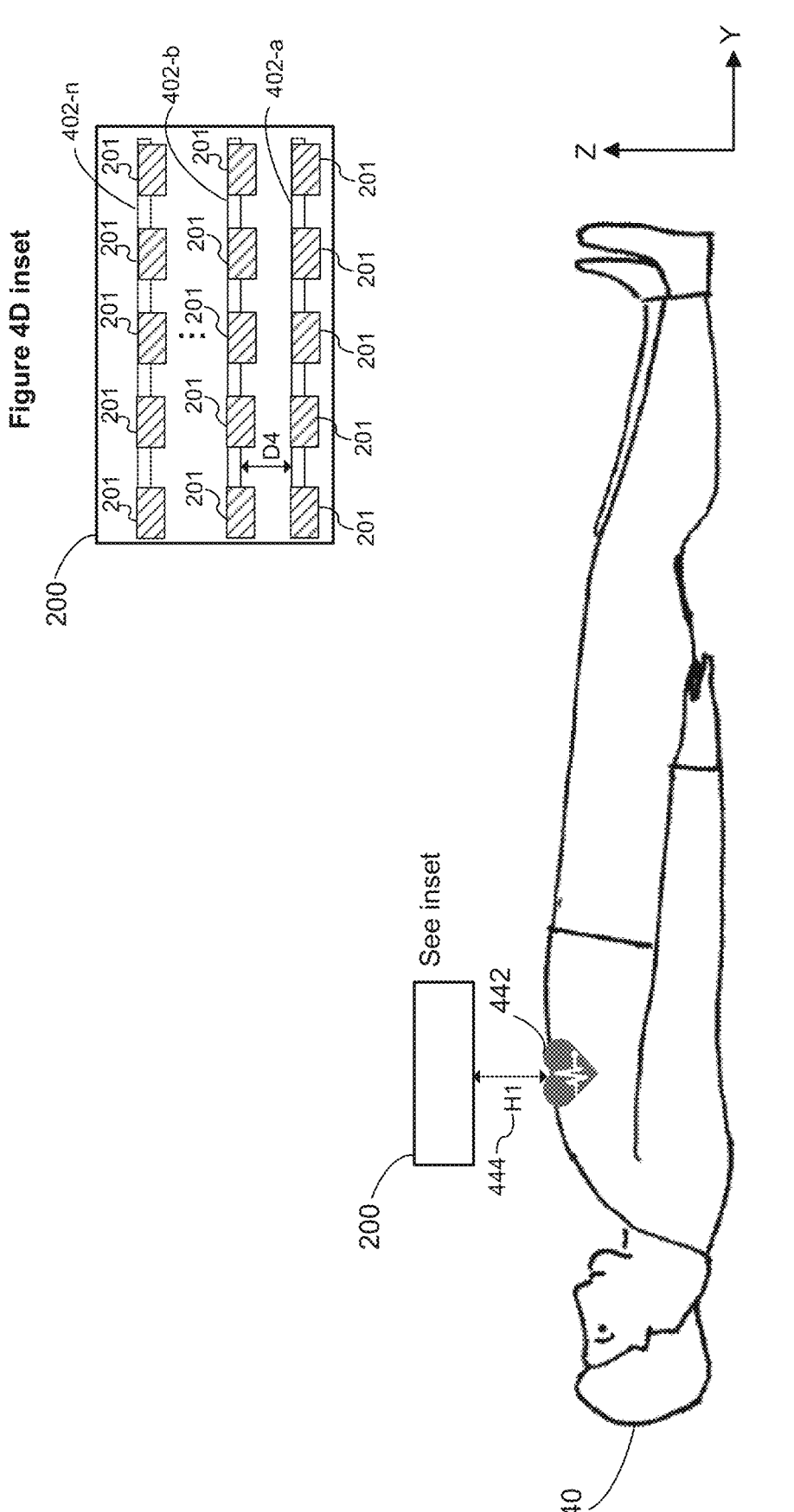
Figure 4E:
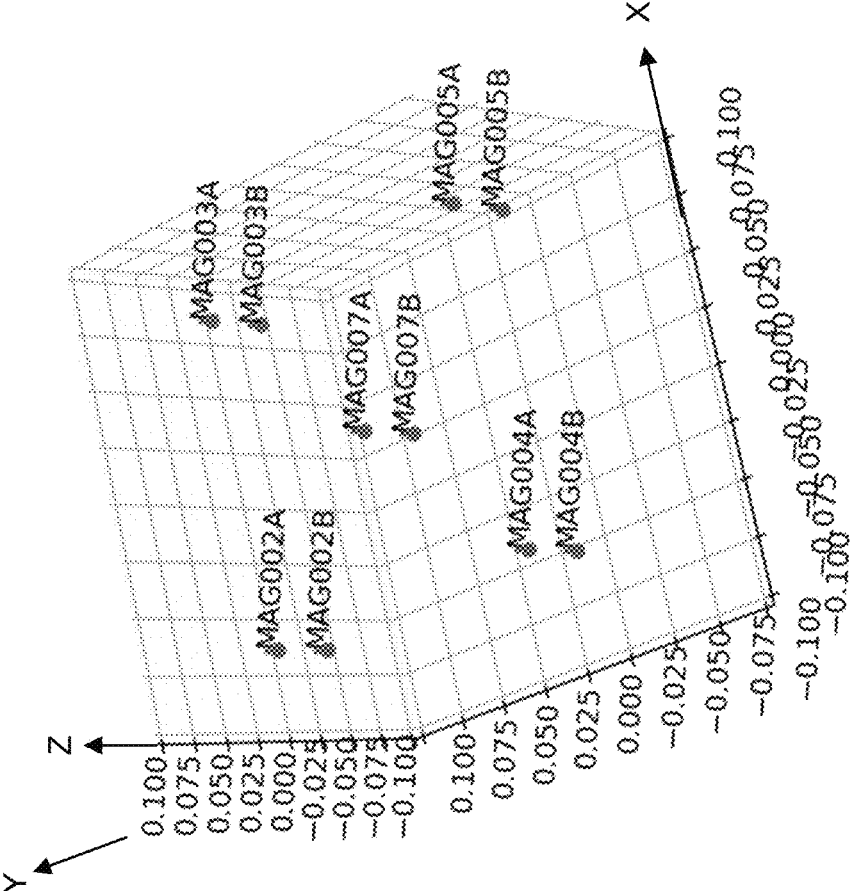

FIG. 4E illustrates an exemplary arrangement of magnetometers on 3D coordinate system. Each of the data points on the coordinate system represents a magnetometer. In the example of FIG. 4E, magnetometers MAG002B, MAG003B, MAG004B, MAG005B, and MAG007B are positioned on a first layer (e.g., a first plane) (e.g., plane 402-a), and magnetometers MAG002A, MAG003A, MAG004A, MAG005A, and MAG007A are positioned on a second layer (e.g., a second plane) (e.g., plane 402-b) that is distinct from the first layer. Magnetometers denoted by the same reference number (e.g., MAG002A and MAG002B, MAG003A and MAG003B, etc.) have the same x- and y-coordinates but a different z-coordinate.

FIG. 4B illustrates a plan view of the device 200 according to some embodiments. FIG. 4C illustrates a front view of the device 200 with an exemplary plane 402, in accordance with some embodiments.

In some embodiments, the stack of planes 402 includes a total thickness D1 (426). In some embodiments, D1 (426) ranges from 1 cm to 11 cm inclusive.

In some embodiments, adjacent planes (e.g., plane 402-a and 402-b) in the stack of planes 402 have a pitch D3 (430) (e.g., center-to-center distance in the z-direction). In some embodiments, D3 (430) ranges from 1 cm to 3 cm inclusive.

In some embodiments, a respective plane 402 has a length B4 (416) in the length direction. In some embodiments, B4 (416) ranges from 35 cm to 45 cm inclusive.

In some embodiments, a respective plane 402 has a width C4 (424) in the width direction. In some embodiments, C4 (424) ranges from 35 cm to 45 cm inclusive.

In some embodiments, a respective plane 402 has a thickness D2 (428) in the thickness direction. In some embodiments, D2 (428) ranges from 1 cm to 3 cm inclusive.

In some embodiments, adjacent magnetometers (e.g., magnetometer 201-3 and magnetometer 201-4 in FIG. 4C) in a respective plane 402 have a pitch B1 (410) (e.g., measured from the center of one magnetometer to the center of an adjacent magnetometer) in the length direction. In some embodiments, the pitch B1 (410) ranges from 1.5 cm to 3.5 cm inclusive.

In some embodiments, adjacent magnetometers (e.g., magnetometer 201-1 and magnetometer 201-2 in FIG. 4C) in a respective plane 402 are separated by a spacing B2 (412) in the length direction. In some embodiments, the spacing B2 (412) ranges from 0.5 cm to 2 cm inclusive.

In some embodiments, the magnetometers 201 in a respective plane 402 have a combined length B3 (414) in the length direction. In some embodiments, the combined length B3 (414) ranges from 30 cm to 40 cm inclusive.

In some embodiments, adjacent magnetometers (e.g., magnetometer 201-5 and magnetometer 201-7 in FIG. 4C) in a respective plane 402 have a pitch C1 (418) in the width direction. In some embodiments, the pitch C1 (418) ranges from 1.5 cm to 3.5 cm inclusive.

In some embodiments, adjacent magnetometers (e.g., magnetometer 201-5 and magnetometer 201-6 in FIG. 4C) in a respective plane 402 are separated by a spacing C2 (420) in the width direction. In some embodiments, the spacing C2 (420) ranges from 0.5 cm to 2 cm inclusive In some embodiments, the magnetometers 201 in a respective plane 402 have a combined width C3 (422) in the width direction. In some embodiments, the combined width C3 (422) ranges from 30 cm to 40 cm inclusive.

FIG. 4D illustrates placement of the device 200 over a target organ (e.g., heart 442) of a human subject 440 in accordance with some embodiments. In some embodiments, during device operation, the human subject 440 is positioned at a distance H1 (444) from the device 200. In some embodiments, the distance H1 (444) is between 0.1 cm and 5 cm. In some embodiments, the distance H1 (444) is at least 1 cm (e.g., between 1 cm and 5 cm, between 1 cm and 8 cm, etc.).

In accordance with some embodiments, the disclosed device 200 improves over existing biomagnetic field sensing systems because, by positioning the magnetometers in an array, magnetic fields can be sampled over a spatial range, thereby enabling one to discriminate between signals originating closer from a target organ (e.g., heart or brain) and signals originating further away from the target organ.

Additionally, the arrangement of magnetometers (e.g., sensors) over multiple planes and their alignment (e.g., at the same x- and y-positions) also improve the denoising process. Using the device 200 in FIG. 4D as an example, during device operation, because the plane 402-a is located closest to the target organ (e.g., the heart 442), magnetometers that positioned on (e.g., in or within) the plane 402-a are used primarily to measure magnetic fields from the target organ whereas magnetometers positioned on other planes (e.g., plane 402-b, 402-n, etc.) are used primarily to measure magnetic fields from other external sources (note that the magnetometers positioned on each of the planes 402 detect signals simultaneously from both the target organ as well as from other external sources). The magnetometer configuration and separation facilitate signal processing using gradiometry (e.g., in the z-direction). That is to say, in some embodiments, by subtracting the signals detected by the magnetometers in the first plane (e.g., the plane 402-a) and the signals detected by the magnetometers in the other planes (e.g., the plane 402-b and/or the plane 402-n), one would be able to obtain the signals from the target organ.

Figure 4F:
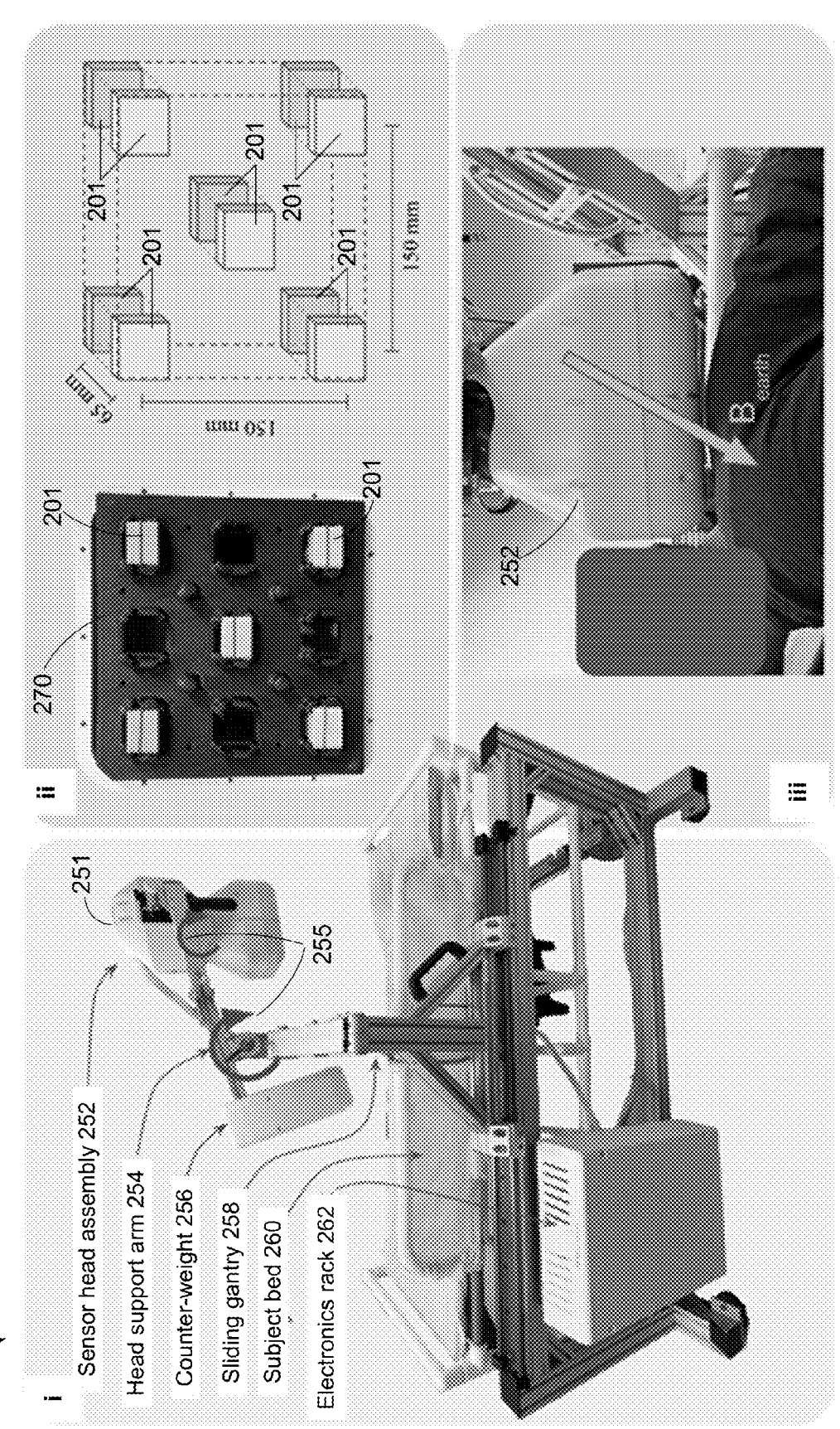

FIG. 4F illustrates an exemplary view of an MCG system 250 (e.g., device 200), in accordance with some embodiments. The MCG device 250 utilizes an array of scalar OPMs (e.g., magnetometers 201) to eliminate the need for magnetic shielding.

Panel i of FIG. 4F shows a photograph of the MCG system 250 with some of its components indicated. The MCG system 250 includes a sensor head assembly 252 and its accompanying electronics, which are positioned in a housing 251 (e.g., housing 143, FIG. 2). Sensors, such as magnetometers 201, and their control modules, are housed within the sensor head assembly 252 via housing 251. The sensor head assembly 252 and head support arm 254 can pivot about the points indicated by the circulating red arrows 255, allowing an operator to position the device optimally over a patient's chest. In some embodiments, the head support arm 254 includes a double-jointed pivot, which allows both coarse and fine rotation of the sensor head 252. The electronics rack 262 includes data acquisition electronics and other supporting components.

In some embodiments, the subject bed 260 is a magnetic resonance imaging (MRI) compatible hospital-grade bed constructed from non-magnetic PVC. The sensor head 252 is attached to a sliding gantry 258, which allows it to be adjusted along the body length of the patient. In some embodiments, the gantry support (e.g., sliding gantry 258) is assembled from extruded aluminum.

Panel ii of FIG. 4F is a photograph of the bottom layer of sensors within the sensor housing 251. In some embodiments, the housing 251 includes up to one, two, three, four, five, or six or more layers of sensors within the housing 251. In some embodiments, the sensor mount 270 is constructed by 3D printing. In some embodiments, the sensor mount 270 is nonmagnetic. In some embodiments, the magnetometers are mounted on a sensor mount 270. Although the example of FIG. 4F shows that the sensor mount 470 can accommodate up to 9 sensors per layer, it will be apparent to one of ordinary skill in the art that in practice, the sensor mount can be constructed to include more than 9 sensors per layer or fewer than 9 sensors per layer.

The right image in panel ii of FIG. 4F shows a schematic of two sensor layers indicating dimensions and gradiometric baseline. In the example shown in panel ii of FIG. 4F, the housing 251 includes a two-layer scalar OPM array that includes five pairs of commercial magnetometers, arranged as shown. To ensure a high common-mode rejection ratio (CMRR), the magnetometers were paired as gradiometers with a baseline in the direction normal to the sensor array plane. The sensor spacings were chosen to maximize the common mode variance for distant noise sources while minimizing that variance for nearby signal sources.

Panel iii in FIG. 4F shows a photograph of the sensor head 252 centered above a patient for data acquisition. The gap between the sensor head 252 and patient is in the range of about 0.5 cm to 5 cm. The approximate direction of the Earth's magnetic field is indicated by the arrow $B_{earth}$. Scalar OPMs measure projections of small field fluctuations on the total magnetic field vector, which in an unshielded environment is dominated by the Earth's geomagnetic field. In some embodiments, the MCG system 250 (e.g., device 200) and patient are positioned such that the Earth's field pointed approximately normal to the chest surface. As a result, the measurements primarily record cardiac magnetic fields in the direction of the earth's magnetic field.

Figure 4G:
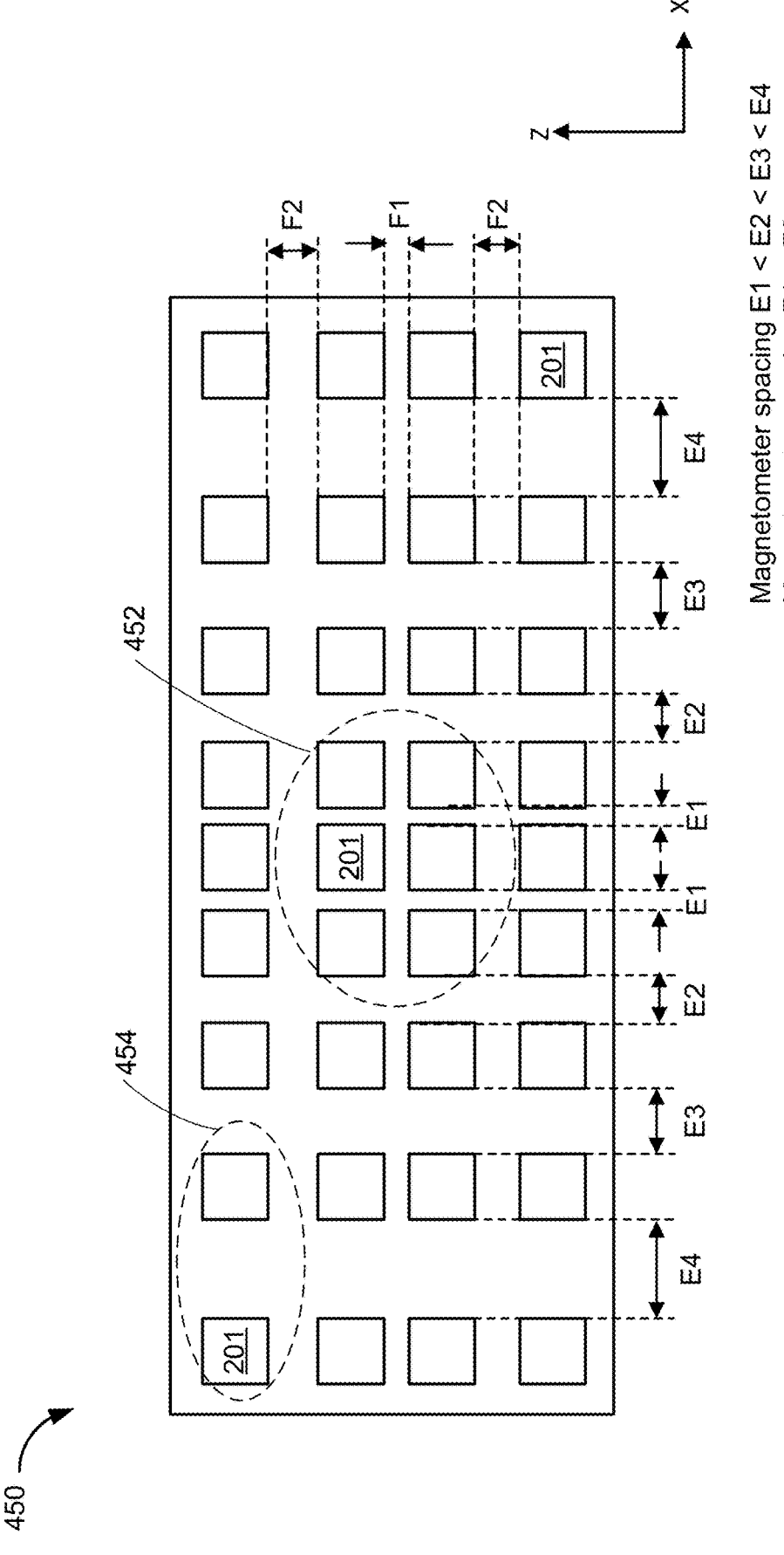

In some embodiments, magnetometers within a plane (or a layer, or an array) can have varying packing densities. FIG. 4G illustrates an exemplary plane 450 of the device 200 in which the magnetometers 201 have different packing densities, in accordance with some embodiments. The plane 450 includes a first set 452 (e.g., one or more) of magnetometers 201 with higher packing density and a second set 454 (e.g., one or more) of magnetometers 201 with lower packing density. During device use, the higher packing density magnetometers (e.g., the first set 452) are positioned at (e.g., over, aligned with, proximate to) the chest of a patient to capture more signals, whereas the lower packing density magnetometers (e.g., the second set 454) are positioned further away from the patient's chest to capture background (e.g., noise) signals.

In some embodiments, the varying packing densities of the magnetometers can be achieved by varying the separations between magnetometers within a plane. In other words, the magnetometers within a plane can be irregularly spaced. Referring again to the example of FIG. 4G, magnetometers 201 positioned along the x-axis can have different spacings E1, E2, E3, and E4, with E1 being the smallest and E4 being the largest. Magnetometers 201 positioned along the y-axis can have different spacings such as F1 and F2, where F1 is smaller than F2.

According to the sensor array geometry design principles disclosed herein, the magnetometers 201 within an array (or a layer or a plane) can be irregularly spaced as long as the spacings optimize the magnetometer density based on their form factor. In some embodiments, the magnetometers within an array can be irregularly spaced as long as the sampling requirements are met (e.g., the irregular spacings satisfy the Nyquist sampling rate in a Fourier space of the wavevectors of the target organ's magnetic field, the irregular spacings provide sufficient wavevector coverage to recover information from both the biomagnetic field from the subject's organ and the background magnetic field).

In some embodiments, the MCG device/system 200 includes one or more reference sensors (e.g., magnetometers 201) for acquiring long range (e.g., baseline or background) magnetic field signals. The reference sensors should be positioned far enough away from the source of interest (e.g., a patient's heart) so that they do not capture the source signals. For example, in some embodiments, the reference sensors are distributed around the array. In some embodiments, the reference sensors are positioned on the periphery (e.g., corners or edges) of a plane (e.g., plane 402) of the device 200. In some embodiments, the reference sensors can be positioned at a location beyond the array (e.g., at a distance about 0.5 meter and 1 meter from the array, on a positioning arm 142, or on portions of the device 200 other than the array).

According to the present disclosure, the dimensions/spacings discussed with respect to the exemplary embodiments in FIGS. 4A to 4G satisfy the constraints in Fourier space for the case where the cardiac source is located ~10 cm below the panel.

Other Design Considerations

There are several relationships to consider when determining the array dimensions.

In some embodiments, the distance H1 (444) and the spacing D4 (408) are determined (e.g., optimized) by considering two factors, namely denoising and source localization. For denoising, the optimal gradiometer baseline distance (spacing between and within planes) is a function of distance to the source of interest as well as the spatial character of the noise from distant sources. The array should sample space such that it can capture small scale variations of the source field, and large-scale features of noise. Stated another way, for denoising, the values for the distance H1 (444) and the spacing D4 (408) are chosen so as to maximize the common mode variance among sensors from distant noise sources while minimizing that variance for nearby signal sources. For source localization, the values for the distance H1 (444) and the spacing D4 (408) are chosen so as to obtain the highest resolution possible, but there are diminishing returns for tighter packing given a sensor-source distance.

Generally speaking, when the sensor size is smaller (e.g., smaller values of A1, A2, and/or A3), a larger number of sensors can be positioned on a plane, which translates to better resolution, which is better for mapping fields and localizing sources. However, given a source-sensor distance (e.g., the distance H1), there is not much benefit in increasing resolution beyond a certain point.

When designing the array spacing (e.g., B1, B2, C1, and C2), one should also take into account the optimal gradiometer baseline, (i.e., the relative difference in magnetic field gradient between near and far sources) for optimal denoising. The optimal array spacing is set by the expected spatial gradient of the signal field compared to that of the noise fields. In an ideal world, one would have a tightly packed array of sensors completely filling the volume surrounding the subject—providing both high resolution for source localization and large spatial sampling for denoising.

There is a correlation between the distance H1 (444) and the array parameters (e.g., the dimensions such as B1, B2, B3, B4, C1, C2, C3, and C4), because H1 will determine the spatial characteristics of the signal field. When the distance H1 increases, the magnetometers in the array can be less tightly packed to fully characterize the signal field. Additionally, as the distance H1 increases, the signal field amplitude decreases rapidly, and its spatial gradients get smaller, leading to decreased ability of the sensor array to discriminate between the signal field and other noise sources. Consequently, as the distance H1 gets larger, the overall array size (e.g., B3, B4, C3, and C4) would need to be increased in order to sample a larger spatial region.

Signal Processing

One of the major challenges in detecting biomagnetic signals in magnetically unshielded environments is the extremely low signal-to-noise ratio of the biomagnetic signals. For example, in the case of a human heart, the amplitude of the cardiac signals from the heart is very small compared to magnetic interference from sources external to the heart. The strength of the Earth's magnetic field is approximately 50 microTeslas, which is about a million times larger in amplitude than the expected signal of the heart's magnetic field when a biomagnetic field sensing device is positioned just outside the chest of a patient. Clinical environments are often magnetically noisy with electrical equipment radiating magnetic interference not only at the power line frequency and its harmonics, but also across a wide frequency range.

As described above, in some embodiments, the apparatus 200 uses magnetometers 201 that are each configured to simultaneously detect a biomagnetic field from at least a portion of the subject's organ and a background magnetic field and output a signal indicative of the detected biomagnetic field and the background magnetic field. In order to resolve the cardiac signals, it is important to reduce the noise contributions in the collected signals and improve the signal-to-noise ratio of the cardiac signals. Some aspects of the present disclosure describe systems and methods for denoising cardiac signals that are collected using unshielded (e.g., magnetically unshielded) multichannel magnetometers (e.g., device 200). The technical effect of the denoising processes as disclosed herein enables the system/apparatus to operate in a magnetically unshielded environment.

Figure 5A:
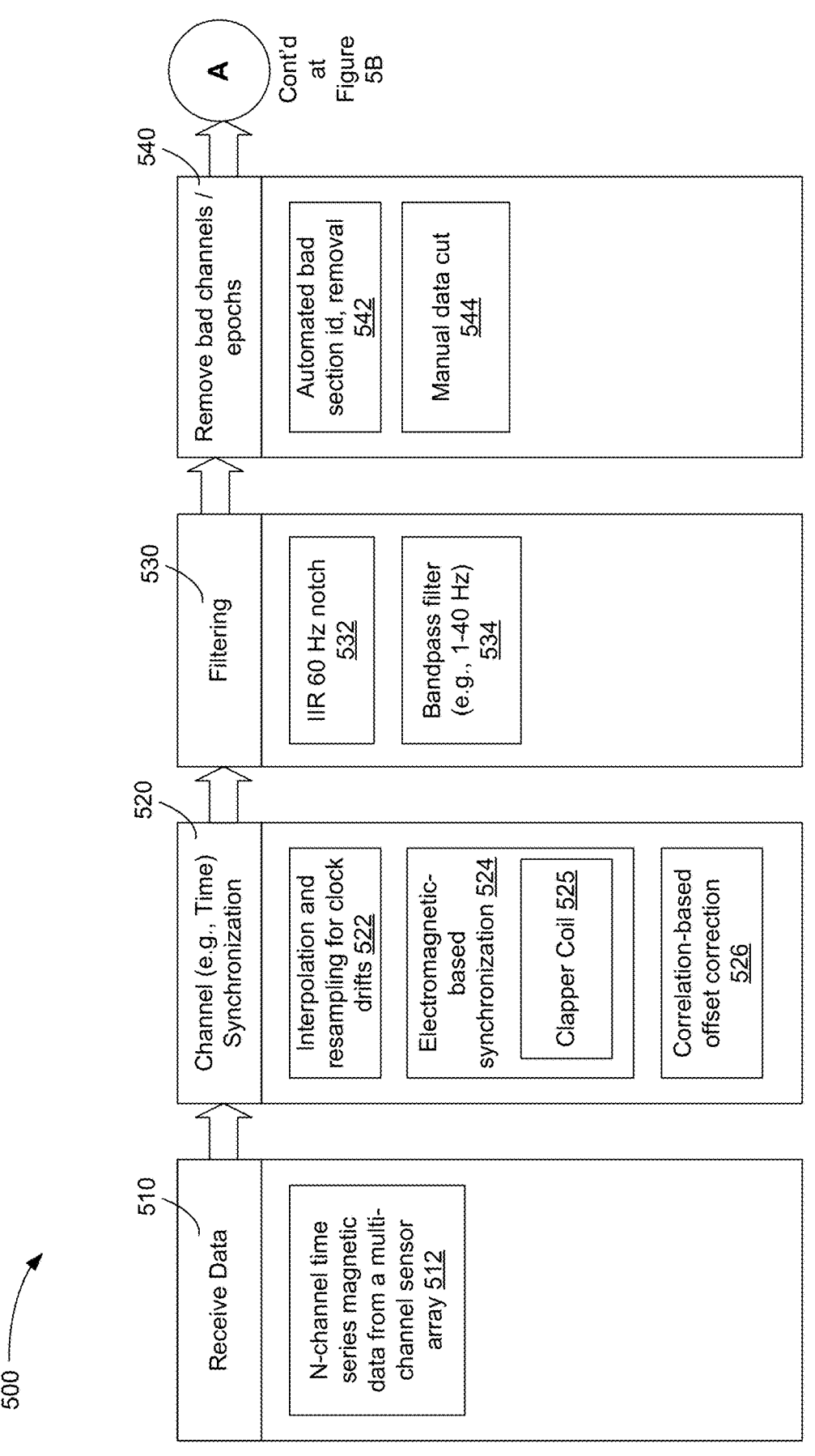
FIGS. 5A and 5B illustrate a workflow for measuring magnetic fields from a target organ of a human subject, in accordance with some embodiments.
Figure 5B:
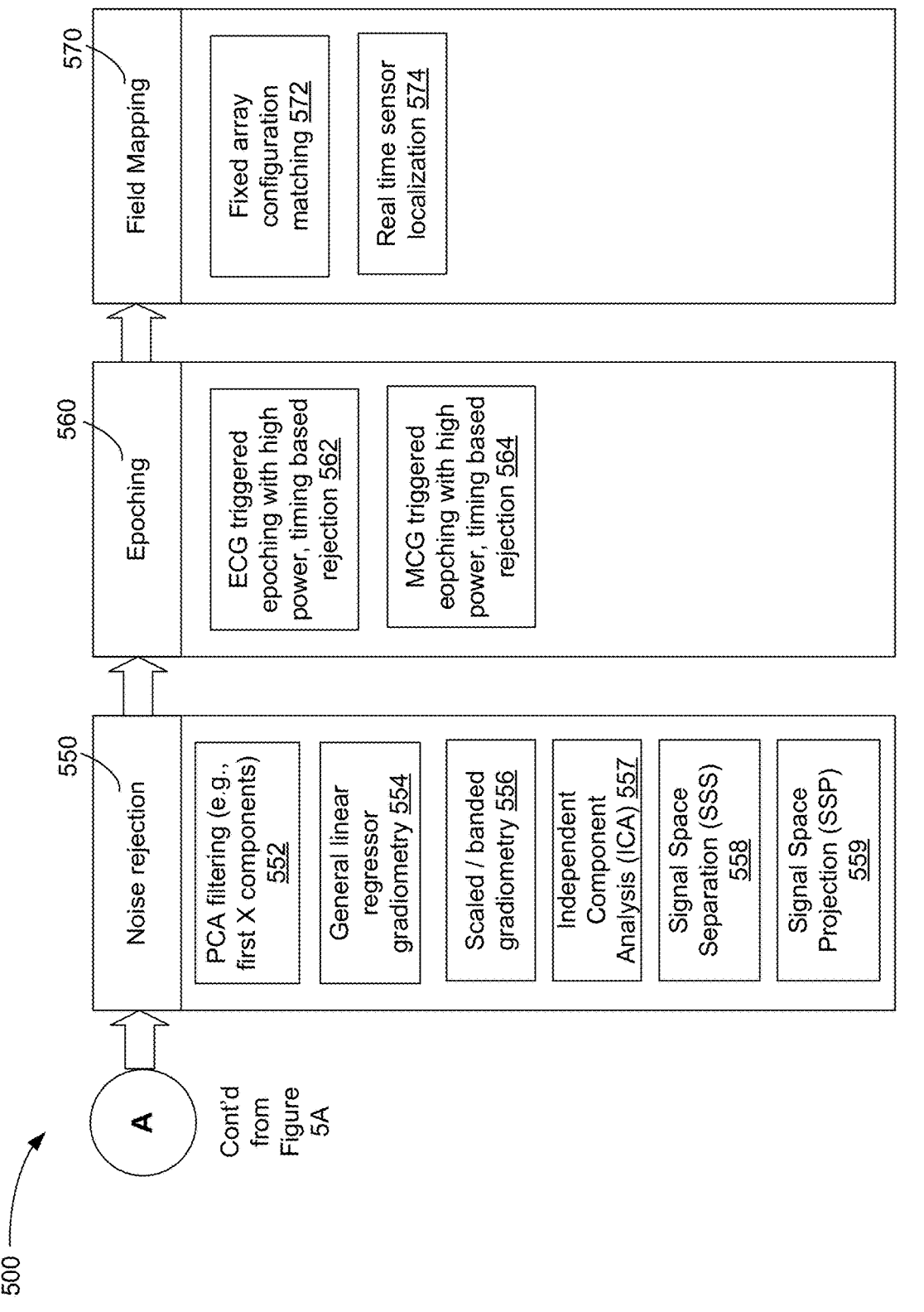

FIGS. 5A and 5B illustrate a workflow 500 for measuring magnetic fields from a target organ (e.g., heart or brain) of a human subject, in accordance with some embodiments. In some embodiments, the steps in the workflow 500 are performed at a computing device (e.g., CPU(s) 302) of computer system 120). In some embodiments, the computing device is communicatively connected with a device (e.g., device 200).

In some embodiments, the workflow 500 includes receiving data that is acquired by a device (Step 510) that includes a plurality of magnetometers (e.g., device 200 as illustrated in FIG. 1B). In some embodiments, the data comprises an N-channel time-series magnetic data (512) acquired by a multi-channel magnetometer device, wherein N is the number of channels of the magnetometer device (e.g., the device 200 as described in FIGS. 1, 2, and 4A to 4E). In some embodiments, each magnetometer is a single-channel sensor and N corresponds to the total number of magnetometers in the device. In some embodiments, the device includes magnetometers that are arranged in an array, such as the device 200 that is illustrated in FIGS. 4A to 4G. For example, suppose the magnetometer array comprises an A×B array of magnetometers arranged in a stack of C planes, then N=A×B×C. In some embodiments, each magnetometer is a multi-channel sensor (e.g., a multi-axis sensor) that can contribute up to three channels. In some embodiments, each dataset is tagged with a unique identifier. In some embodiments, each dataset is cataloged according to its associated metadata.

In some embodiments, the computing device receives the data in real time (e.g., automatically, without user intervention) as the data is acquired by the magnetometer array. In some embodiments, the computing device receives the data asynchronously, at a time subsequent to when the data was acquired.

Figure 6A:
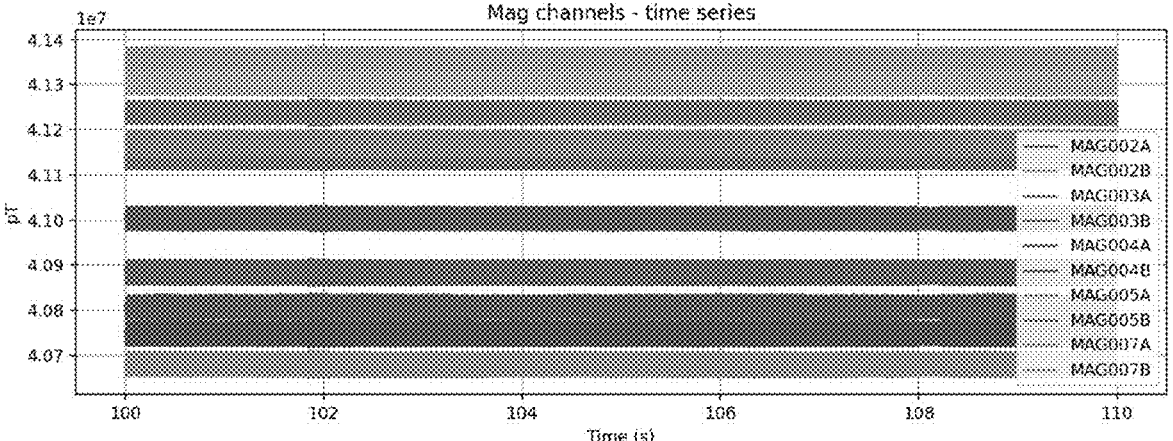
FIGS. 6A to 6G illustrate time-series magnetic field data from a multi-channel magnetometer array.

FIG. 6A is a graph showing actual raw time-series magnetic field data from (e.g., collected by, generated by) a multi-channel magnetometer array over 10 seconds, according to some embodiments. The data in FIG. 6A is collected by the magnetometer array by placing the array over a human subject at room temperature, in a magnetically unshielded environment. Each of the lines in the graph corresponds to magnetic field signals collected by a respective channel of the array (the lines are offset for clarity). The magnetic signals include signals from a target organ of the human subject and signals from interference sources.

Referring again to FIG. 5A, the workflow 500 includes synchronizing the N channels of time-series magnetic data to a common clock (e.g., a common time reference). This is illustrated as step 520 in FIG. 5A. The channel synchronization step ensures that each of the channels holds the same clock and timing. Time synchronization is also critical for the epoching step (step 560).

In some embodiments, the computing device synchronizes the channels by interpolating and sampling for clock drifts (522).

In some embodiments, channel synchronization is performed by aligning common signals that were injected in all channels.

In some embodiments, the computing device synchronizes the channels by using electromagnetic-based techniques (524) (e.g., by using a common signal that will show up in all the channels). An example electromagnetic-based technique is a clapper coil 525 that provides a well-characterized calibration source. In some embodiments, the clapper coil 525 is configured to emit a unique electromagnetic signature (e.g., signal), which is captured by the magnetometer channels while (e.g., during, as) the biomagnetic fields are measured. The unique electromagnetic signature of the clapper coil 525 can be used to precisely synchronize (e.g., align) the signals from the different channels of the device 200.

In some embodiments, the clapper coil 525 includes a coil of conductive wire (e.g., copper wire) that is positioned on board the magnetometer device 200 and rigidly connected to the sensor array. For example, the clapper coil 525 can be fabricated by winding copper wire around a 3D-printed mounting core with a set number of windings within a defined volume. Periodic (e.g., sinusoidal) waveforms may be driven through the coil using a current driver, and the resulting electromagnetic field can be detected by the magnetometers. Since the parameters of the coil are well known, a forward model of the expected magnetic field at each of the sensor locations can be calculated and compared to the measured results. In order for the calibration to work properly, it is important to know the exact distance and orientation of the clapper coil 525 with respect to each of the magnetometers of the device 200. In some embodiments, the precise, predefined position of the clapper coil 525 can be defined in the same computer aided design (CAD) drawing as the device.

In some embodiments, the computing device synchronizes the channels using correlation based offset correction (526) (e.g., cross-correlating the signals from the channels to determine offsets between the channels).

Figure 6B:
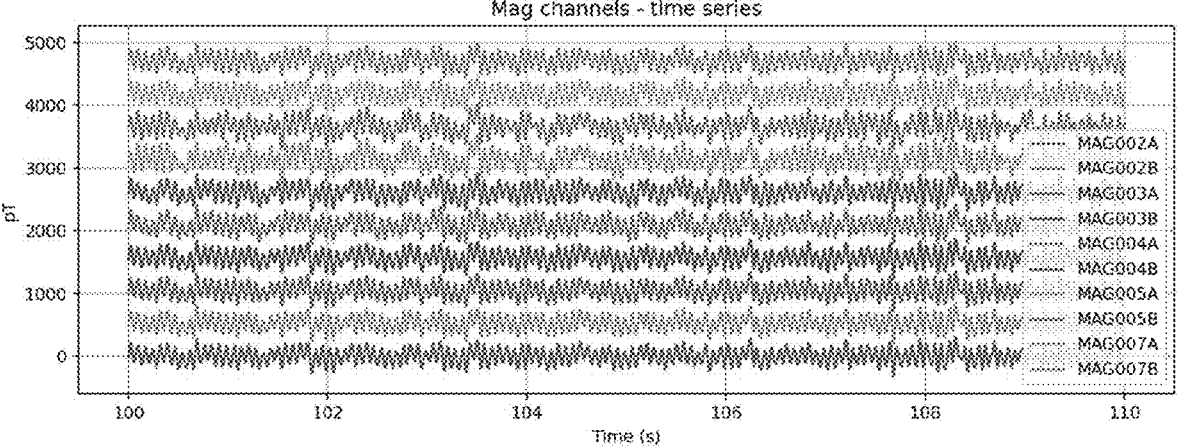

In some embodiments, the workflow 500 includes applying one or more filters (step 530) to the synchronized time-series magnetic data to obtain filtered data. In some embodiments, the computing device applies an infinite impulse response (IIR) filter (e.g., notch filter) (532) at the expected line noise (e.g., 60 Hz frequency). In some embodiments, the computing device applies a bandpass filter (534), such as a bi-directional Butterworth digital filter, with frequency between 0.5 to 40 Hertz (or with a similar frequency range that is applied in electrocardiography (ECG). FIG. 6B is a graph of the same 10-second time-series raw magnetic field data in FIG. 6A after the synchronization and filtering steps.

With continued reference to FIG. 5A, in some embodiments, the workflow 500 includes removing bad channels/epochs (step 540). The bad channel/epoch removal can be automated (542) or manual (544). For example, in some embodiments, the computing device automatically detects channel(s) and/or data segments that are defective and/or have artifacts, and removes those channel(s) and/or data segments from subsequent analysis. Artifacts can include motion artifacts (e.g., the subject moved, someone bumped into the array or the patient bed, or moved a support structure supporting the magnetometer array, etc.) and magnetic artifacts (e.g., large magnetic disturbances that are unexpected).

Referring to FIG. 5B, in some embodiments, the workflow 500 includes applying one or more noise rejection (e.g., denoising) techniques to the filtered data (step 550). Until this point, unless bad channel(s) have been removed in step 540, there are still N channels of filtered data corresponding to the N-channel magnetometer device.

Noise Rejection Approaches

In some embodiments, as illustrated in FIG. 5B, the noise reduction techniques include one or more of: Principal Component Analysis (PCA) (552), general linear regression gradiometry (554), scaled/banded gradiometry (556), independent component analysis (ICA) 557, signal space separation (SSS) (558), and signal space projection (SSP (559).

PCA (or PCA filtering) is a technique for analyzing datasets that contain a high number of dimensions/features per observation. In some embodiments, the computing device extracts, from the filtered data, a subset of variables from all variables of the filtered data. The subset of variables re-frames the sensor-space data to some signal-space, where each variable is the data from a sensor channel and explains some part of the statistical variance among all the signals. In the present disclosure, variables (e.g., the first X components) that explain the greatest variance among the sensor array are selected and considered as the common mode noise from far-away sources. By setting these variables to zero before transforming back to sensor-space variables (i.e., the time-series signals from the original set of magnetometers), those common mode noise contributions are removed.

Figure 6C:
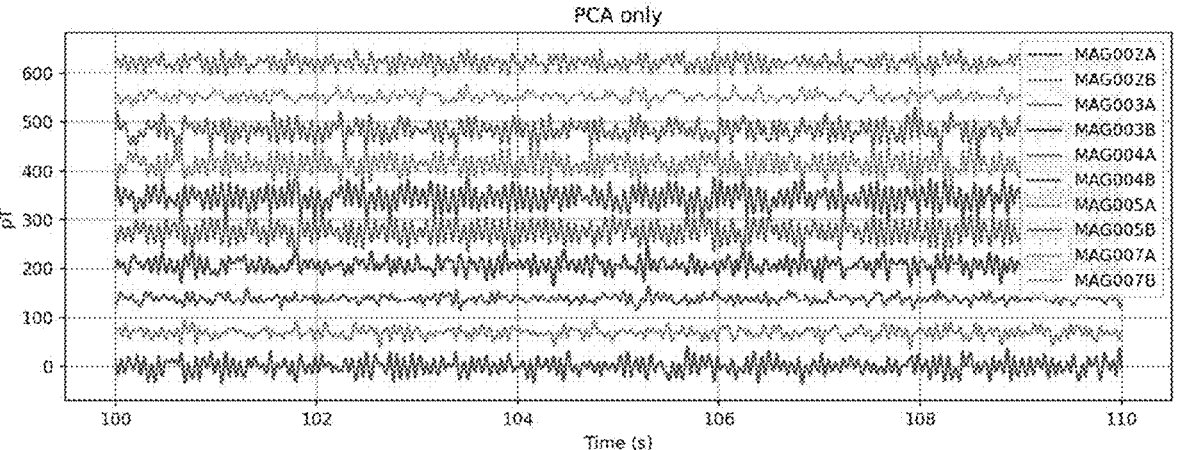

In some embodiments, the PCA filtering is performed in time domain. The PCA transform recasts the real signal channels into a new set of channels (e.g., variables) that capture the largest variance in the total set of original signals. For example, there were ten original channels and a 60 Hz noise (e.g., an electrical line noise) shows up on all the original channels, one of the new "channels" will be entirely 60 Hz oscillation, while the other new "channels" will ideally not contain any. As a result, setting this 60 Hz channel to zero before transforming back will remove the 60 Hz noise over the whole sensor array. Using this approach, for example, one such variable (principal component) may explain the variance among sensor signals arising from a large air-conditioning unit in the room/building where the magnetometer array is located. FIG. 6C shows a graph of the same 10-second time-series raw magnetic field data in FIG. 6A, after applying synchronization, filtering, and PCA.

In some embodiments, the denoising techniques include unscaled gradiometry, where signals from two sensors are assumed to be calibrated and simply subtracted from each other.

In some embodiments, the denoising techniques include linear regression gradiometry (e.g., linear regression scaled gradiometry). Linear regression is a technique for fitting known features to the target data, with an overall scaling factor (hence linear). Linear regression for gradiometry works as follows: Typically, one finds two signals which have some sort of linear relationship. We can call these X and Y. In signal processing, the dependent signal, Y, is our target signal. In a specific case, Y is the signal recorded at the sensor closest to the heart. X can be any signal feature that represents unwanted interference, for example, the second sensor, which should have a smaller amplitude heart signal, but comparable environmental interference. In a perfect gradiometry scenario, Y is the sum of the environmental noise X, and the heart signal, $\varepsilon$, which can be also interpreted as the residuals from the linear relationship:

(1)

$$
\begin{aligned}
y_1 &= x_1\beta + \varepsilon_1 \\
y_2 &= x_2\beta + \varepsilon_2 \\
y_3 &= x_3\beta + \varepsilon_3 \rightarrow \\
&\vdots \\
y_n &= x_n\beta + \varepsilon_n
\end{aligned}
\quad
\begin{bmatrix} y_1 \\ y_2 \\ y_3 \\ \vdots \\ y_n \end{bmatrix}
=
\begin{bmatrix} x_1 \\ x_2 \\ x_3 \\ \vdots \\ x_n \end{bmatrix}
[\beta]
+
\begin{bmatrix} \varepsilon_1 \\ \varepsilon_2 \\ \varepsilon_3 \\ \vdots \\ \varepsilon_n \end{bmatrix}
\rightarrow Y = X\beta + \varepsilon
\quad (1)
$$

In Equation (1), each index i(i=1, 2, 3, . . . ) refers to a data point in time. The weighting factor, $\beta$ is the same as a scale factor for balancing the gradiometer. For gradiometry, the same weighting factor $\beta$ can be used for each index because magnetic fields measured at one sensor are linearly related to fields measured at another location. This breaks down rapidly for multiple close sources of interference, since fields originating from different directions will scale differently. To solve this problem, a transverse array can be very beneficial, since each direction will have a principal feature to regress out of the central target sensor. In some instances, linear regression scaled gradiometry is useful in situations where the largest contributions to the signal is noise, which is expected to be homogenous over the two sensors of interest (if this is not the case, the resulting scaling can be wrong).

In some embodiments, the scale factor $\beta$ for balancing the gradiometer can be calculated as the ratio between the mean or the median of each of the two signals.

Figure 7:
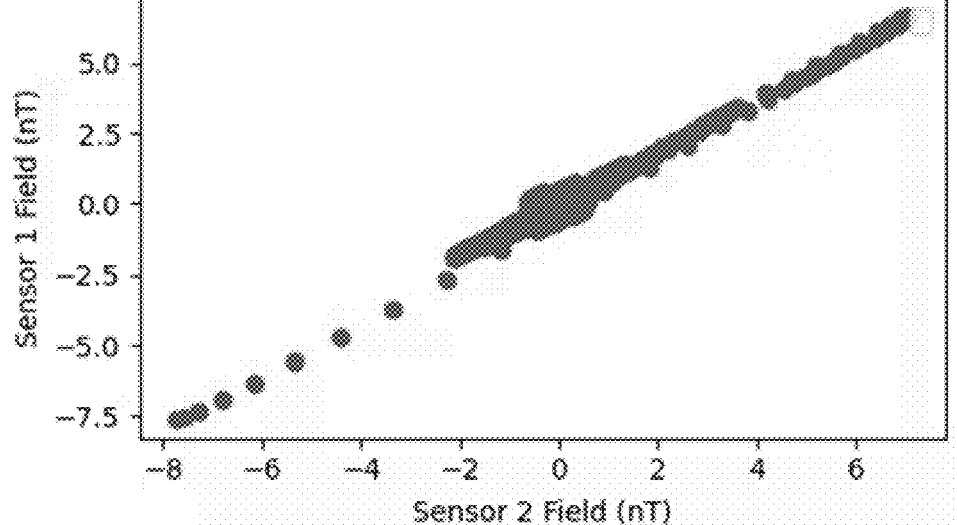
FIG. 7 is a graph showing an actual signal from two Geometrics sensors arranged in an axial gradiometer arrangement to the heart, according to some embodiments.

FIG. 7 is a graph showing an actual signal from two Geometrics sensors arranged in an axial gradiometer arrangement to the heart. The graph illustrates that the relationship between sensor 1 and sensor 2 is linear.

The General Linear Model (GLM) for linear regression retains the same basic form (Y=X$\beta$+$\varepsilon$). Now though, Y is considered as the sum of one or more experimental signals (X), each multiplied by a weighting factor ($\beta$), plus random error ($\varepsilon$). As a result, X is now an N×M matrix, where N is the number of time points, and M is the number of signals to regress.

In GLM both Y and $\varepsilon$ remain as single column vectors containing the signal and heartbeat respectively for a single sensor at successive time points (i=1 to n). The experimental design matrix (X), however, can consist of multiple columns instead of only one. Each new column of X reflects a specific source of interference ("regressor") that we want to remove. While for gradiometry, these would be other sensor outputs, we could also include a fluxgate signal, or the average of the sensor array, or the motion of the subject, or, for the diamond NV center magnetometer, a reference photodiode output.

Figure 8:
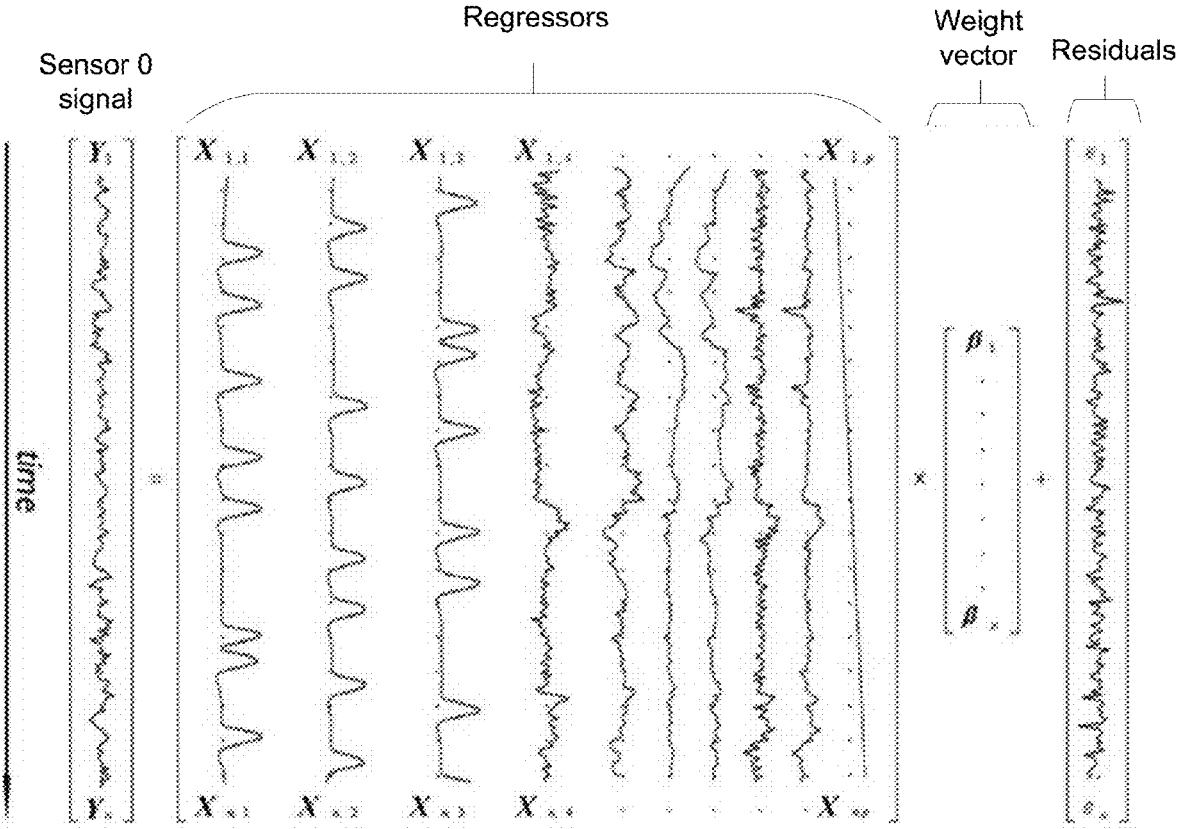
FIG. 8 illustrates a General Linear Model (GLM) for linear regression according to some embodiments.

FIG. 8 illustrates the GLM, in which Y, X, and ε are represented as signals. This figure is adapted from "Questions and Answers in MRI," available at mriquestions.com/general-linear-model.html, which is incorporated by reference herein in its entirety.

Figures 9A, 9B:
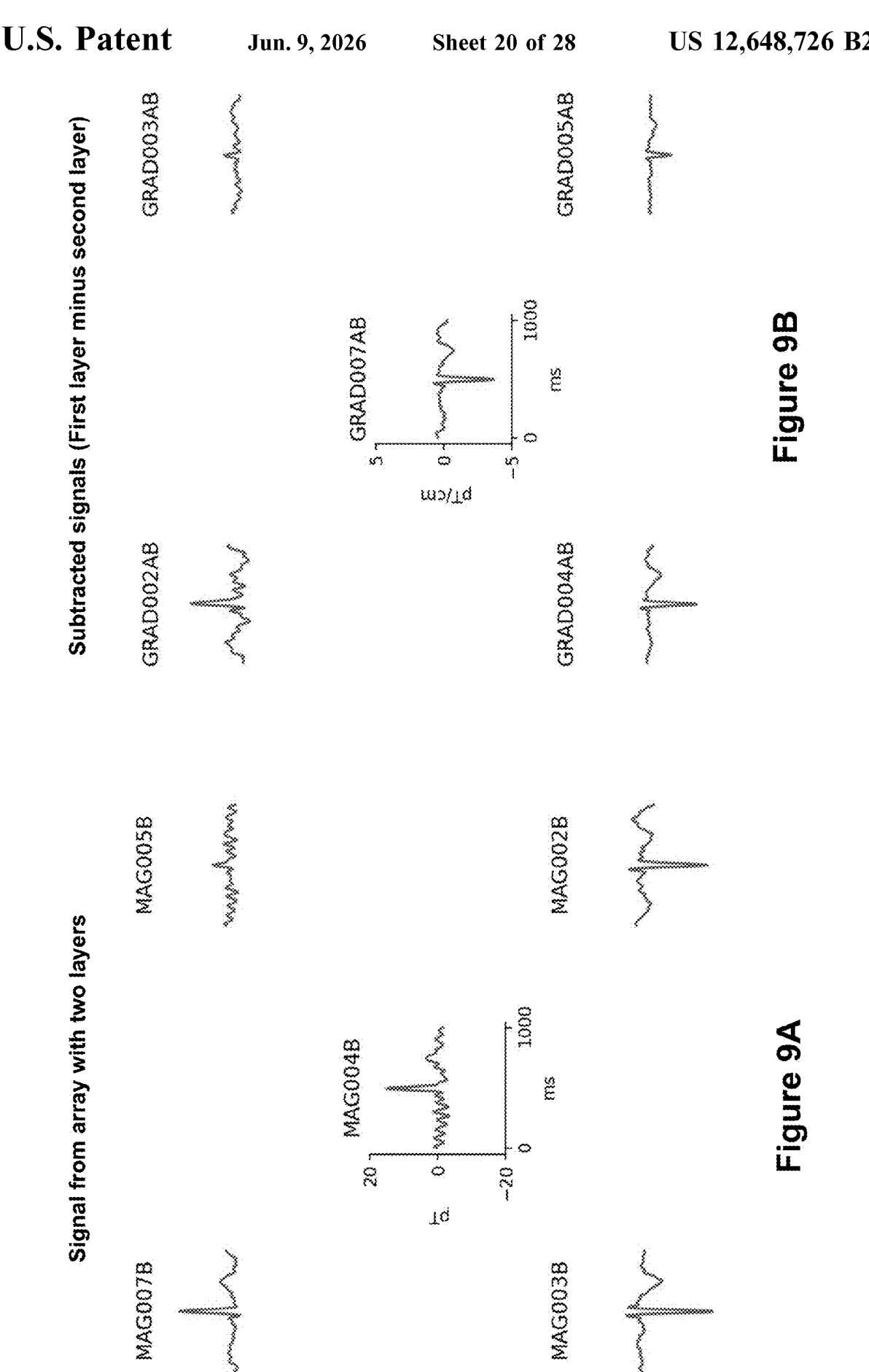
FIGS. 9A and 9B illustrate magnetic field signals from an array with two layers of magnetometers according to some embodiments.

According to some embodiments of the present disclosure, linear regression gradiometry is applied to the filtered data (e.g., N channels of filtered data). This process takes the front and back sensors (e.g., sensors that have the same x- and y-coordinates but a different z-coordinates) and subtracts them pairwise with a scaling factor that takes into account the linear regression against each of these signals. The processed signal for a respective pair of sensors after linear regression gradiometry can be represented as: Signal$_{sensor\_1}$ minus β×Signal$_{sensor\_2}$. This way, the scale of one sensor signal is matched to the other sensor signal. This, in turn, reduces the maximum amount of signal which is almost always coming from noise in a magnetically unshielded case. In some embodiments, the value of is β determined (e.g., calibrated) for every MCG dataset corresponding to a patient scan. FIG. 9A illustrates magnetic field signals from an array with two layers of magnetometers, in which the magnetometers in the first layer are aligned with the magnetometers in the second layer in the length (x-axis) and width (y-axis) directions. FIG. 9B shows signal subtraction of the first layer from the second layer.

Figure 6D:
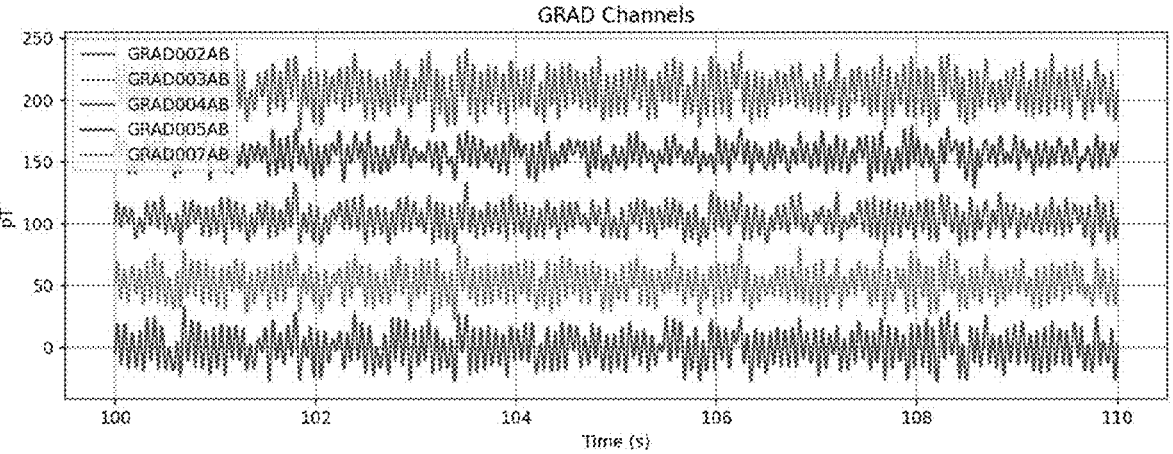
Figure 6E:
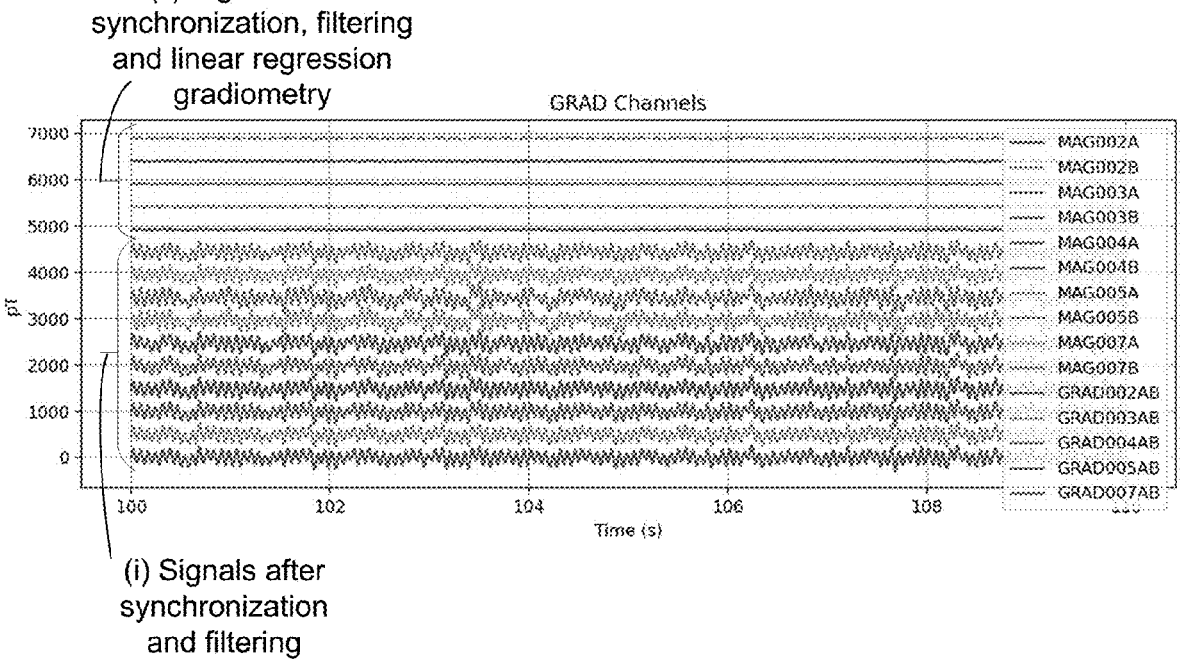

FIG. 6D shows a graph of the same 10-second time-series raw magnetic field data in FIG. 6A, after synchronization, filtering, and linear regression gradiometry. FIG. 6E compares the time-series magnetic field data (i) after synchronization and filtering alongside with the data (ii) after synchronization, filtering and linear regression gradiometry. There is clear improvement in the signal-to-noise ratio of the magnetic field data after linear regression gradiometry has been applied.

Figure 6F:
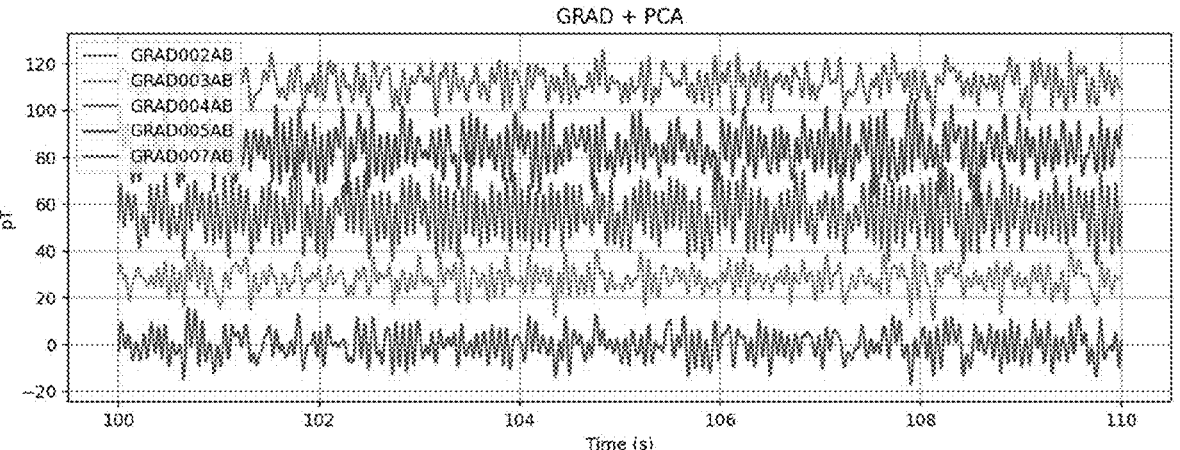

In some embodiments, the denoising process includes applying linear regression gradiometry followed by PCA, to a synchronized, filtered dataset. FIG. 6F illustrates the synchronized, filtered time-series magnetic data in FIG. 6B, after linear regression gradiometry followed by PCA have been applied.

Figure 6G:
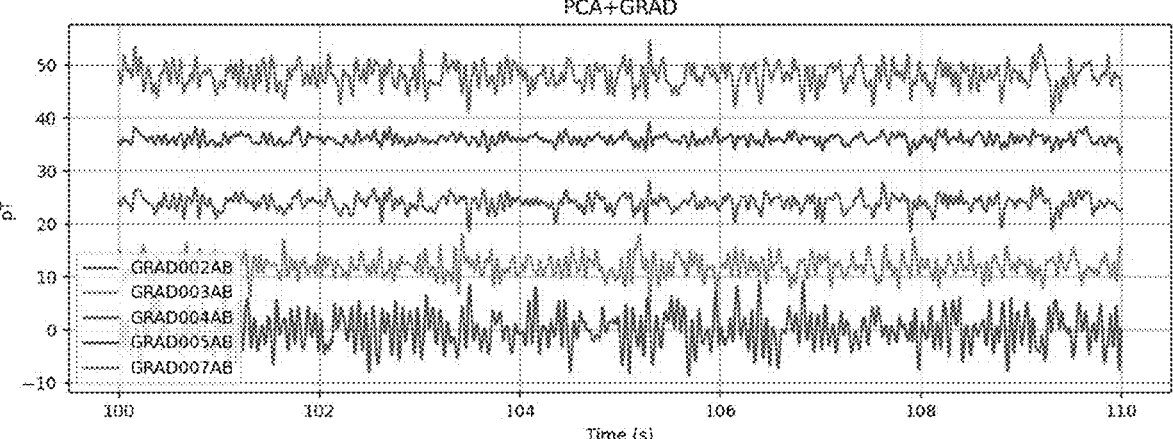

In some embodiments, the denoising process includes applying PCA followed by linear regression gradiometry, to a synchronized, filtered dataset. FIG. 6G illustrates the synchronized, filtered time-series magnetic data in FIG. 6B, after PCA followed by linear regression gradiometry have been applied.

Strong background reduction is evident from the y-axis scale in the transition from FIG. 6A to FIGS. 6B to 6G. Between the raw data in FIG. 6A and the processed data in FIGS. 6F and 6G, there is four orders of magnitude reduction in the noise.

Unlike PCA, in which the number of channels remains the same after PCA is applied to a dataset, in linear regression gradiometry, the number of channels is reduced by half after linear regression gradiometry is applied to a dataset.

If the final number of signal channels is not critical (for example, looking for MCG waveforms instead of maps) linear regression gradiometry provides a more direct and reliable method to remove common mode noise, especially when there may be shared electronic noise among sensor pairs. In lower-noise environments, linear regression gradiometry is likely to be sufficient to recover MCG signals from background.

In terms of whether linear regression or PCA should be applied (and which should be applied first), one should consider the magnetometer array design (e.g., whether the magnetometer array is optimized to maximize gradiometric signals) and the presence of magnetic common mode noise. But it almost entirely depends on the character of the noise, which can vary from dataset to dataset in the high noise environments in which the device is operated. One can consider any number of characteristics about the noise field, including the amplitude, the first-and second-order spatial gradients, the divergence and curl of the noise fields, and more. In some circumstances, these factors are impractical to know. In some embodiments, a heuristic approach is taken, whereby different denoising pipelines are applied and the results evaluated based on the obtained signal-to-noise ratio.

In some embodiments, the denoising process includes applying scaled/banded gradiometry 556. Scaled gradiometry is similar to linear regression gradiometry, except that instead of fitting a scale factor (e.g., β) based on the linear regression, signals from pairwise sensors are scaled based on the ratio between their median absolute deviation (MAD). In banded gradiometry, reference signals are filtered into frequency bands that can vary between 1-10 Hz segments, and each band is then used as a regressor from the signal channel.

In some embodiments, applying banded gradiometry includes filtering a reference channel with n different bidirectional bandpass filters, where the width of the bandpass window can vary between 1 and 10 Hz, resulting in n new time-series data from a given reference. Each of these n new time-series data is then used as a regressor in a GLM model on the target signal.

In some embodiments, the denoising process includes applying independent component analysis (ICA) 557. ICA is a blind source separation technique that separates out a multivariate signal into new components that are maximally statistically independent. ICA algorithms assume that source signals are mutually independent and that the values in each source have non-Gaussian distributions. ICA can be useful in denoising MCG signals because the cardiac sources can be reasonably assumed to be independent from external noise sources. However, the sources are not expected to be stationary—they may translate/rotate in space as the cardiac source, which would limit ICA's effectiveness in isolating cardiac source signals.

Applying ICA after other denoising methods like filtering and PCA can be effective in decomposing the signals into cardiac and non-cardiac sources, even if cardiac signals may be distributed across multiple components. ICA components are not sorted by any useful metric, but the components can be epoched and averaged in order to aid in classifying components that contain cardiac source signals. In some embodiments, the noise rejection techniques disclosed herein include discarding component sources that do not obviously contain cardiac waveform features.

In some embodiments, the denoising process includes applying signal-space separation (SSS) 558 to the filtered data. SSS is a technique based on the physics of electromagnetic fields. SSS separates the measured signal into components attributable to sources inside the measurement volume of the magnetometer array (the internal components), and components attributable to sources outside the measurement volume (the external components). The internal and external components are linearly independent, so it is possible to simply discard the external components to reduce environmental noise. Typically, SSS and Maxwell filtering are performed together. Maxwell filtering is a related procedure that omits the higher-order components of the internal subspace, which are dominated by sensor noise.

Signal space projection (SSP) 559 is another technique for removing noise from MCG signals by projecting the signal onto a lower-dimensional subspace. The subspace is chosen by calculating the average pattern across sensors when the noise is present, treating that pattern as a "direction" in the sensor space, and constructing the subspace to be orthogonal to the noise direction. SSP can remove noise from MCG signals when the noise comes from environmental sources (sources outside the subject's body and the MCG system, such as the electromagnetic fields from nearby electrical equipment) and when that noise is stationary (doesn't change much over the duration of the recording).

In some embodiments, the denoising techniques are selected according to sensor type (e.g., whether the sensor is an OPM, or a diamond NV center magnetometer, or a fluxgate sensor), or more specifically, whether the sensor is scalar or vector (e.g., single-axis or multi-axis vector). Scalar OPMs in an array inherently have good relative alignment with each other, assuming the heading field is spatially homogeneous, and the calibration is based on physical constants, meaning that gradiometry works very well for them and would be preferable. Multi-axis vector sensors (like diamond NV center magnetometers) may not have external references to align sensing axes from multiple sensors, but have a higher channel density per volume, implying that statistical techniques like PCA, as well as other extended techniques based on spatial characteristics of fields (e.g., SSP or SSS) may be more appropriate.

With continued reference to FIG. 5B, after applying the noise rejection techniques, the workflow 500 continues to the epoching step (step 560). An epoch is a period of time around a certain heartbeat. Specifically, an epoch can be defined as x ms prior to, and y ms after the R-wave peak of a given heartbeat. x and y are adjustable depending on the desired analysis goal, but typical values are x=300, y=500, for a total epoch window of 800 ms. This window length allows one to capture P, QRS, and T wave features in most subjects.

Figure 10:
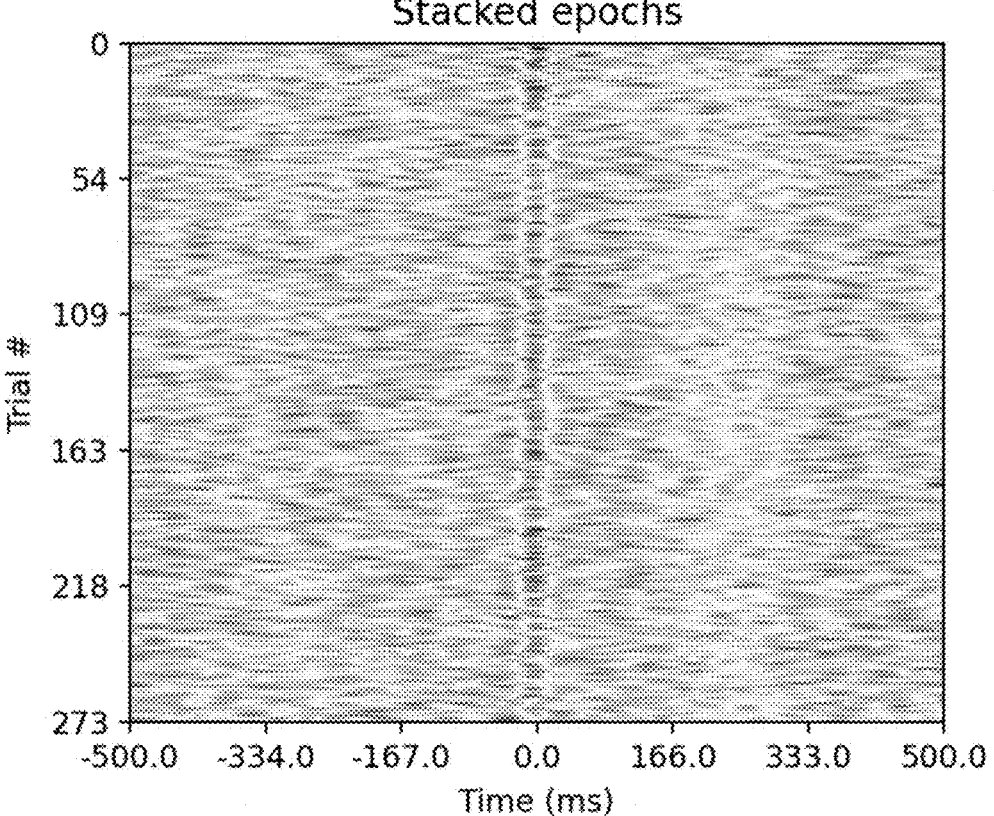
FIG. 10 illustrates a stacked epoch plot showing single trial MCGs visible in an unshielded operation, in accordance with some embodiments.

In some embodiments, the time-series magnetic data is collected over a time period (e.g., 5 minutes or 10 minutes) and corresponds to many heartbeat events. Each heartbeat has a respective signal-to-noise ratio, and one can obtain better data by combining the data (e.g., from one channel) and averaging the data. Channel synchronization of the data, as described in step 520, is key to performing this subsequent step of combining and averaging the data. In some embodiments, the computing device aligns a subset of the synchronized time-series magnetic data, corresponding to a respective magnetometer channel, over several heartbeat events based on a trigger signal (e.g., the trigger signal can be a signal that identifies the start of a heartbeat, a contraction of a ventricle, etc.), to generate a respective subset of aligned signals. The computing device combines (e.g., aggregates, averages, etc.) the respective aligned subset of the synchronized time-series magnetic data over the heartbeat events. Because the noise is different across the several heartbeat events, aggregating and averaging the heartbeat signals reduces the noise while improving the signal. In some embodiments, the trigger signal is a signal detected by electrocardiography (ECG) (562). In some embodiments, the trigger signal is a signal detected by MCG (564). In some embodiments, the trigger signal is pulse oximetry. FIG. 10 illustrates a stacked epoch plot showing single trial MCGs visible in an unshielded operation. In accordance with some embodiments of the present disclosure, the combination of sensor choice (e.g., scalar OPMs, total-field OPMs, fluxgate sensors, and/or NV diamond sensors), array design, and sensor count on the multichannel device/system 200, coupled with the denoising processes disclosed, enables the system/device to effectively reject ambient magnetic interference without magnetic shielding.

Figure 11A:
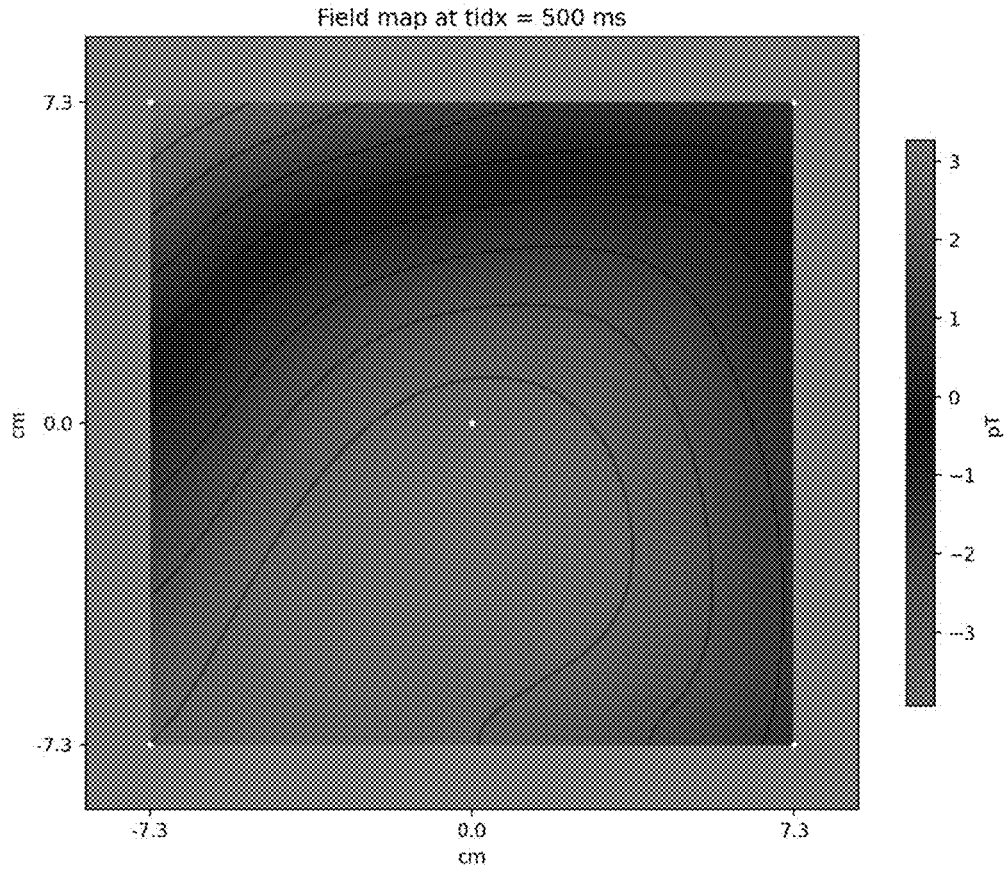
FIGS. 11A and 11B illustrate a spatial magnetic field map for a time slice in accordance with some embodiments.
Figure 11B:
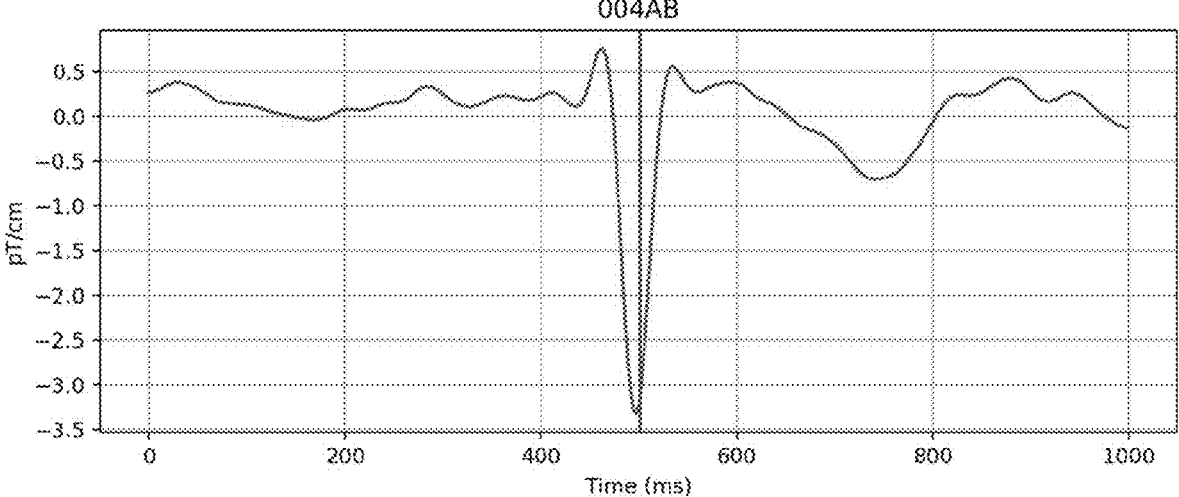

With continued reference to FIG. 5B, in some embodiments, after epoching, the workflow 500 proceeds to the field mapping step (step 570). Here, the computing device generates a magnetic field map by correlating (e.g., mapping) the magnetic field measurements to real-space locations (e.g., spatial positions) of the magnetometers in the array. The computing device can then construct spatial "heat maps" for each slice of time across the sensor array. FIG. 11A illustrates a spatial magnetic field map for time slice t=500 ms. FIG. 11B is a line graph showing changes in magnetic field per unit length over time, for a pair of magnetometers MAG004A and MAG004B.

In some embodiments, the computing device uses a priori information about the (e.g., fixed) array configuration (572), to map the magnetic field data of a channel to the corresponding positional information (e.g., spatial location, positional coordinates, magnetometer element number in the array of magnetometers, separation between magnetometers, etc.) of the magnetometer. In some embodiments, the computing device determines (e.g., obtains) the positional information (574) of the magnetometers in the array in real time (e.g., when the computing device receives the data, as the magnetic field data is collected by the magnetometer array, etc.), and correlates the positional information with the magnetic field data collected by the channels.

Investigation Design and Set-up

In accordance with some embodiments, the MCG system 250 that is shown in FIG. 4F is deployed in an office environment in close proximity to operational train tracks, power lines, and roads. To evaluate the system 250 in this magnetically unshielded environment, MCG data were acquired from 30 adult participants (multiple MCG sessions per participant, 104 total MCG datasets). A 3-lead ECG was recorded simultaneously to provide high signal-to-noise timing triggers to average the MCG data. Participants provided informed written consent prior to collection of MCG data in each session. Individuals were excluded from participation if they had any history of cardiac disease, pacemakers or metal implants in the torso, were pregnant, or breastfeeding. Demographic information was not tracked or controlled given that this was a non-interventional, feasibility demonstration with no demographic group comparisons.

The majority of participants (n=23) completed four different MCG sessions each lasting 300 s (5 min), with varying measurement conditions: i) For resting state (RS) sessions, participants sat quietly for 5 minutes prior to the scan and remained fully compliant (no speech or movement) throughout the scan. ii) For elevated heart rate or stressed state (SS) sessions, participants exercised for about 3 minutes prior to the scan and then remained at rest throughout the scan. iii) In contrast, for non-compliant (NC) sessions, participants sat quietly for at least 5 minutes prior to the scan and were asked to talk animatedly with the device operators throughout the scan. iv) Finally, for magnetic interference (MI) sessions, the bed was modified to have a steel sheet affixed to it, which produced large magnetic field artifacts that were amplified by unintentional participant movements, including those associated with heartbeats. The participant instructions were identical to the RS measurement.

Prior to MCG data acquisition, participants were instructed to lie supine on the gantry bed with the backrest adjusted to 10 degrees above horizontal. ECG was collected with three non-magnetic surface electrodes (Ambu Neuroline 715), placed at the right wrist (RA), left wrist (LA) and bottom right section of the thorax (Ref). The MCG sensor head was then positioned above each participant's thorax using a repeatable protocol. Specifically, the central notches of the patient-facing sensor array lid were aligned with a participant's left-eye, and centered on the line connecting their armpits along the perpendicular axis. After centering the sensor array, an average distance of approximately 4 cm was maintained between the front of the sensor panel and each participant's chest, ample space for participants to breathe normally during MCG acquisition without physically making contact with the sensor panel.

Figure 12:
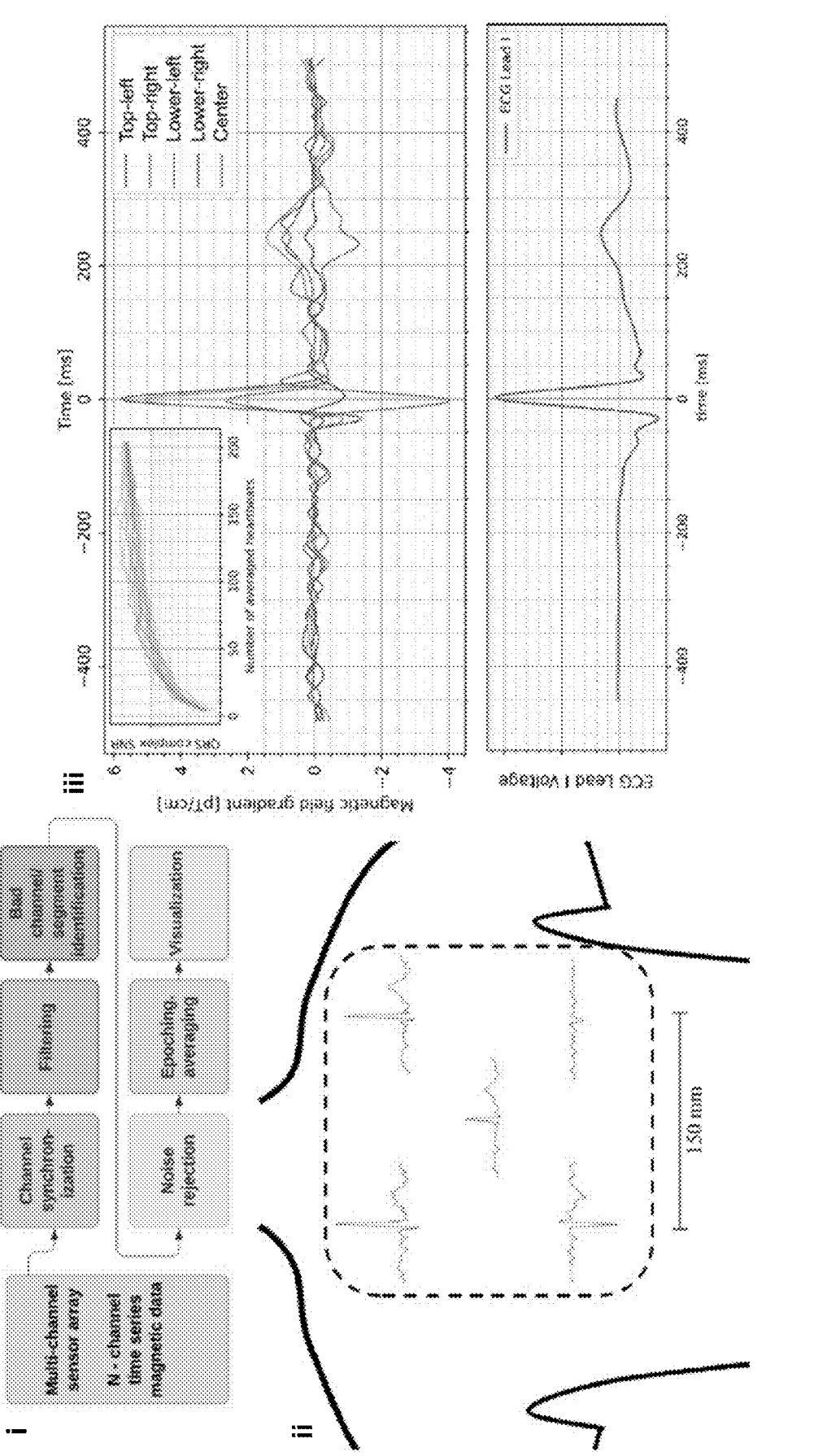
FIG. 12 illustrates exemplary data collected from participants of a MCG study, in accordance with some embodiments.

FIG. 12 illustrates exemplary data collected from participants of a MCG study, in accordance with some embodiments.

Panel i of FIG. 12 shows a signal processing pipeline flowchart that includes the processing steps for time series data acquired from a multi-channel sensor array in the study. After data are loaded, channel synchronization is performed by aligning common signals that were injected in all channels, including the ECG, which is up-sampled to optimize trigger timing. Filtering follows, which consists of a 60 Hz IRR notch filter and 0.5-45 Hz bandpass using a bi-directional Butterworth digital filter. Then, bad channels and segments are identified in and removed from the data using automatic power thresholding and basic data checks. The noise rejection step uses a combination of gradiometry and Principal Component Analysis (PCA), where signal components that have high noise character are removed. MCG epochs are identified using ECG as a trigger, with automated epoch rejection based on signal power and timing criteria. Finally, epochs are averaged together and the epoch-average is visualized.

For gradiometry, signals from vertically (normal to the chest) adjacent sensors were subtracted to form gradiometric signals with a 6.5 cm baseline. To ensure calibration accuracy of the sensors, common-mode fields across sensors were used to measure possible deviations in balancing weights for gradiometry. To do so, linear-regression was performed on sensor pairs. In practice, the balancing coefficients were all equal to 1 within the expected calibration limits of the sensors, confirming that the sensors were faithfully reporting absolute magnetic field. In an unshielded environment, common mode variance across sensors is heavily dominated by signals that are common across both the original and gradiometer array. PCA on the original 10 channels can be augmented by making the 5 gradiometry channels available to train PCA filters, while limiting the number of components to 10. This way, the common mode signals that were imperfectly canceled in gradiometry filtering can be captured. Typically, the first two or three principal components are readily identified as noise and removed before reprojecting the components back into signal space, a technique similar in concept to signal space projection (SSP).

In this study, the use of gradiometry and PCA enables heart signals to be discriminated from environmental noise, and produces epoch-averaged MCG waveforms exhibiting clear QRS and T-wave features for the four different experimental conditions (resting state, elevated heart rate/stressed state, participant non-compliance, and increased magnetic interference).

In the epoching/averaging step, ECG data were collected and analyzed in parallel to the MCG in order to identify time segments, or epochs, where heartbeats occurred. ECG lead 1 (LA-RA) was bandpass filtered between 0.5 Hz and 45 Hz using a bi-directional Butterworth digital filter. The filtered ECG was thresholded automatically to find potential QRS times (with false triggers being excluded based on relative timing). These trigger times are further refined by evaluating a 200 ms window around the initial guess using a peak-finding algorithm. These triggers were then used to divide the MCG data into epochs of 1000 ms. Epochs were excluded based upon integrated signal power (highest 20% of signal power epochs were excluded) and the remaining epochs were averaged together (FIG. 12, panels ii and iii).

In Panel ii of FIG. 12, the epoch-average for each gradiometer channel is displayed based on approximate relative positions over the participant's chest. The upper right sensor and lower left sensor show inverted features. The upper plot in panel iii of FIG. 12 shows epoch-average of all five gradiometric signals overlayed. In panel iii, the epoch-average of all five gradiometric signals are overlayed. For the data in FIG. 12, a total of 214 epochs can be averaged together, but SNR>10 is possible with as few as 60 epochs (~1 minute of data), as shown in the inset of FIG. 12 panel iii. ECG Lead I trace that was acquired simultaneously with the MCG data. The corresponding ECG trace, averaged over 214 epochs, is shown in the lower plot of FIG. 2, panel iii.

The mean number of epochs that are averaged together per dataset is 191 (median 192), with a standard deviation of 41. Over 90% of the peak SNR can be achieved within 144 (mean) averaged epochs, consistent with the noise decreasing at an observed rate of $1/\mathrm{sqrt}(N)$, where N is the number of averages.

In the currently reported-on system, epoching without the aid of ECG typically recovers fewer than 30% of heartbeats, while using the ECG can identify 100%, or very close to 100% of heartbeats. Unshielded interference is challenging to systematically remove from the magnetometer data without distorting heartbeat morphology. Therefore, after the denoising steps above, the SNR of individual channel time-series data remains insufficient to consistently identify heartbeat timing with the required accuracy for epoch averaging. In ischemia triage, the extra information and reliability makes the tradeoff of adding an ECG subsystem worthwhile.

The resulting epoch-averages on 5 gradiometer channels were fitted using a generic multi-peak fitting function, designed to capture the QRS and T-wave feature amplitudes, as well as intervals between features. These amplitudes were used to calculate the signal-to-noise ratio (SNR) for each gradiometer channel, using the peak-to-peak of the QRS complex segment as the signal, and the standard deviation of the segment 200-400 ms prior to the onset of the Q-wave as noise. While this definition leads to reduced SNR reporting than a more standard power-based estimation may give, it better captures the feasibility of feature extraction. $SNR_{max}$ is defined to be the highest signal-to-noise ratio (SNR) across all 5 gradiometry channels in each dataset.

Each dataset was loaded via an automated pipeline that performed the above steps with algorithmically chosen parameters. Datasets in which the automatic pipeline failed to complete (~30%) due to technical issues or due to excessive noise were analyzed manually, using the same processing steps but with manually selected bad segment identification and parameters for denoising.

After completing data collection for this study, group statistics were performed to understand the distribution of SNR across participants and experimental conditions. Specifically, statistics on QRS-SNR are reported because it was found that the T-wave SNR is more dependent on the relative positioning of each magnetic sensor with respect to the heart.

Mixed modeling (python statsmodels==0.14.1) was utilized to evaluate the hypothesis that there would be no significant differences in SNR by experimental condition. Utilizing the resting condition as the reference group, we compared each of the three other experimental conditions to the reference group using dummy coding. The dummy-coded variables (0, 1) were entered as a fixed effect at Level 1 of the hierarchical linear model, predicting SNR as the outcome, with participants entered as a random effect at Level 2 of the same model. Because this configuration naturally yields three comparisons with the resting state (as the reference group), a Bonferonni post-hoc correction was applied to adjust the critical alpha to 0.017.

Of the 104 MCG datasets acquired from the device in this technical feasibility study, 95 (91%) datasets showed clear (SNR>3) QRS complex among gradiometer channels in the epoch-averaged MCG signal. In the datasets with clear MCG signal visibility and prior to epoch averaging, the background white noise rejection ratio was in excess of 100 at 1 Hz, while common mode rejection of narrow band noise overlapping with the MCG signal spectral content was in excess of 1000. The epoch-averaged signal achieved SNR above 20 for 55% of datasets, allowing distinction of QRS and T-wave features that correspond to features in the simultaneously acquired ECG, as illustrated in FIG. 12, panel iii.

Figure 13:
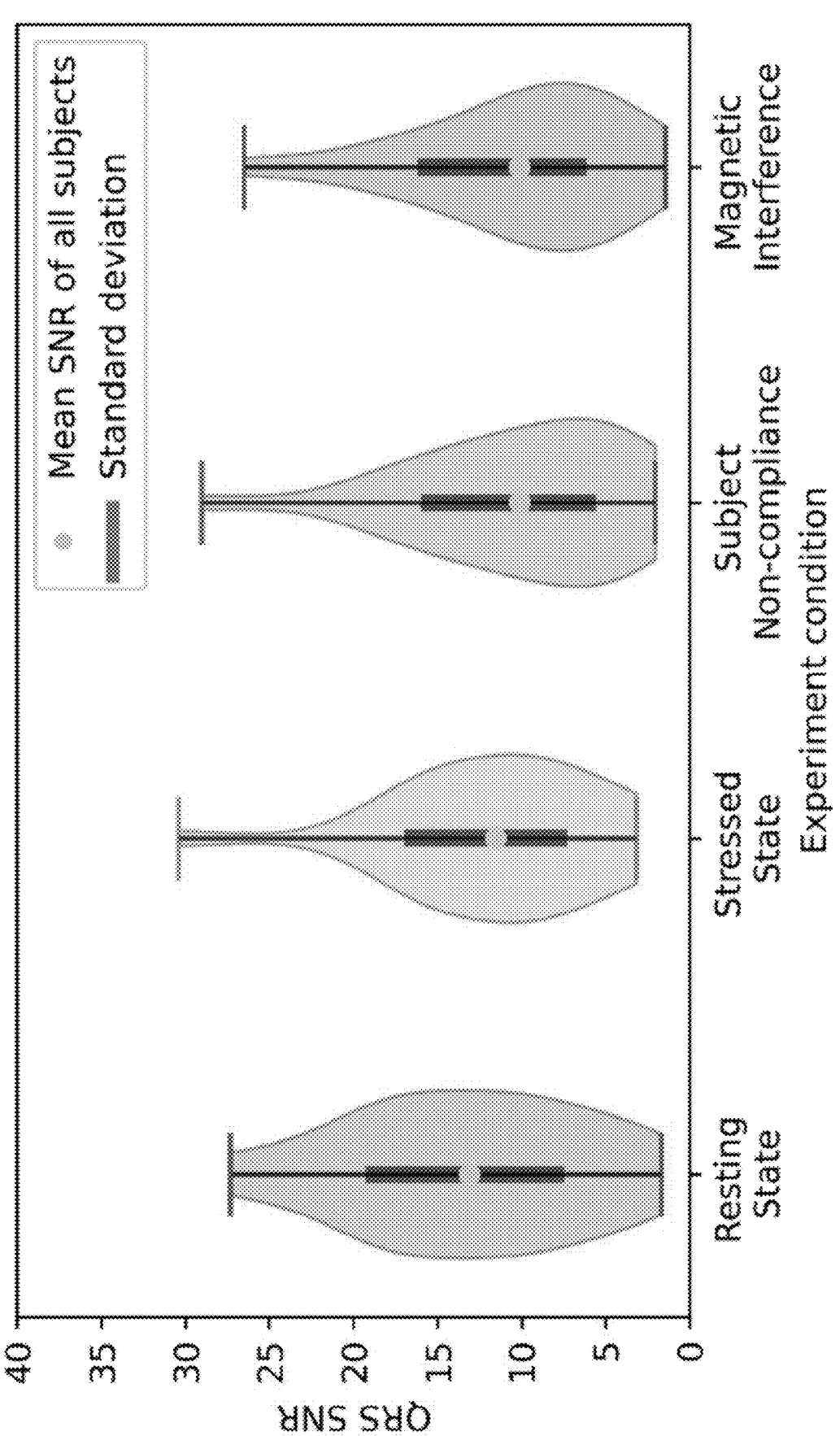
FIG. 13 provides a summary of maximum signal-to-noise ratio separated by experimental condition for participants of a MCG study, in accordance with some embodiments.

FIG. 13 illustrates the distribution of SNR results for participants across conditions. Mixed modeling analyses revealed no significant differences between any condition and the resting state (all p's<0.056 versus a post-hoc corrected critical alpha of 0.017). The results support the hypothesis that the controlled experimental conditions did not significantly influence the SNR distributions.

FIG. 13 provides a summary of $SNR_{max}$ of the heartbeat averages, separated by experimental condition for all participants. The summary is based on data from 23 participants and 92 observations. The mean number of heartbeats averaged together for each participant is 191, and examination of SNR scaling with number of heartbeats shows that this cannot account for the spread in SNR values. The wings of each violin plot represent an empirical distribution of the participant results, computed by kernel density estimation (KDE). The mean SNR is indicated for each experimental condition with a gold dot, with the asymmetric standard deviation of the participant level distribution from the mean reported with the thick black lines. Mixed modeling comparisons across condition-sorted datasets showed that there were no statistically significant differences in the distributions for each condition, indicating that the controlled factors in the study did not meaningfully affect the SNR.

The mean number of epochs averaged for all datasets was 191 with a standard deviation of 41. On all datasets, a decrease in the background noise that scales as 1/sqrt(N), where N is the number of epochs is observed. This implies that for a fixed signal amplitude, the SNR could vary by up to 11% based on the differences in number of averages. It is also observed that SNR reaches 90% of its final value (after all epochs averaged) after 141 epochs, on average. Meanwhile the standard deviation in SNR for the resting state data is nearly 50%. Therefore the variation in number of heartbeats averaged together cannot account for the spread in SNR values.

With low spatial resolution, magnetic field maps from which current dipole sources may be accurately estimated are not possible. However, in a qualitative evaluation of the MCG deflection from FIG. 12, panel ii, an inversion of the magnetic field amplitude from the upper right sensor to the lower left sensor is observed. This spatial feature follows from the expected dipolar angle during repolarization for healthy participants. The dipolar angle is related to the angle of the equivalent current dipole during the T-wave and has been shown to have sensitivity to ischemic conditions in the heart.

For this reported-on system operating in challenging environments, data processing without ECG triggering results in SNR lower than 3 in the majority of datasets, while including ECG significantly boosts the SNR. As the device aims to be deployed in clinical settings where the environmental interference will almost certainly be higher, the challenge of extracting single heartbeats will be even greater, even as sensor channels are added and denoising algorithms improve.

In applications for the disclosed device such as ischemia triage in emergency rooms, the inclusion of a concurrent ECG is not known to impede the clinical workflow while providing a substantial enhancement to the MCG SNR Demonstration of the MCG device/system 250 on volunteers over a set of conditions indicated that MCG recordings can be reliably acquired using non-shielded magnetometers, in a non-magnetically shielded environment, in the presence of magnetic objects, even when participants were not perfectly calm and compliant. The work presented here opens up the possibility of deploying the system in bedside clinical settings.

Flowchart

FIGS. 14A to 14D provide a flowchart of a method 700 for determining magnetic fields from an organ of a human subject (e.g., a heart or a brain of a human subject) according to some embodiments. Some of the processes disclosed in the method 700 reduce/remove signals from interference sources and enable the disclosed device and system to be operable without magnetic shielding. The method 700 is performed at a computing system (e.g., computer system 120) having one or more processors (e.g., CPU(s) 302 and memory (e.g., memory (306). The memory stores one or more programs configured for execution by the one or more processors. In some embodiments, the operations shown in FIGS. 1A, 1B, 4A to 4G, 5A, 5B, 6A to 6G, 7A, 7B, 8, 9A, 9B, 10, 11A, 11B, 12, and 13 correspond to instructions stored in the memory 206 or other non-transitory computer-readable storage medium. The computer-readable storage medium may include a magnetic or optical disk storage device, solid state storage devices such as Flash memory, or other non-volatile memory device or devices. In some embodiments, the instructions stored on the computer-readable storage medium include one or more of: source code, assembly language code, object code, or other instruction format that is interpreted by one or more processors. Some operations in the method 700 may be combined and/or the order of some operations may be changed.

The computer system receives (702) a plurality of signals corresponding to first time-series magnetic data (e.g., magnetic field data) generated from (e.g., by) a plurality of magnetometers (e.g., magnetic field sensors) proximate to the human subject (e.g., 2 cm from the human subject). The first time-series magnetic data corresponds to magnetic fields generated from the human subject.

In some embodiments, the computer system and the plurality of magnetometers are co-located at the same location. For example, the computer system and the plurality of magnetometers are located in the same room where the plurality of magnetometers is deployed (e.g., employed). In some embodiments, the computer system and the plurality of magnetometers are located at different locations. In some embodiments, the computer system is on the cloud.

In some embodiments, the plurality of magnetometers is magnetically unshielded.

In some embodiments, the plurality of magnetometers is operating in (e.g., is located in) a magnetically unshielded environment (e.g., magnetically unshielded room).

In some embodiments, the plurality of magnetometers is operating at room temperature.

In some embodiments, each magnetometer in the plurality of magnetometers comprises an optically pumped magnetometer (OPM).

In some embodiments, each magnetometer in the plurality of magnetometers comprises a diamond nitrogen vacancy (NV) center magnetometer.

In some embodiments, each magnetometer in the plurality of magnetometers comprises a fluxgate sensor.

In some embodiments, the array of magnetometers includes at least one OPM and at least one diamond NV center magnetometer.

In some embodiments, the plurality of magnetometers is (704) an m×n array of magnetometers arranged in a stack of p planes. m is a number of magnetometers in a length direction (e.g., along the x-axis) of the array, n is a number of magnetometers in a width direction (e.g., along the y-axis) of the array, and p is a number of planes, in the stack of planes, arranged in a height direction (e.g., along the z-axis) of the array.

The computer system synchronizes (706) the first time-series magnetic data to a common clock (e.g., a common time reference) to generate synchronized time-series magnetic data.

The computer system applies (708) one or more filters to the synchronized time-series magnetic data to obtain filtered data.

In some embodiments, applying one or more filters to the synchronized time-series magnetic data comprises applying (710) a notch filter (e.g., an infinite impulse response (IIR) filter or a band stop filter) having a frequency of an electrical line noise (e.g., 50 Hz or 60 Hz).

In some embodiments, applying one or more filters to the synchronized time-series magnetic data comprises applying (712) a bandpass filter.

In some instances, the bandpass filter includes (714) a frequency range of 0.5 Hz to 40 Hz.

Referring to FIG. 14B, in some embodiments, the computer system applies (716) one or more noise reduction (e.g., denoising) techniques to the filtered data to generate updated time-series magnetic data. The updated time-series magnetic data has an improved signal-to-noise ratio compared to the first time-series magnetic data.

The one or more noise reduction techniques can include linear regression gradiometry. In some embodiments, the stack of p planes includes a first plane and a second plane that is adjacent to the first plane. Applying one or more noise reduction techniques to the filtered data includes obtaining (718) positional information corresponding to each magnetometer in the array of magnetometers. For a respective pair of magnetometers, in the array of magnetometers, consisting of a respective first magnetometer positioned in the first plane and a respective second magnetometer positioned in the second plane, wherein the respective first magnetometer and the second respective magnetometer are aligned with respect to each other in the length direction and the width direction, the computer device calculates (720) a difference between a first filtered signal corresponding to the respective first magnetometer and a second filtered signal corresponding to the second respective magnetometer.

In general, in linear regression gradiometry, the number of channels is reduced by half because this technique combines signals from pairs of magnetometers and calculates their difference.

In some embodiments, calculating the difference between the first filtered signal corresponding to the respective first magnetometer and the second filtered signal corresponding to the second respective magnetometer further includes determining (722) a correlation between the first filtered signal and the filtered second signal using linear regression and calculating (724) the difference according to the determined correlation.

As an example, the respective first magnetometer is Magnetometer A and the respective second magnetometer is Magnetometer B. Magnetometer A and Magnetometer B are aligned along the length and the width of the array of magnetometers (i.e., they have the same x- and y-positions). The calculated difference is $Signal_A - \beta \times Signal_B$, wherein $Signal_A$ corresponds to the filtered signal from Magnetometer A, $Signal_B$ corresponds to the filtered signal from Magnetometer B, and $\beta$ is the scaling factor between the signal from Magnetometer A and the signal from Magnetometer B.

In some embodiments, applying one or more noise reduction techniques to the filtered data includes applying (726) principal component analysis (PCA) to extract, from the filtered data, a subset of variables from all variables of the filtered data. Unlike linear regression gradiometry, in which the number of signal channels is reduced by half, the number of signal channels remains the same for PCA. In some embodiments, applying PCA includes determining (727) a plurality of principal components (PCs) corresponding to the filtered data and assigning a value of zero to a subset of the plurality of PCs, thereby removing one or more noise contributions from the filtered data.

In some embodiments, applying one or more noise reduction techniques to the filtered data includes applying (728) signal source separation (SSS) to the filtered data With continued reference to FIG. 14C, in some embodiments, the synchronized time-series magnetic data comprises magnetic data that are recorded over a plurality of events (e.g., epochs or heartbeat events). The method 700 further comprises, for a respective magnetometer of the array of magnetometers: aligning (729) a respective subset of the synchronized time-series magnetic data corresponding to the respective magnetometer over the plurality of events based on a trigger signal (e.g., the trigger signal can a signal that identifies the start of a heartbeat, a contraction of a ventricle, etc.) to generate a respective subset of aligned signals; and combining (730) (e.g., aggregating, averaging, etc.) the respective aligned subset of the synchronized time-series magnetic data over the plurality of events.

In some embodiments, the computer system obtains (732) positional information (e.g., positional coordinates, magnetometer element number in the array of magnetometers, separation between magnetometers, etc.) corresponding to each magnetometer in the array of magnetometers and correlates (734) (e.g., maps) a respective signal of the plurality of signals to the obtained positional information.

In some embodiments, the updated time-series magnetic data includes a plurality of updated signals corresponding to respective magnetometers in the array of magnetometers.

The computer device obtains (736) positional information (e.g., spatial location, positional coordinates, magnetometer element number in the array of magnetometers, separation between magnetometers, etc.) corresponding to each magnetometer in the array of magnetometers. The computer device correlates (e.g., maps) a respective updated signal of the plurality of updated signals to a respective magnetometer based on the obtained positional information. The computer device generates (740) a magnetic field map (e.g., a two-dimensional map, a data visualization) that spatially correlates a magnetic field distribution around the organ of the human subject with the positional information of each magnetometer in the array of magnetometers, and causes (742) display of the magnetic field map on a display device (e.g., output device(s) 312, or a user device that is communicatively connected to the computer system).

Figure 14D:

Referring to FIG. 14D, in some embodiments, the plurality of magnetometers comprises (744) a plurality of vector magnetometers. The method 700 further includes: after receiving the plurality of signals, corresponding to vector field signals from the plurality of vector magnetometers, calibrating and processing the plurality of signals according to physical sensor orientation of the plurality of vector magnetometers. In the case of 2- or 3-axis vector measurements, the method includes employing the methods disclosed above to take advantage of the higher information density. Vector magnetometers, which report two- or three-axis vector measurements from a single location in space, have inherently higher spatial information density than single-axis or scalar magnetometers. Statistical techniques such as PCA and SSS benefit from higher spatial information density because their ability to resolve nearby versus far sources depends on the spatial sampling frequency of the sensor array.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "exemplary" means "serving as an example, instance, or illustration," and does not necessarily indicate any preference or superiority of the example over any other configurations or embodiments.

As used herein, the term "and/or" encompasses any combination of listed elements. For example, "A, B, and/or C" includes the following sets of elements: A only, B only, C only, A and B without C, A and C without B, B and C without A, and a combination of all three elements, A, B, and C.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method for determining magnetic fields from an organ of a human subject, comprising:

at a computer system having one or more processors and memory:

receiving a plurality of signals corresponding to first time-series magnetic data generated from a plurality of unshielded magnetometers proximate to the human subject, the first time-series magnetic data corresponding to magnetic fields generated from the human subject, wherein:

the plurality of unshielded magnetometers comprises an m×n array of magnetometers arranged in a stack of p planes, wherein m is a number of magnetometers in a length direction of the array, n is a number of magnetometers in a width direction of the array, and p is a number of planes, in the stack of planes, arranged in a height direction of the array, the stack of p planes including a first plane and a second plane that is adjacent to the first plane; and the plurality of signals include contributions from a biomagnetic field from at least a portion of the human subject's organ and a background magnetic field;

synchronizing the first time-series magnetic data to a common clock to generate synchronized time-series magnetic data;

applying one or more filters to the synchronized time-series magnetic data to obtain filtered data; and applying one or more noise reduction techniques to the filtered data to generate updated time-series magnetic data, including:

obtaining positional information corresponding to each magnetometer in the array of magnetometers; and for a respective pair of magnetometers, in the array of magnetometers, consisting of a respective first magnetometer positioned in the first plane and a respective second magnetometer positioned in the second plane, wherein the respective first magnetometer and the second respective magnetometer are aligned with respect to each other in the length direction and the width direction:

calculating a difference between a first filtered signal corresponding to the respective first magnetometer and a second filtered signal corresponding to the second respective magnetometer.

2. The method of claim 1, wherein applying one or more filters to the synchronized time-series magnetic data comprises applying a notch filter having a frequency of an electrical line noise.

3. The method of any of claim 1, wherein applying one or more filters to the synchronized time-series magnetic data comprises applying a bandpass filter.

4. The method of claim 3, wherein the bandpass filter includes a frequency range of 0.5 Hz to 40 Hz.

5. The method of claim 1, wherein calculating the difference between the first filtered signal corresponding to the respective first magnetometer and the second filtered signal corresponding to the second respective magnetometer further includes:

determining a correlation between the first filtered signal and the filtered second signal using linear regression; and calculating the difference according to the determined correlation.

6. The method of claim 1, wherein applying one or more noise reduction techniques to the filtered data includes applying principal component analysis (PCA) to extract, from the filtered data, a subset of variables from all variables of the filtered data.

7. The method of claim 6, wherein applying PCA includes:

determining a plurality of principal components (PCs) corresponding to the filtered data; and assigning a value of zero to a subset of the plurality of PCs, thereby removing one or more noise contributions from the filtered data.

8. The method of claim 1, wherein applying one or more noise reduction techniques to the filtered data includes applying signal source separation (SSS) to the filtered data.

9. The method of claim 1, wherein:

the plurality of magnetometers comprises an array of magnetometers;

the synchronized time-series magnetic data comprises magnetic data that are recorded over a plurality of events; and the method further comprises, for a respective magnetometer of the array of magnetometers:

aligning a respective subset of the synchronized time-series magnetic data corresponding to the respective magnetometer over the plurality of events based on a trigger signal to generate a respective subset of aligned signals; and combining the respective aligned subset of the synchronized time-series magnetic data over the plurality of events.

10. The method of claim 1, wherein:

the plurality of magnetometers comprises an array of magnetometers; and the method further comprises:

obtaining positional information corresponding to each magnetometer in the array of magnetometers; and correlating a respective signal of the plurality of signals to the obtained positional information.

11. The method of claim 1, wherein:

the plurality of magnetometers comprises an array of magnetometers;

the updated time-series magnetic data includes a plurality of updated signals corresponding to respective magnetometers in the array of magnetometers; and the method further comprises:

obtaining positional information corresponding to each magnetometer in the plurality of magnetometers;

correlating a respective updated signal of the plurality of updated signals to a respective magnetometer based on the obtained positional information;

generating a magnetic field map that spatially correlates a magnetic field distribution of the organ of the human subject with the positional information of each magnetometer in the array of magnetometers; and causing display of the magnetic field map on a display device.

12. The method of claim 1, wherein the plurality of magnetometers includes at least one optically pumped magnetometer (OPM).

13. The method of claim 1, wherein the plurality of magnetometers includes at least one diamond nitrogen vacancy (NV) center magnetometer.

14. The method of claim 1, wherein the plurality of magnetometers includes at least one fluxgate magnetometer.

15. The method of claim 1, wherein:

the plurality of magnetometers comprises a plurality of vector magnetometers; and the method further comprises:

after receiving the plurality of signals, corresponding to vector field signals from the plurality of vector magnetometers, computing a dot product of vector field components of the plurality of vector magnetometers to derive the first time-series magnetic data.

16. A computer system for determining magnetic fields from an organ of a human subject, comprising:

one or more processors; and memory; and one or more programs stored in the memory for execution by the one or more processors, the one or more programs including instructions for:

receiving a plurality of signals corresponding to first time-series magnetic data generated from a plurality of unshielded magnetometers proximate to the human subject, the first time-series magnetic data corresponding to magnetic fields generated from the human subject, wherein:

the plurality of unshielded magnetometers comprises an m×n array of magnetometers arranged in a stack of p planes, wherein m is a number of magnetometers in a length direction of the array, n is a number of magnetometers in a width direction of the array, and p is a number of planes, in the stack of planes, arranged in a height direction of the array, the stack of p planes including a first plane and a second plane that is adjacent to the first plane; and the plurality of signals include contributions from a biomagnetic field from at least a portion of the human subject's organ and a background magnetic field;

synchronizing the first time-series magnetic data to a common clock to generate synchronized time-series magnetic data;

applying one or more filters to the synchronized time-series magnetic data to obtain filtered data; and applying one or more noise reduction techniques to the filtered data to generate updated time-series magnetic data, including:

obtaining positional information corresponding to each magnetometer in the array of magnetometers; and for a respective pair of magnetometers, in the array of magnetometers, consisting of a respective first magnetometer positioned in the first plane and a respective second magnetometer positioned in the second plane, wherein the respective first magnetometer and the second respective magnetometer are aligned with respect to each other in the length direction and the width direction:

calculating a difference between a first filtered signal corresponding to the respective first magnetometer and a second filtered signal corresponding to the second respective magnetometer.

17. The computer system of claim 16, wherein the instructions for applying one or more filters to the synchronized time-series magnetic data include instructions for:

applying a notch filter having a frequency of an electrical line noise.

18. A non-transitory computer readable storage medium storing computer-executable instructions that, when executed by one or more processors of a computer system, cause the computer system to perform operations comprising:

receiving a plurality of signals corresponding to first time-series magnetic data generated from a plurality of unshielded magnetometers proximate to a human subject, the first time-series magnetic data corresponding to magnetic fields generated from the human subject, wherein:

the plurality of unshielded magnetometers comprises an m×n array of magnetometers arranged in a stack of p planes, wherein m is a number of magnetometers in a length direction of the array, n is a number of magnetometers in a width direction of the array, and p is a number of planes, in the stack of planes, arranged in a height direction of the array, the stack of p planes including a first plane and a second plane that is adjacent to the first plane; and the plurality of signals include contributions from a biomagnetic field from at least a portion of an organ of the human subject and a background magnetic field;

synchronizing the first time-series magnetic data to a common clock to generate synchronized time-series magnetic data;

applying one or more filters to the synchronized time-series magnetic data to obtain filtered data; and applying one or more noise reduction techniques to the filtered data to generate updated time-series magnetic data, including:

obtaining positional information corresponding to each magnetometer in the array of magnetometers; and for a respective pair of magnetometers, in the array of magnetometers, consisting of a respective first magnetometer positioned in the first plane and a respective second magnetometer positioned in the second plane, wherein the respective first magnetometer and the second respective magnetometer are aligned with respect to each other in the length direction and the width direction:

calculating a difference between a first filtered signal corresponding to the respective first magnetometer and a second filtered signal corresponding to the second respective magnetometer.

* * * * *